United States Patent
Toro et al.

(10) Patent No.: US 10,245,373 B2
(45) Date of Patent: *Apr. 2, 2019

(54) PUMP CASSETTES WITH POSITIONING FEATURE AND INFUSION PUMP SYSTEMS

(71) Applicant: CareFusion 2200, Inc., San Diego, CA (US)

(72) Inventors: Daniel Toro, Chula Vista, CA (US); Corey Michael Magers, Oceanside, CA (US); Santiago Dodge, Santee, CA (US); Robert Vasko, San Diego, CA (US)

(73) Assignee: CareFusion 2200, Inc., San Diego, CA (US)

( * ) Notice: Subject to any disclaimer, the term of this patent is extended or adjusted under 35 U.S.C. 154(b) by 907 days.

This patent is subject to a terminal disclaimer.

(21) Appl. No.: 14/557,447

(22) Filed: Dec. 1, 2014

(65) Prior Publication Data

US 2016/0151561 A1 Jun. 2, 2016

(51) Int. Cl.
*A61M 5/142* (2006.01)

(52) U.S. Cl.
CPC ....... *A61M 5/142* (2013.01); *A61M 2205/121* (2013.01); *A61M 2205/128* (2013.01); *A61M 2205/3327* (2013.01); *A61M 2205/505* (2013.01)

(58) Field of Classification Search
CPC ............ A61M 5/142; A61M 2205/121; A61M 2205/128; A61M 2205/3327; A61M 2205/505
USPC .................................................... 417/477.2
See application file for complete search history.

(56) References Cited

U.S. PATENT DOCUMENTS

| 4,842,584 A | 6/1989 | Pastrone |
| 5,098,262 A | 3/1992 | Wecker et al. |
| 5,554,013 A | 9/1996 | Owens et al. |
| 5,575,632 A * | 11/1996 | Morris ............. A61M 5/14228 128/DIG. 12 |
| 5,807,075 A | 9/1998 | Jacobsen et al. |
| 5,816,779 A | 10/1998 | Lawless et al. |

(Continued)

FOREIGN PATENT DOCUMENTS

| WO | WO-2005097235 A2 | 10/2005 |
| WO | WO-2014190188 A2 | 11/2014 |
| WO | WO-201619090 A1 | 12/2016 |

OTHER PUBLICATIONS

International Search Report and Written Opinion for Application No. PCT/US2015/063001, dated Mar. 8, 2016, 22 pages.

(Continued)

*Primary Examiner* — Theodore Stigell
(74) *Attorney, Agent, or Firm* — Morgan, Lewis & Bockius LLP

(57) ABSTRACT

Pump cassettes, infusion systems, and methods are described. An example pump cassette may include a rigid body comprising a frame portion, a base portion, a compliant membrane disposed substantially therebetween, two opposing edge sections, and an interface-facing surface. The rigid body may include a positioning feature arranged substantially orthogonal to a general plane of the interface-facing surface. The pump cassette may include a slider coupled to the two opposing edge sections and longitudinally articulable with respect to the rigid body.

18 Claims, 53 Drawing Sheets

(56) References Cited

U.S. PATENT DOCUMENTS

| | | | |
|---|---|---|---|
| 5,954,485 | A | 9/1999 | Johnson et al. |
| 6,475,178 | B1 | 11/2002 | Krajewski et al. |
| 6,494,694 | B2 | 12/2002 | Lawless et al. |
| 7,867,189 | B2 | 1/2011 | Childers et al. |
| 7,972,306 | B2 | 7/2011 | Shearn |
| 8,066,671 | B2 | 11/2011 | Busby et al. |
| 8,465,454 | B2 | 6/2013 | Kirkpatrick |
| 8,523,816 | B2 | 9/2013 | Kirkpatrick |
| 8,668,671 | B2 | 3/2014 | Kirkpatrick |
| 8,771,228 | B2 | 7/2014 | Butterfield |
| 8,784,359 | B2 | 7/2014 | Plahey et al. |
| 8,936,447 | B2 | 1/2015 | Abal |
| 2001/0051789 | A1 | 12/2001 | Parsons |
| 2004/0019313 | A1 | 1/2004 | Childers et al. |
| 2007/0213653 | A1 | 9/2007 | Childers et al. |
| 2008/0138223 | A1 | 6/2008 | Lanigan et al. |
| 2008/0262409 | A1 | 10/2008 | Derrico et al. |
| 2009/0062738 | A1 | 3/2009 | Ziegler |
| 2010/0286599 | A1 | 11/2010 | Ziegler et al. |
| 2011/0040244 | A1 | 2/2011 | Busby et al. |
| 2011/0092894 | A1 | 4/2011 | McGill et al. |
| 2011/0178359 | A1 | 7/2011 | Hirschman et al. |
| 2011/0282276 | A1 | 11/2011 | Abal |
| 2012/0053557 | A1 | 3/2012 | Abal |
| 2012/0078218 | A1 | 3/2012 | Barnes |
| 2012/0083759 | A1 | 4/2012 | Kirkpatrick |
| 2012/0177543 | A1 | 7/2012 | Battrell et al. |
| 2012/0179130 | A1 | 7/2012 | Barnes et al. |
| 2013/0106609 | A1 | 5/2013 | Singh et al. |
| 2013/0267899 | A1 | 10/2013 | Robert et al. |
| 2014/0276424 | A1 | 9/2014 | Davis et al. |
| 2014/0276426 | A1 | 9/2014 | Borges et al. |
| 2014/0276533 | A1 | 9/2014 | Butterfield et al. |
| 2017/0032152 | A1 | 2/2017 | Salem et al. |

OTHER PUBLICATIONS

International Search Report and Written Opinion for Application No. PCT/US2015/063002, dated Mar. 8, 2016, 11 pages.
International Search Report and Written Opinion for Application No. PCT/US2015/063007, dated Mar. 8, 2016, 10 pages.
International Search Report and Written Opinion for Application No. PCT/US2015/063010, dated Mar. 8, 2016, 13 pages.
International Search Report and Written Opinion for Application No. PCT/US2015/063013, dated Mar. 8, 2016, 15 pages.
Extended European Search Report for Application No. 15864547.3, dated Aug. 1, 2018, 7 pages.
Extended European Search Report for Application No. 15865327.9, dated Aug. 1, 2018, 7 pages.

\* cited by examiner

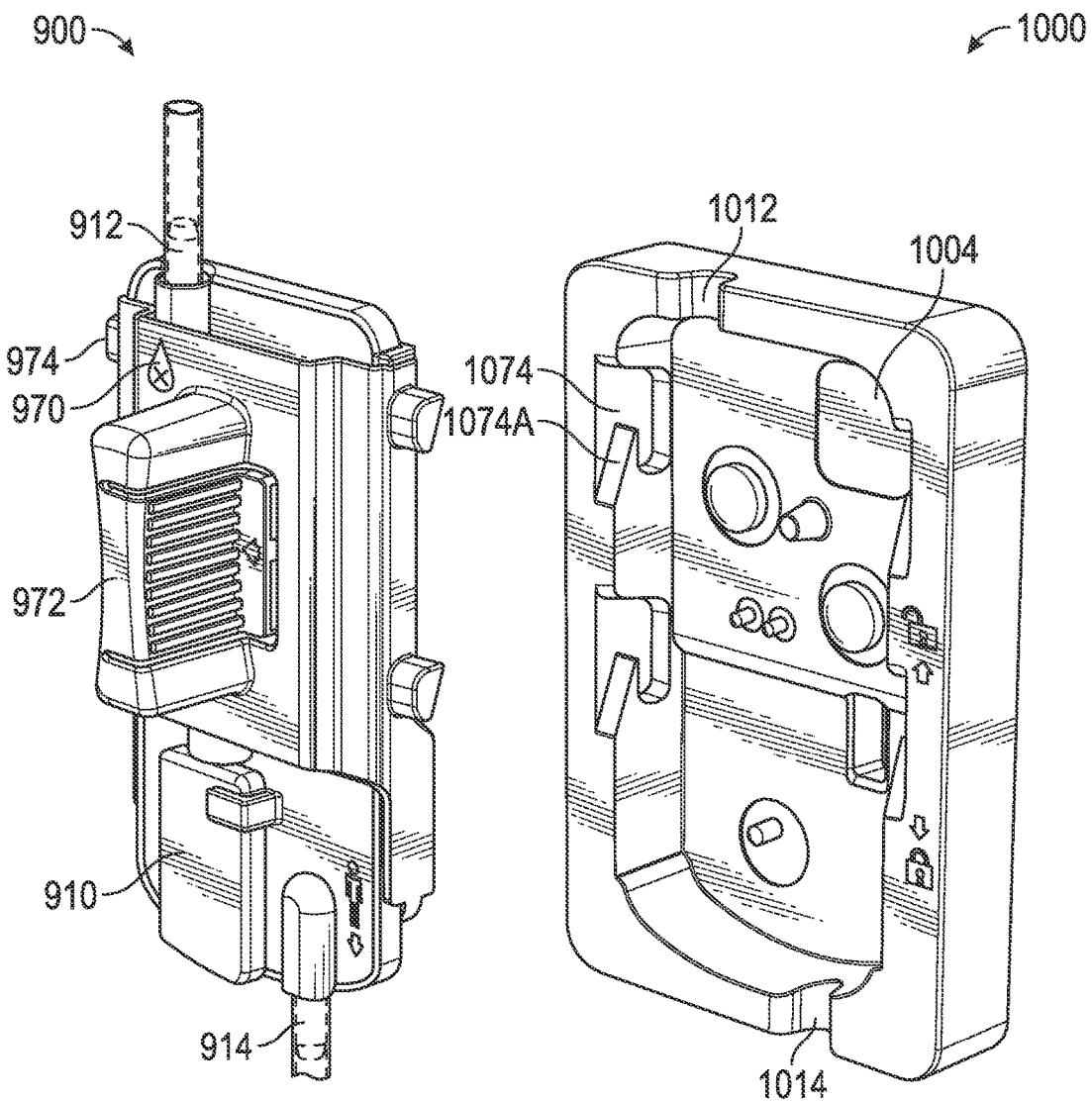

PUMP CASSETTES WITH POSITIONING FEATURE AND INFUSION PUMP SYSTEMS

TECHNICAL FIELD

The present disclosure generally relates to apparatus, systems, and methods of delivering medical fluid to patients, and more particularly to infusion pumps, disposable cassettes, and associated methods.

BACKGROUND

Infusion pumps are medical devices that may be used to administer intravenous (IV) fluids. An infusion pump can facilitate the delivery of IV fluids while controlling the volumes and rates for the delivery of such IV fluids. The IV fluids may be delivered at continuous rates or intermittent intervals. Some infusion pumps move fluid through an IV tube using a peristaltic pumping mechanism that acts on the IV tube, while other infusion pumps rely on a cartridge or cassette-like device intended to be manipulated by a pump to cause the IV fluid to flow at the controlled rate or interval. In either case, a typical infusion pump, manipulates the IV tube or IV cartridge such that the IV fluid moves from a container to a patient. The IV tube or IV cartridge is typically connected to or integrated with an IV set (e.g., tubing, valves, and fittings for delivering fluid to a patient), and therefore the cartridge and IV set may be disposable to reduce the risk of infection and contamination.

SUMMARY

Aspects of the subject technology relate to disposable IV pump cassettes and infusion pump systems. In accordance with certain aspects, a pump cassette may comprise a rigid body comprising a frame portion, a base portion, a compliant membrane disposed substantially therebetween, two opposing edge sections, and an interface-facing surface, wherein the rigid body comprises a positioning feature arranged substantially orthogonal to a general plane of the interface-facing surface; and a slider coupled to the two opposing edge sections and longitudinally articulable with respect to the rigid body.

In accordance with certain aspects, a pump cassette may comprise a rigid body comprising a compliant membrane, two opposing edge sections, and an interface-facing surface, wherein the rigid body comprises a controllable fluid pathway including a pump chamber, the controllable fluid pathway defined in part by the compliant membrane and extending from an inlet port to an outlet port; a pump assembly including a pump drive mechanism operably accessible from the interface-facing surface, wherein the pump drive mechanism is longitudinally articulable with respect to the rigid body; and a slider coupled to the two opposing edge sections and longitudinally articulable with respect to the rigid body.

In accordance with certain aspects, an infusion pump system may comprise a processing unit; a cassette recess configured to receive a pump cassette, the cassette recess comprising (i) a plurality of cassette engagement slots configured for removably coupling the pump cassette, and (ii) a cassette-facing surface comprising a positioning feature slot extending orthogonal to a general plane of the cassette-facing surface.

It is understood that in accordance with certain aspects, the cassette recess may be integrated into the same box as the processing unit or may be contained in an interface module that may be operatively coupled to the processing unit.

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings:

FIGS. 12A and 12B illustrate perspective views of examples of a fifth embodiment disposable IV pump cassette and cassette recess, in accordance with aspects of the present disclosure.

DETAILED DESCRIPTION

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions may be provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

Figure 1A:
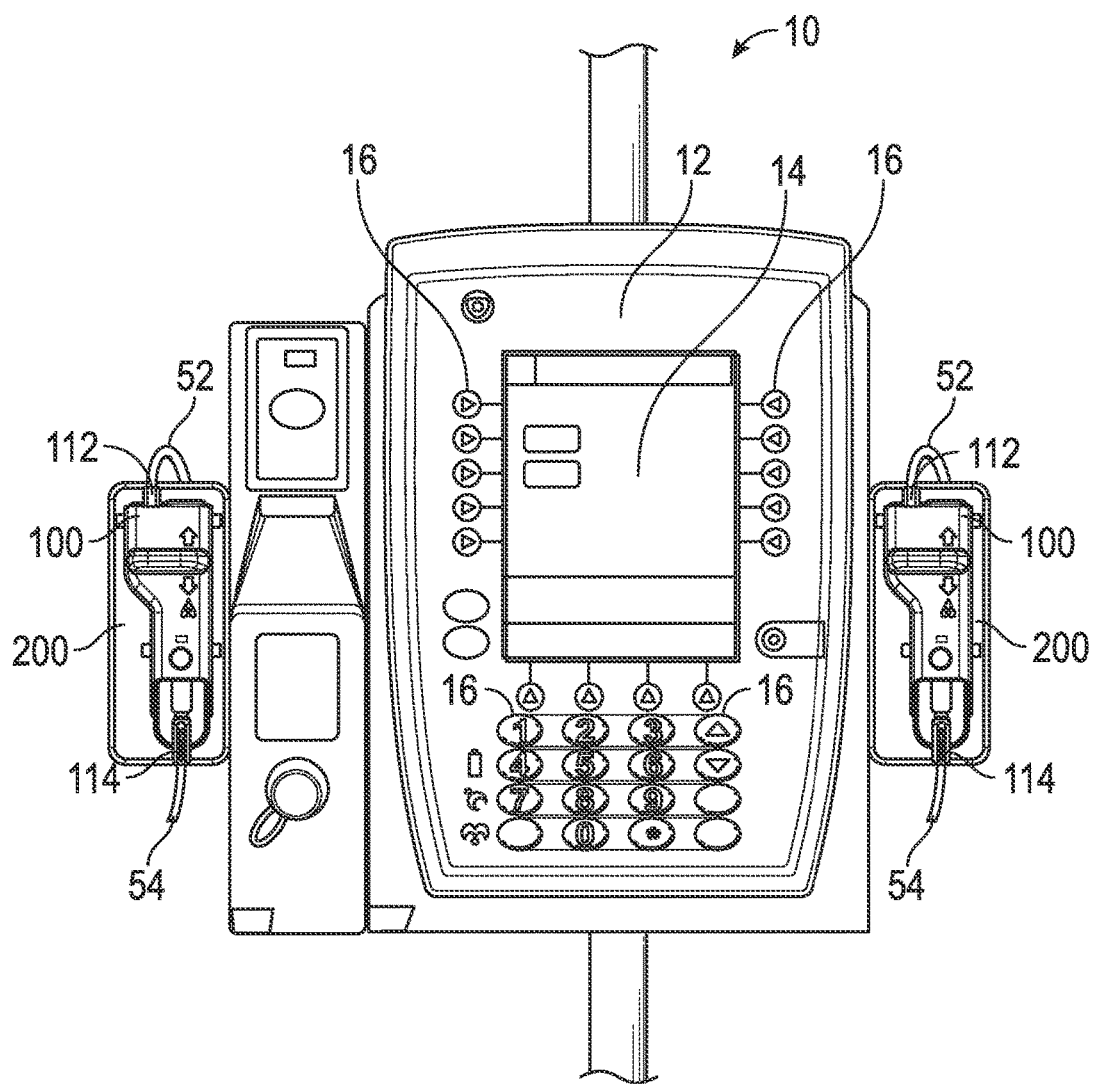
FIGS. 1A and 1B are overview diagrams illustrating examples of infusion pump systems, in accordance with aspects of the present disclosure.

FIG. 1A illustrates an example of an infusion pump system. In accordance with certain embodiments, infusion pump system 10 may include one or more cassette recesses and disposable IV pump cassettes (e.g., cassette recesses 200, 400, 600 and cassettes 100, 300, and 500). For example, cassette recess 200 may be configured to receive cassette 100 and provide various mechanical couplings and operational interfaces (e.g., fittings, motor, gearing, driveshaft, sensors, etc.). Infusion pump system 10 may include central processing unit 12 with display screen 14 (e.g., touchscreen display), and a data input features 16, for example, a keypad and a series of configurable buttons adjacent to display screen 14. Other types of input and output devices may be used with central processing unit 12 and infusion pump system 10. In certain aspects, central processing unit 12 is operatively coupled to one or more interface modules, with cassette recesses 200, to control and communicate with various operational interfaces thereof.

Figure 1B:
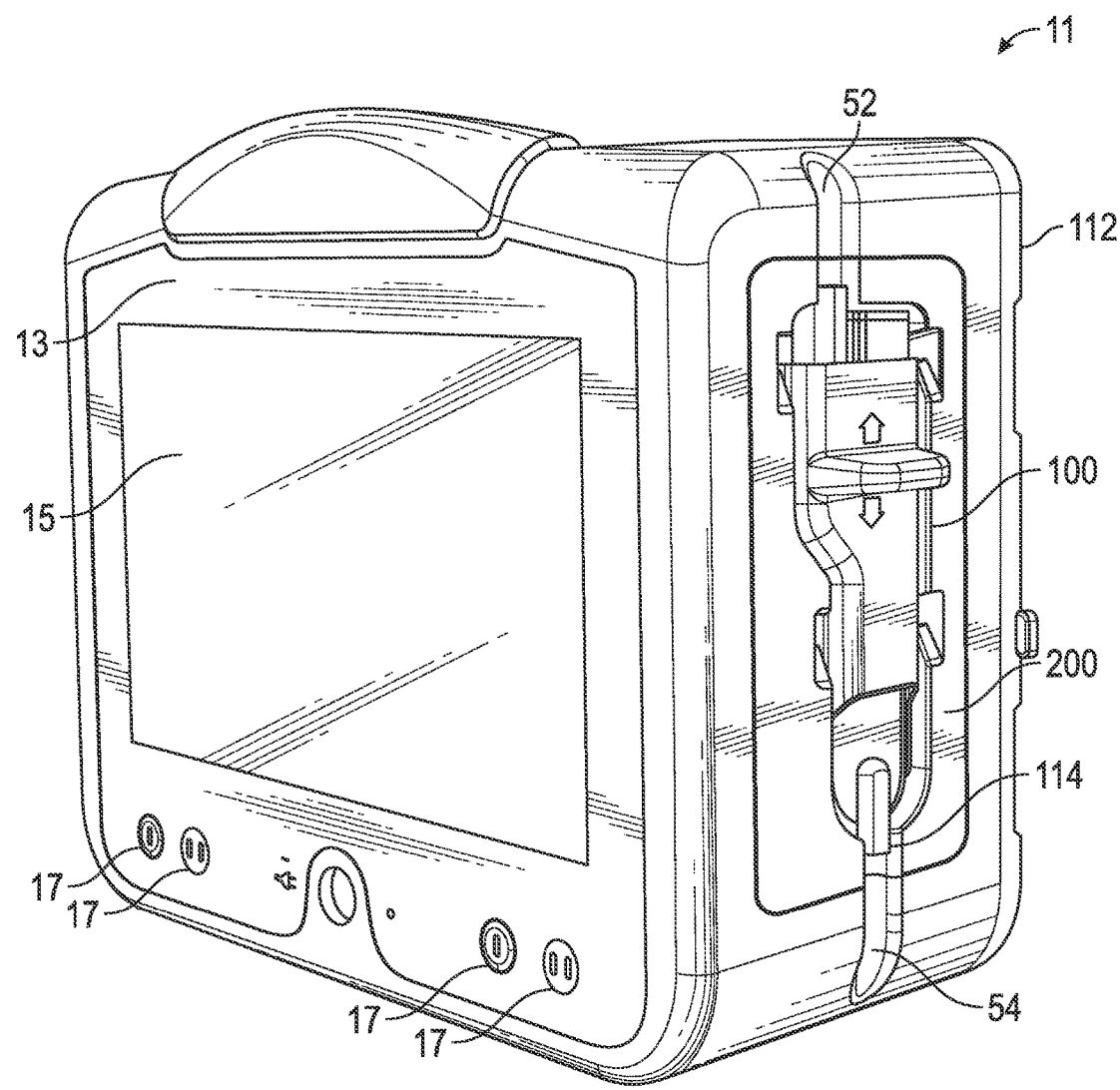

FIG. 1B illustrates another example of an infusion pump system. In accordance with certain embodiments, infusion pump system 11 may include one or more cassette recesses and disposable IV pump cassettes (e.g., cassette recesses 200, 400, 600 and cassettes 100, 300, and 500). For example, cassette recess 200 may be configured to receive cassette 100 and provide various mechanical couplings and operational interfaces (e.g., fittings, motor, gearing, driveshaft, sensors, etc.). Infusion pump system 11 may include central processing unit 13 with display screen 15 (e.g., touchscreen display), and a data input features 17, for example, a series of configurable buttons adjacent to display screen 15. In some implementations, the display screen 15 may provide a keypad or similar data entry feature. Other types of input and output devices may be used with central processing unit 13 and infusion pump system 11. In certain aspects, central processing unit 13 is operatively coupled to one or more interface modules, with cassette recesses 200, to control and communicate with various operational interfaces thereof.

In operation, an IV bag, syringe or other fluid source 52 may be fluidly connected to inlet 112 of cassette 100, and outlet 114 of cassette 100 may be fluidly connected to a patient 54 as shown in the examples of FIGS. 1A and 1B. Infusion pump systems 10 and 11 may be configured to operate over a wide range of infusion rates such as, but not limited to, 1-999 ml/h for general purpose and operating room applications, and 0.1-99.9 ml/h for neonatal applications. Infusion pump systems 10 and 11 may include, for example, low-sorbing configurations compatible with chemotherapy, TPN and Nitroglycerin (NTG). In accordance with some embodiments, cassettes 100 may comprise a DEHP-free and Latex fluid pathway suitable for various patient populations (e.g., neonate, pediatric, and adult).

In accordance with aspects of the subject technology, disposable IV cassettes 100 used with infusion pump systems 10 and 11 may be substantially reduced in size when compared to conventional disposable IV cassette units resulting in a significant amount of medical plastic required to be treated and disposed of in compliance with various regulations.

Additionally, infusion pump systems 10 and 11 comprising externally mounted and translucent cassettes 100 for which fluid passage through the entire fluid pathway, or a portion thereof, in the IV set may be advantageous.

In operation, a user (e.g., a caregiver) may obtain a new disposable IV cassette 100 and prime cassette 100 before inserting cassette 100 into cassette recess 200. Caregiver may check for any visible air bubbles in the fluid pathway and may press on any accessible fluid reservoirs (e.g., pressure dome chambers) to move fluid through the cassette 100. In accordance with certain aspects, cassette 100 can be securely held and inserted into cassette recess 200 by a single hand of a caregiver. In this regard, caregiver's other hand can be freed to perform other tasks.

Figures 2A, 2B:
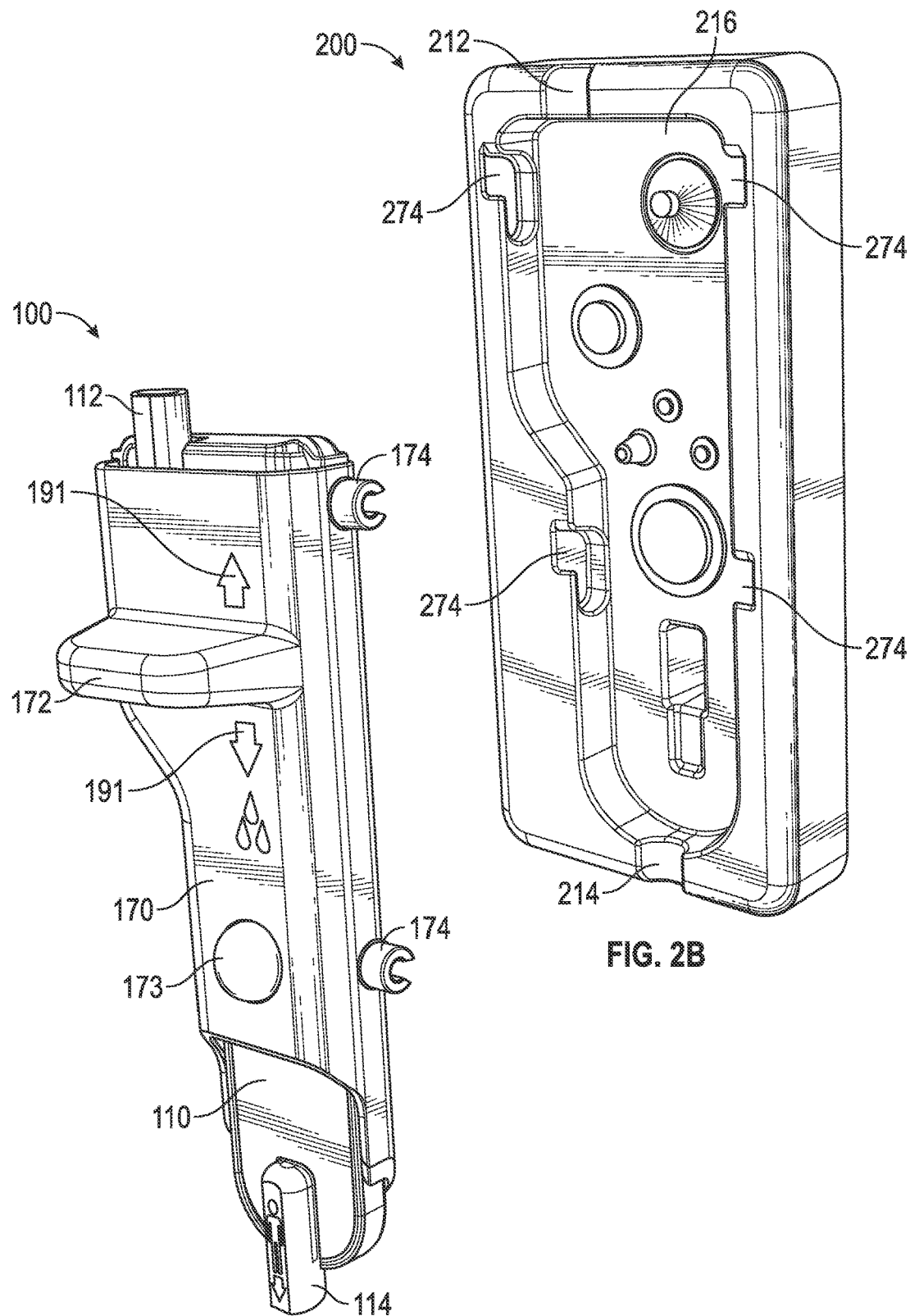
FIGS. 2A and 2B illustrate perspective views of examples of a first embodiment disposable IV pump cassette and cassette recess, in accordance with aspects of the present disclosure.

FIGS. 2A and 2B illustrate examples of a disposable IV pump cassette 100 and corresponding cassette recess 200 of an interface module. In accordance with certain embodiments, cassette 100 may comprise a cassette body 110 and a slider 170. Cassette 100 may include certain may include certain visual indicators related to operation aspects of the cassette and the infusion pump system in general. For example, cassette may include identifiable images such as fluid drops indicating position of slider 170 for free-flow (flow stop valve 164 in an open position) and a patient figure proximal to outlet 114. In accordance with some aspects, cassette 100 may include lens area 173 for magnification of the fluid pathway within the cassette body 110. Lens area 173 may be disposed on the slider 170 or proximal to outlet 114 and/or an air-in-line detection feature. For example, during priming or prepping a cassette, a user or caregiver may use lens area 173 to ensure that any visible air bubbles have been removed and fluid is flowing properly. In accordance with some aspects, one or more cassette-seated sensors may be disposed within the cassette recess 200 so as to inform central processing unit 12 that the cassette is locked or secured into place within the cassette recess 200 or seat.

Slider 170 can be fixably and slidably engaged with cassette body 110 such that slider 170 may articulate longitudinally 191 with respect to cassette body 110, but will be constrained within range of sliding motion such that the slider remains coupled to the cassette body 110. Slider 170 may be formed from rigid plastic or polymer material having lubricating characteristics (e.g., incorporating silicon or polytetrafluoroethylene (PTFE) additives), and is clear or translucent in accordance with certain embodiments. In some embodiments, slider 170 may be polycarbonate. Slider 170 includes a slider grip 172 or handle portion and a plurality of protrusions 174 or lugs that are configured to be releasably lockable with a plurality of slots 274 of the cassette recess 200 (e.g., L-shaped locking channels). In this regard, cassette 100 can be self-latched into the cassette recess 200. Accordingly, a door or lever action is not required in order to retain the cassette 100 within the cassette recess 200. In an alternative embodiment, an inverse configuration may be desired, in which the cassette recess 200 would contain protrusions or lugs that would be configured to be releasably lockable with a corresponding slots located on the slider or rigid body.

Figure 2C:
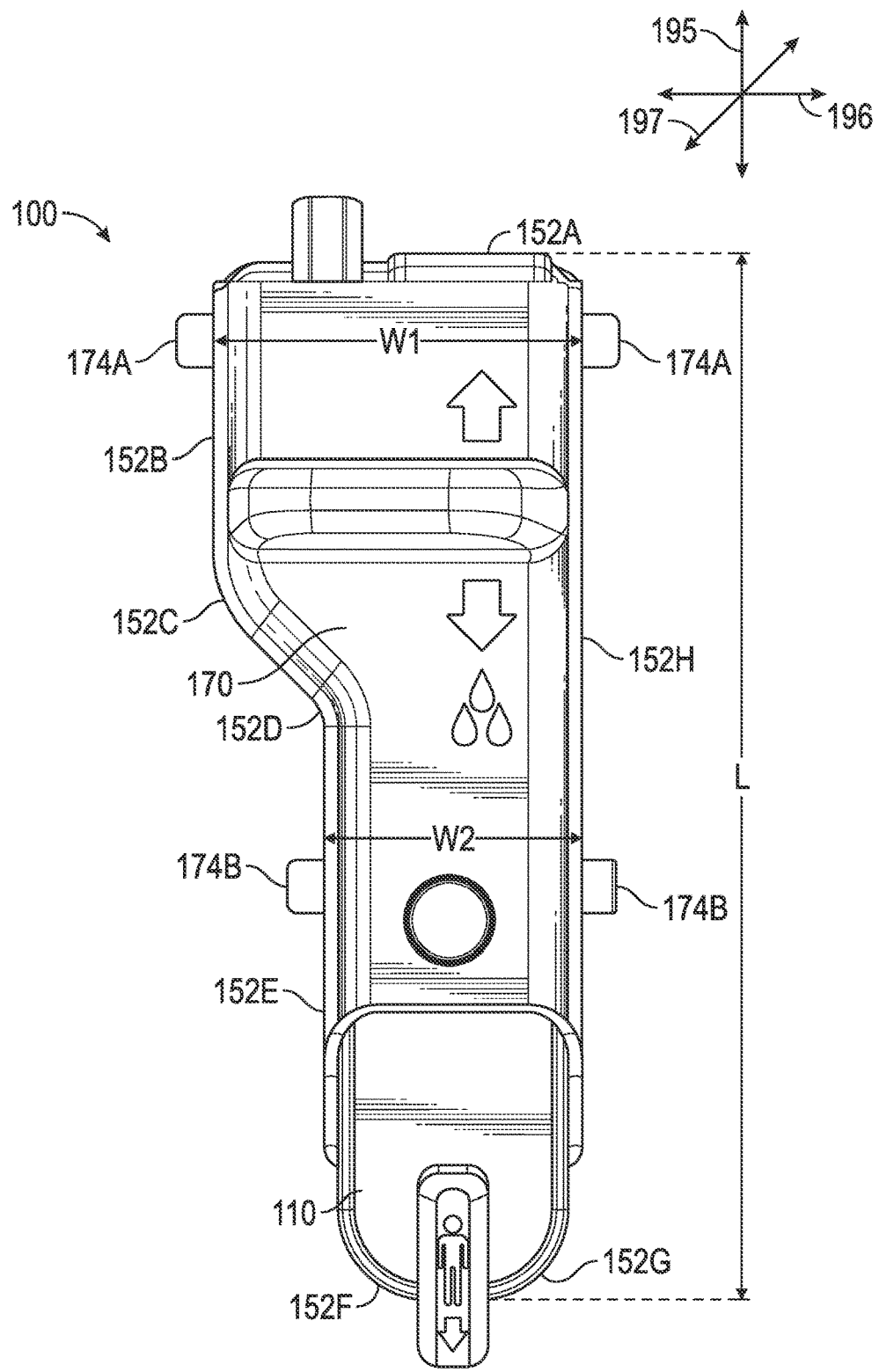
FIG. 2C illustrates a front perspective view of an example of a first embodiment disposable IV pump cassette, in accordance with aspects of the present disclosure.

The plurality of protrusions 174 may be disposed at various locations on slider 170. As illustrated in the example of FIG. 2C, slider 170 may comprise a first pair of protrusions 174a and a second pair of protrusions 174b. The first pair of protrusions 174a may be spaced apart a different distance (e.g., width W1) than the second pair of protrusions 174b (e.g., width W2). For example, in certain aspects, W1 may be between 31 mm and 35 mm, and W2 may be between 21 mm and 25 mm. In this regard, cassette 100 orientation within cassette recess 200 (along with non-vertically aligned inlet recess 212 and outlet recess 214) is clear to a user or caregiver such that a cassette 100 is not inadvertently installed (or when being primed) in an inverted manner.

Figure 2D:
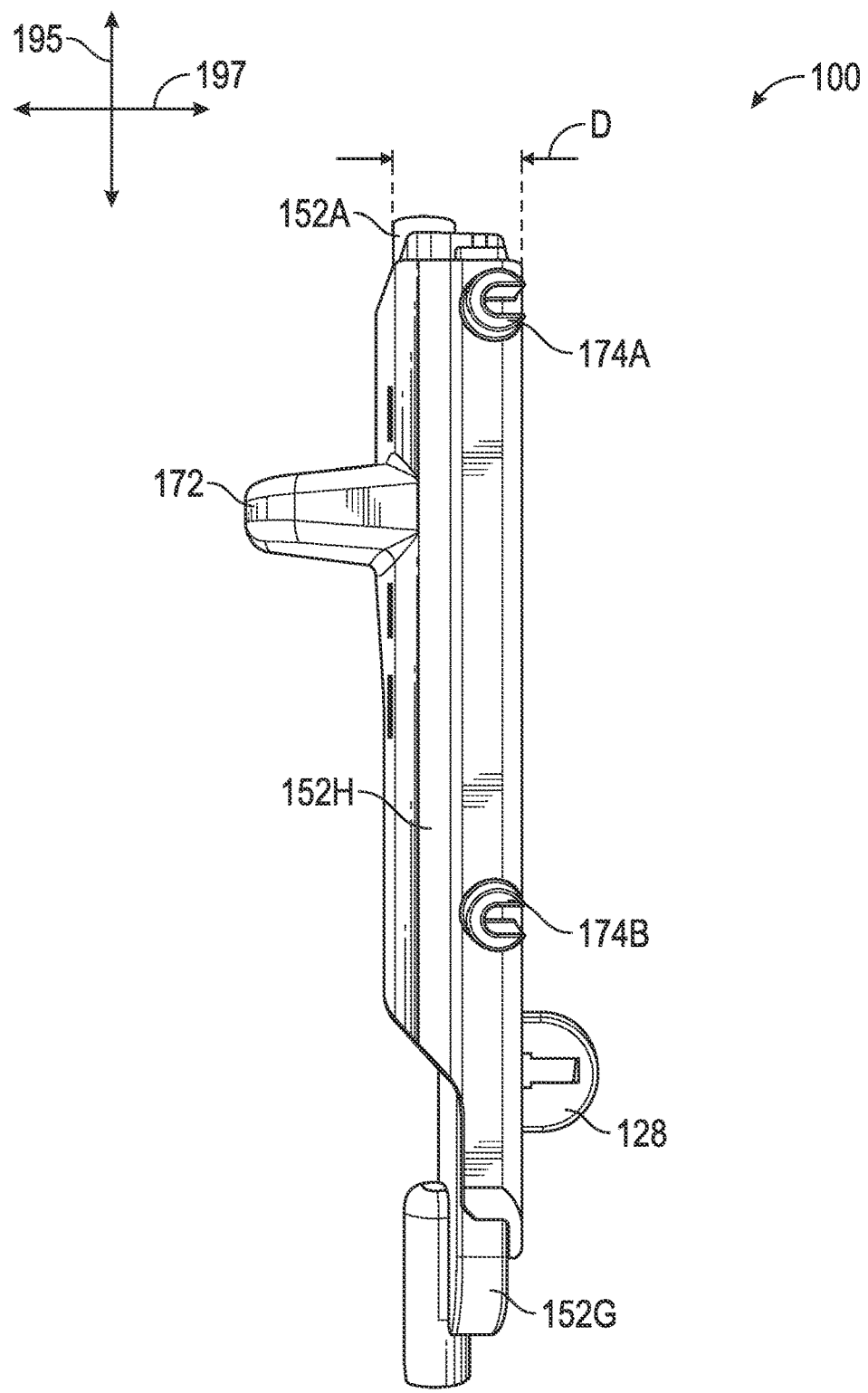
FIG. 2D illustrates a side perspective view of an example of a first embodiment disposable IV pump cassette, in accordance with aspects of the present disclosure.

Additionally, perimeter edges 152 of cassette 100 and corresponding perimeter edges of cassette recess 200 may include a plurality of arcuate perimeter edges for engagement between cassette 100 and cassette recess 200. For example, the plurality of arcuate perimeter edges may correspond to a perimeter opening of cassette recess 200 for front-loading cassette 100 into cassette recess 200. With reference to FIGS. 2C and 2D, cassette body 110 (with or without slider 170) may comprise top lateral edge 152a, straight longitudinal edge 152b, arcuate side edge 152c, arcuate side edge 152d, straight longitudinal edge 152e, bottom arcuate edge 152f, bottom arcuate edge 152g, and straight longitudinal edge 152h. Straight longitudinal edge 152b, straight longitudinal edge 152e, and straight longitudinal edge 152h may all be parallel and/or opposing edges to each other, in accordance with certain example aspects.

Arcuate side edge 152c, bottom arcuate edge 152f, and bottom arcuate edge 152g may be concave curved edges with respect to a general center portion of cassette 100 (e.g., pump chamber, valve, and positioning features), whereas arcuate side edge 152d is a convex curved edge with respect to a general center portion of cassette 100. Additionally, cassette 100 may include corner edges where two straight edges converge. For example, corner edges may be defined where top lateral edge 152a and straight longitudinal edge 152b meet, as well as where top lateral edge 152a and straight longitudinal edge 152h meet. Corner edges may be slightly rounded at the point of intersection in some implementations, but not considered arcuate with respect to defining an arcuate edge portion or section of cassette 100 (or cassette recess 200) for front-loading features described herein. Moreover, the arcuate edges on cassette 100 may have different curvatures, for example, different arc lengths, gradients, etc., such that an arcuate edge may be distinguishable from other arcuate edges curved edges as well as rounded corner edges. In other embodiments, perimeter edges 152 of cassette 100 may include a configuration of straight-line edges. In still other embodiments, one or more of the corner edges may be rounded sufficiently to be considered arcuate with respect to defining an arcuate edge portion or section of the cassette 100 (or cassette recess 200) for front-loading features described herein.

Without being limited to the specific embodiments described above, generally the arcuate edges of the cassette 100 provide a benefit by enabling visual identification as well as prohibiting improper orientation or seating of cassette 100 with a corresponding cassette recess 200. Additionally, minimizing a size of cassette 100 and optimizing a surface area of one or more corresponding cassette recess 200 may be achieved using arcuate perimeter edge configurations.

Additionally, an overall size of cassette 100 and cassette recess 200 may be reduced, in accordance with some aspects. For example, in certain embodiments, cassette body 110 may extended longitudinally a length (L) between 90 mm and 100 mm. In this regard, cassette body 110 may be dimensioned as having a first body section of a first width and a second body section of a second width. The first body section may have a wider width than the second body section, and the second body section may have a longer length than the first body section. For orientation reference with respect to the various views of the examples illustrated of FIGS. 2C-2F, longitudinal axis or y-axis 195, latitudinal axis or x-axis 196, and depth axis or z-axis 197 are provided.

In this regard, depth aspects of cassette 100 is shown in the example of FIG. 2D. For example, in certain embodiments, cassette body 110, or a substantial portion thereof, may extend depth (D) between 6 mm and 8 mm. Fluid pathway extension member 128 may further extend between 8 mm to 10 mm. In certain aspects, slider grip 172 may extend between 10 mm to 14 mm from cassette body 110. It is to be appreciated that the process of cleaning of inlet recess 212, outlet recess 214, and cassette recess 200 is made efficient in the shallow recess configuration in accordance with certain embodiments should any fluid or debris accumulate within cassette recess 200. The shallow recess configuration of cassette recess 200, and associated longitudinal alignment of cassette 100 such that a smaller of volumetric dimensions of cassette 100 (e.g., depth being smaller than length and width in certain embodiments) further enables additional space for arrangement of mechanical couplings and operational interfaces and optimizes the overall space requirements of cassette recess 200 and infusion pump system in general.

Figure 2E:
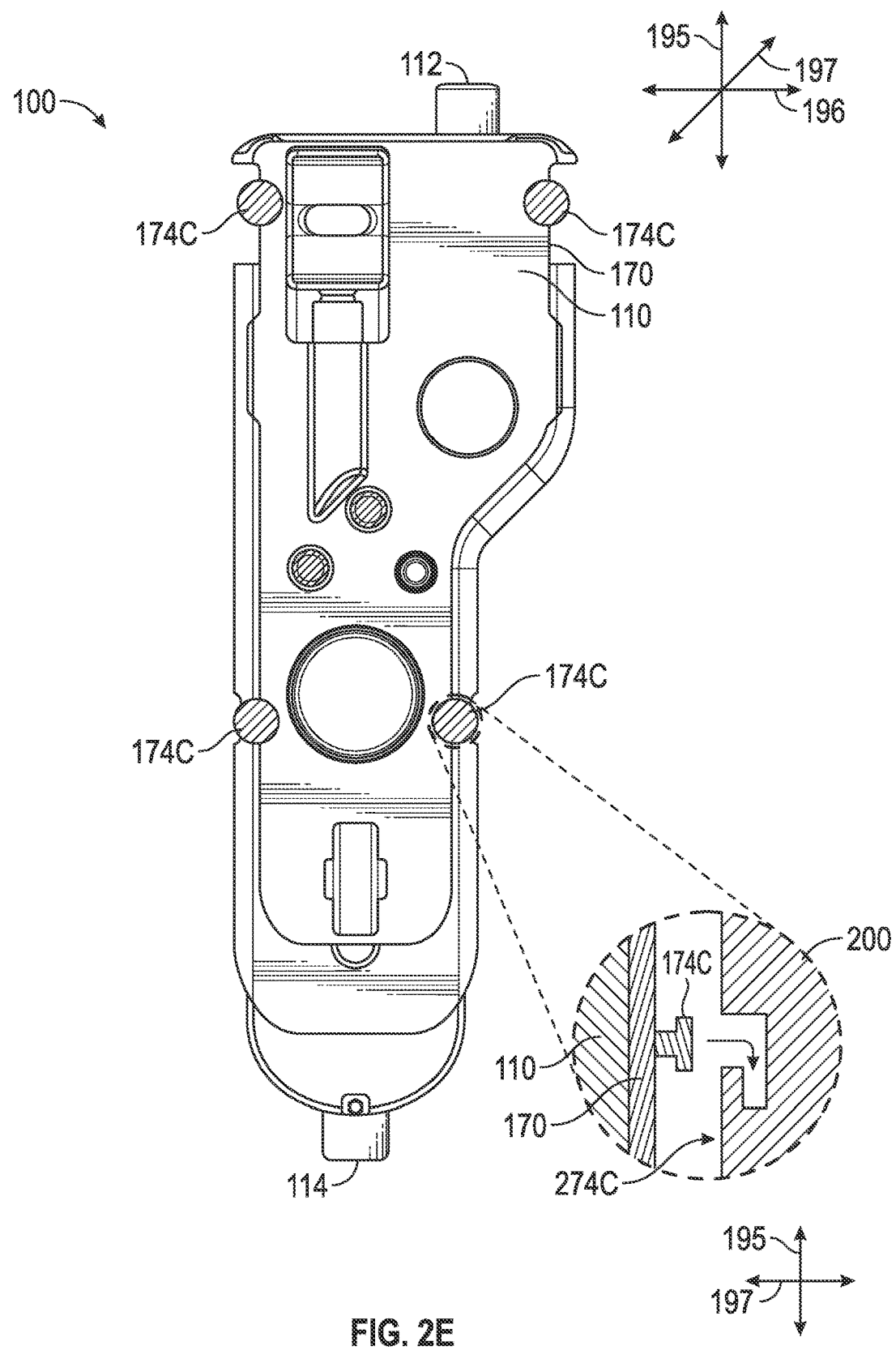
FIG. 2E illustrates a rear perspective view of an example of a variation of a first embodiment disposable IV pump cassette including a detail section (Detail A), in accordance with aspects of the present disclosure.

Various types, placement, and orientations of the plurality of protrusions 174 disposed on slider 170 are contemplated in the present disclosure. As illustrated in the example of FIG. 2E, plurality of protrusions 174c can protrude toward the cassette recess 200 (e.g., along z-axis 197), and be receivable by corresponding slots 274c configured to receive protrusion 174c. As shown in Detail A of FIG. 2E, protrusion 174c can be aligned and inserted into an opening of slot 274c having a circular cross-section with a lower slit of reduced diameter than the circular cross-section (e.g., keyhole latch design). Slider 170 may then be articulated downwardly when a head portion of protrusion 174c is aligned with an internal longitudinal channel of slot 274c and a neck portion of protrusion 174c is aligned with the lower slit of slot 274c. The present disclosure contemplates protrusions 174 of any size or shape on the outward edges of slider 170 so long as the corresponding slots 274 are of matching dimensions and can serve to latch or cassette 100 in the cassette recess 200 through the movement of the slider 170 from an disengaged to engaged position.

Figure 2F:
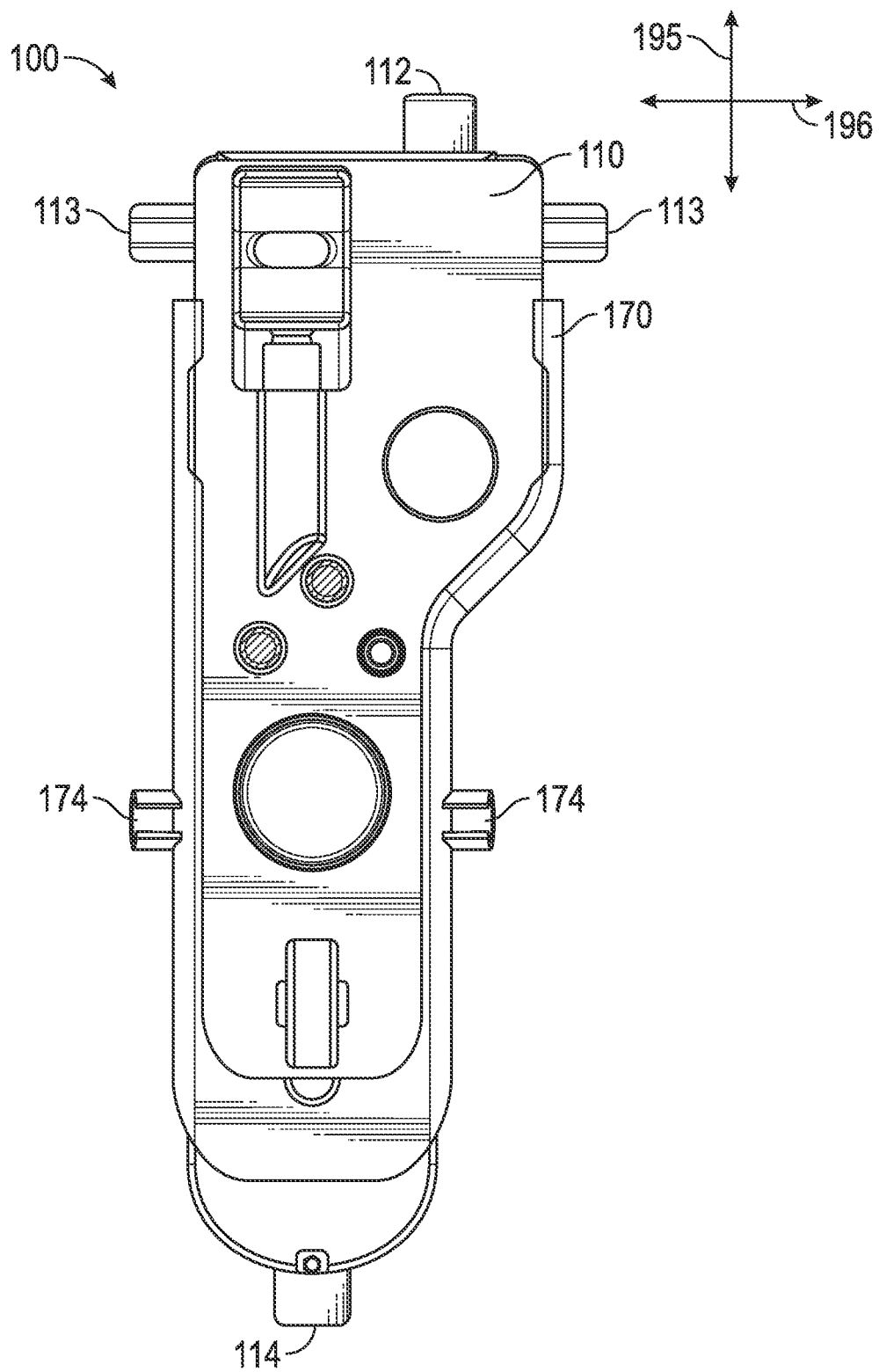
FIG. 2F illustrates a rear perspective view of an example of a variation a first embodiment disposable IV pump cassette, in accordance with aspects of the present disclosure.

As illustrated in the example of FIG. 2F, cassette 100 may be configured with one or more protrusions 113 disposed on cassette body 110 and a plurality of protrusions 174 disposed on slider 170. The one or more cassette body protrusions 113 may engage with one or more corresponding upper slots 274 independently from the plurality of protrusions 174. In this regard, cassette 100 may be configured to hang or otherwise be securely positioned in cassette recess 200, without operatively engaging associated mechanical couplings and operational interfaces of cassette recess 200. When cassette 100 is to become operational, cassette 100 may be pivoted (or removed and reinserted), for example, such that protrusions 174 securely engage with the lower slots 274 of cassette recess 200.

In accordance with other embodiments, cassette 100 may be coupled to cassette recess 200 by the one or more protrusions 113 and not necessarily comprise a slider mechanism. For example, a grip section may be disposed on cassette body 110 and the one or more protrusions 113 may be configured to engage with and securely latch to one or more slots 274 of the cassette recess 200.

In other embodiments, a single protrusion or latch disposed on one of cassette 100 or slider 170 may be utilized to couple with cassette recess 200. Aspects of the various cassette-coupling techniques illustrated in the examples of FIGS. 2C-2F and described herein may be further combined and arranged into additional configurations suitable for specific implementations given the benefit of the present disclosure.

Moreover, in accordance with certain aspects, features of cassette recess 200 are designed to avoid wear down and/or risk of malfunction. For example, the plurality of slots 274 arranged within cassette recess 200 may be devoid of any movable latching mechanism in certain embodiments as such movable latching mechanisms may be susceptible to excessive wear and mechanical failure over repeated use with multiple disposable IV cassettes 100.

In operation, cassette 100 can be loaded directly into cassette recess 200. In this regard, the direct loading of the cassette 100 will enable avoidance of sheer forces that might otherwise be applied to the sensors, alignment features, and other engaging interfaces of cassette-facing surface 216 of cassette recess 200 from interaction with the interface-facing side of cassette body 110 as it is loaded into cassette recess 200.

It is to be understood that modification to the various features of cassette 100 can be made to accommodate the various cassette-coupling techniques disclosed herein.

Figure 3A:
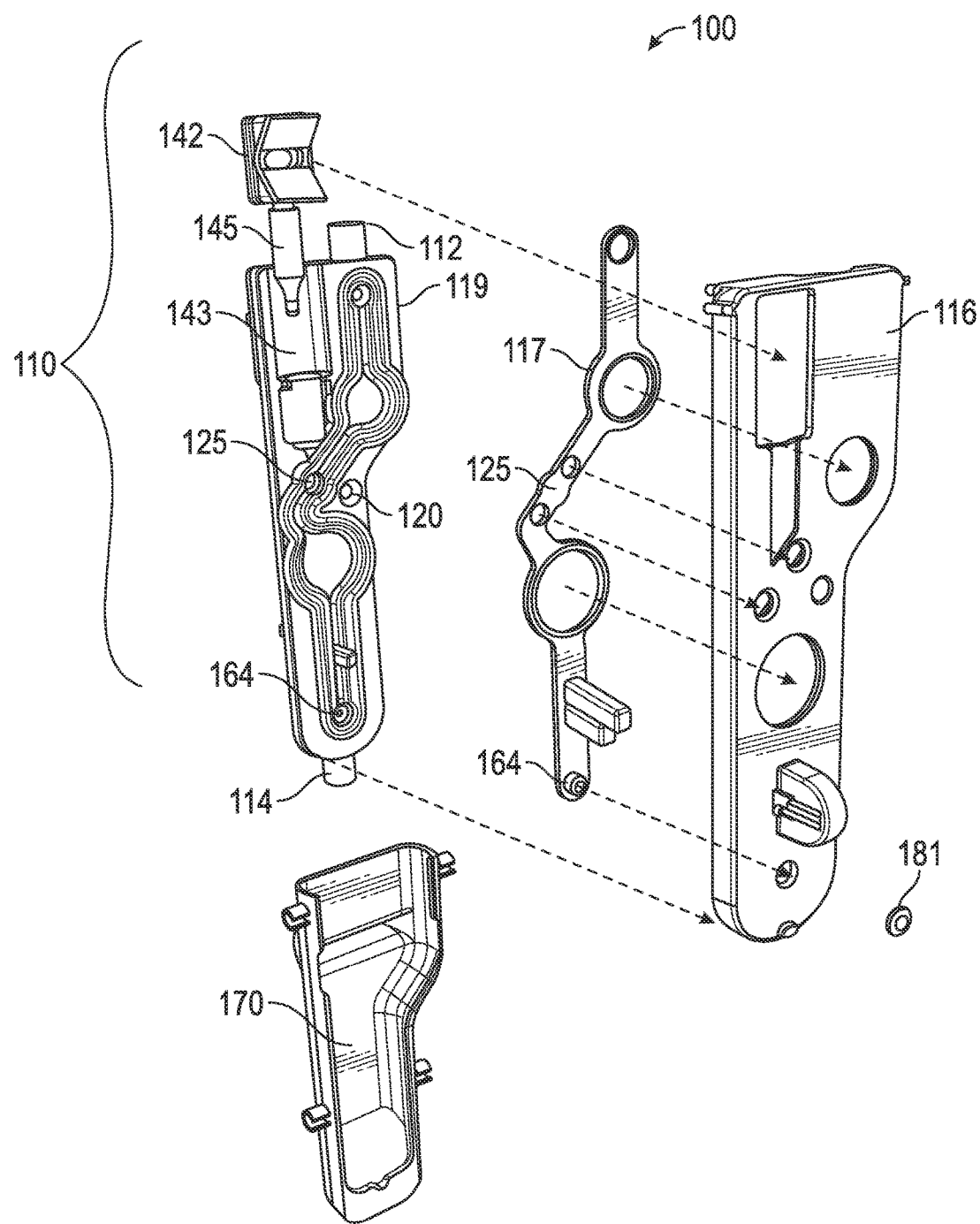
FIG. 3A is an exploded perspective detail view illustrating an example of a first embodiment disposable IV pump cassette, in accordance with aspects of the present disclosure.
Figure 3B:
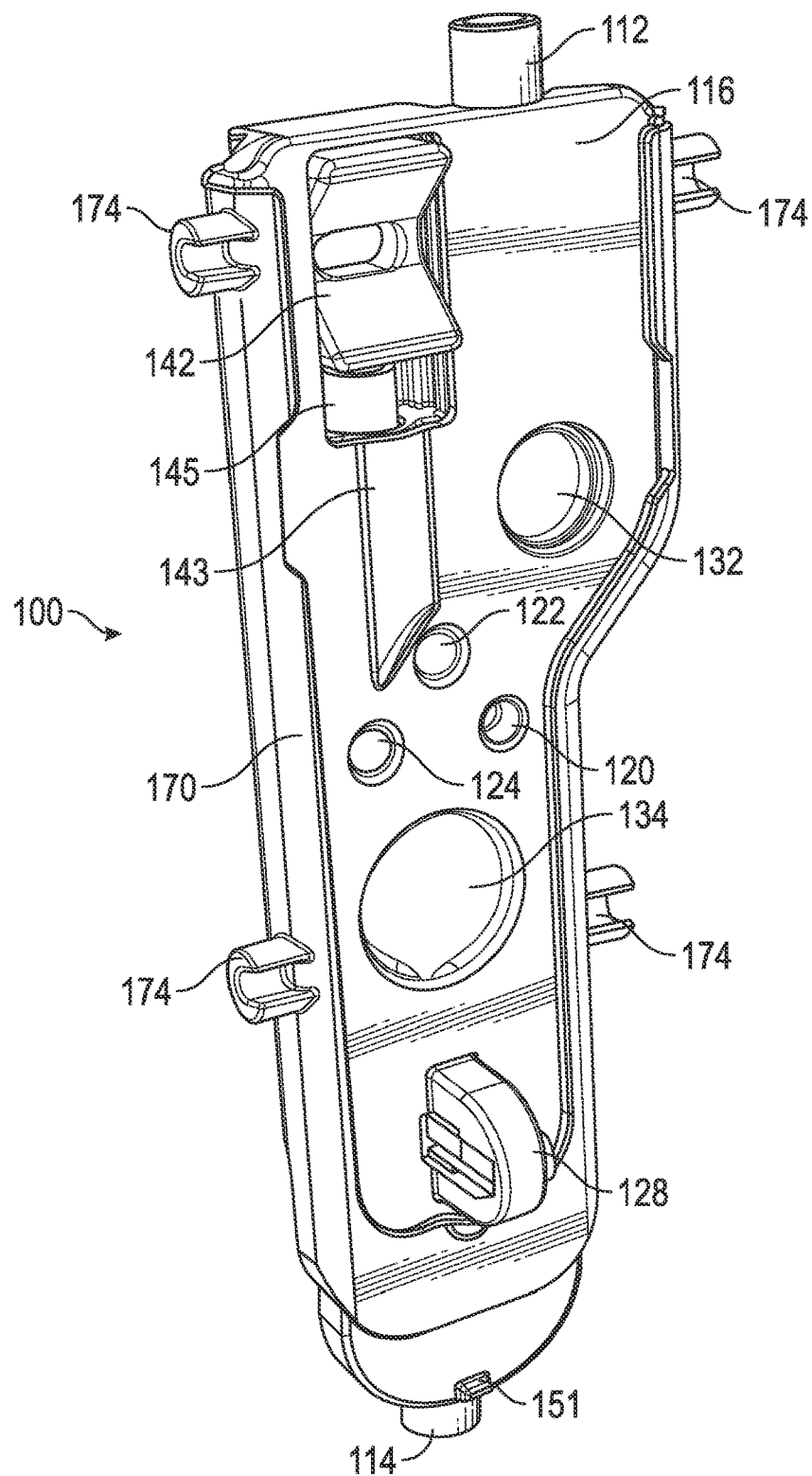
FIG. 3B illustrates a perspective view of an example of a first embodiment disposable IV pump cassette, in accordance with aspects of the present disclosure.

Referring now to the examples of FIGS. 3A and 3B, cassette body 110 may comprise interface-facing frame portion 116 and slider-facing base portion 119 with membrane 117 disposed substantially therebetween (e.g., portions of membrane 117 may extend through some openings of frame portion 116). In accordance with certain embodiments, membrane 117 can be a compliant material co-molded to the frame portion 116 and sealingly engaged with base portion 119 for defining a fluid pathway through cassette body 110 from inlet 112 to outlet 114. Mating edges of frame portion 116 and base portion 119 may be connected by fusing, welding, gluing, or the like. Membrane 117 and base portion 119 may further define a plurality of other features, some of which may be accessed through openings in frame portion 116.

Frame portion 116, membrane 117, and/or base portion 119 may define features in or along the fluid pathway, in accordance with certain embodiments. For example, beginning from inlet 112, the fluid pathway may include features such as, but not limited to, upstream pressure dome 132 (e.g., an inlet-side compliant reservoir), inlet-side valve 122, pump chamber having pump chamber opening/access 125, outlet-side valve 124, downstream pressure dome 134 (e.g., an outlet-side compliant reservoir), fluid pathway extension member 128, and flow stop valve 164. Other features that are not in or along the fluid pathway, but are disposed on cassette body 110, may include positioning port 120 and slider stopper 151. With respect to extension member 128, a portion of the fluid pathway can be extended away or protrude orthogonally from the generally flat and planar exterior surface of interface-facing frame portion 116 so as to make the fluid in the fluid pathway available for certain detection techniques performed by infusion pump system 10, 11. As illustrated in the example of FIGS. 3A and 3B, fluid pathway extension member 128 may be formed from orthogonally extending portions of frame portion 116, membrane 117, and/or base portion 119.

In accordance with certain embodiments, membrane 117 may be formed from a thermoplastic elastomer (TPE). Characteristics of certain TPEs can enable effective co-molding with other materials, for example, polycarbonate. Accordingly, in some embodiments, membrane 117 may be co-molded to frame portion 116 and striker 181 may be co-molded to a portion of membrane 117 defining a flow stop valve 164. However, in some embodiments, membrane 117 can be formed from silicon, a silicon-based compound, an elastomeric material suitably compliant for fluid flow, or the like.

In accordance with certain embodiments, interface-facing frame portion 116 and slider-facing base portion 119 may be formed from a rigid plastic such as, but not limited, a polycarbonate. Additionally, the rigid plastic of frame portion 116 and base portion 119 may be clear or translucent. The material of membrane 117 (e.g., TPE or other compliant material) and rigid plastic slider 170 may also be clear or translucent, thereby allowing a user or caregiver to readily observe fluid passage through a substantial portion of the fluid pathway of cassette body 110. In some embodiments, the fluid pathway portion of cassette body 110 will be clear or translucent, and other portions will be frosted so as to direct a user or caregiver's attention to the fluid pathway.

In some implementations, slider 170, base portion 119, and membrane 117 may be clear or translucent (or at least some portions along the fluid pathway), and the frame portion 116 may not be translucent. For example, the frame portion 116 may be colored in a manner so as to contrast against a color or tint of the fluid expected to be used with cassette 100. In some embodiments, a lens area 173 may be disposed on base portion 119 alternatively, or in addition to, lens area 173 disposed on slider 170.

Figure 3C:
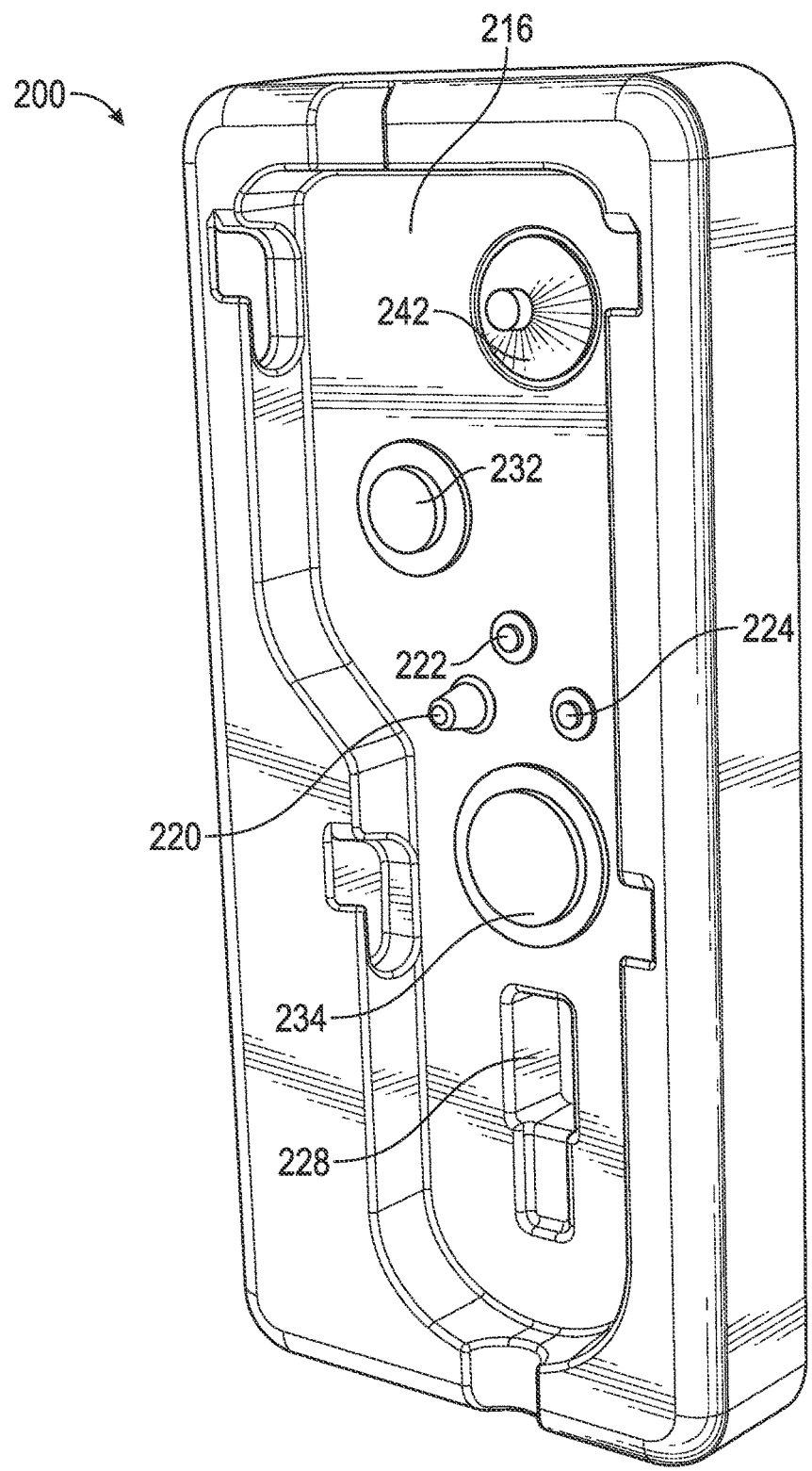
FIG. 3C illustrates a perspective view of an example of a first embodiment cassette recess, in accordance with aspects of the present disclosure.

With additional reference to the example of FIG. 3C, one or more fluid sensors may be disposed within sensor slot 228. The one or more fluid sensors disposed within sensor slot 228 can be ultrasonic sensors configured as an air-in-line detector, for example. In certain embodiments, extension member 128 may be disposed on cassette body 110 and positioned along the fluid pathway between downstream pressure dome 134 and flow stop valve 164. However, in some embodiments, extension member 128 can be positioned at other locations along the fluid pathway such as, but not limited to, between inlet 112 and upstream pressure dome 132. Additionally, in other embodiments, a plurality of extension members 128 with a plurality of corresponding sensor slots 228 may be positioned along a fluid pathway of cassette body 110.

As illustrated in the examples of FIG. 3A-3C, cassette body 110 may include a pump drive assembly in accordance with certain embodiments. For example, the pump drive assembly may include pump drive interface 142 for receiving pump actuator 242 of cassette recess 200. Pump drive interface 142 can be operatively coupled to piston 145 slidably engaged within piston guide 143 or casing (e.g., generally cylindrical or frustoconical casing) such that reciprocal movement of piston 145 moves within pump chamber providing a seal to urge fluid through the fluid pathway of cassette body 110. In this regard, the pump chamber may be defined by a portion of the piston guide 143 or casing distal from the pump drive interface 142 that is adjacent to and fluidly coupled with a tract or section of the fluid pathway between inlet-side valve 122 and outlet-side valve 124. Thus, pump chamber permits movement of the piston guide 143 with the reciprocal motion of the piston 145 such that a volume of the pump chamber may be varied by movement of the piston 145 in accordance with certain embodiments. In accordance with certain aspects, piston 145 resides and moves within a rigid bore and allows a seal that permits fluid to be drawn into the pump chamber via pump chamber opening/access 125 on the fill cycle and expelled on the delivery cycle.

A wiper seal (not shown) may be positioned within or proximal to piston guide 143 and slidably engaged with piston 145 thereby reducing the possibility of any substances (e.g., dirt or dried fluid particles) near the cassette 100 from contacting one or more slidable seals of the piston 145. The one or more slideable seals of the piston 145 may contact an internal wall piston guide 143 to form a movable barrier of the pump chamber. Additionally, piston 145 may include a reduced tip portion for more precise volumetric displacement of fluid into and out of pump chamber through pump chamber opening/access 125.

For example, pumping operation of infusion pump system 10, 11 when cassette 100 is primed and seated in cassette recess 200 may comprise activating outlet-side valve actuator 224 such that outlet-side valve 124 is closed or sealed while activating inlet-side valve actuator 222 such that inlet-side valve 122 is opened. Opening of inlet-side valve 122 may coincide with or occur shortly before the start of a reverse stroke of piston 145 (e.g., a movement of piston 145 away from pump chamber). Accordingly, fluid can flow from upstream pressure dome 132 to pump chamber. Alternatively, or in addition to, outlet-side valve 124 may comprise a one-way valve mechanism that permits flow of fluid under normal conditions in one direction (from a fluid container to a patient). Additionally, in some alternative embodiments, inlet-side valve 122 may also comprise a one-way valve or choke mechanism permitting flow of fluid in primarily one direction (e.g., from a fluid container to a patient) under normal operating conditions. In this configuration, cassette recess 200 may not need to incorporate either outlet-side valve actuator 224 or inlet-side valve actuator 222. Outlet-side valve 124 and inlet-side valve 122 may limit flow of fluid in one direction, but permit flow in an opposite direction in the event fluid pressure overcomes a cracking pressure of the valves.

Continuing with the valve-operated implementation, pumping operation may comprise activating outlet-side valve actuator 224 such that outlet-side valve 124 is open while activating inlet-side valve actuator 222 such that inlet-side valve 122 is closed or sealed. Opening of outlet-side valve 124 may coincide with or occur shortly before a start of a forward stroke of piston 145 (e.g., a movement of piston 145 toward the opening/access 125 of the pump chamber such that the volume of the pump chamber is reduced). Thus, fluid can flow from pump chamber down the fluid pathway to outlet 114.

In certain embodiments, the upstream pressure dome 132 may be smaller than the downstream pressure dome 134 to minimize retained volume. Likewise the downstream pressure dome 134 may be larger than the upstream pressure dome 132 to improve resolution of fluid pressure thereby allowing for an accurate and precise volume of fluid to be pumped and any upstream or downstream pressures to be accurately measured.

Figure 3D:
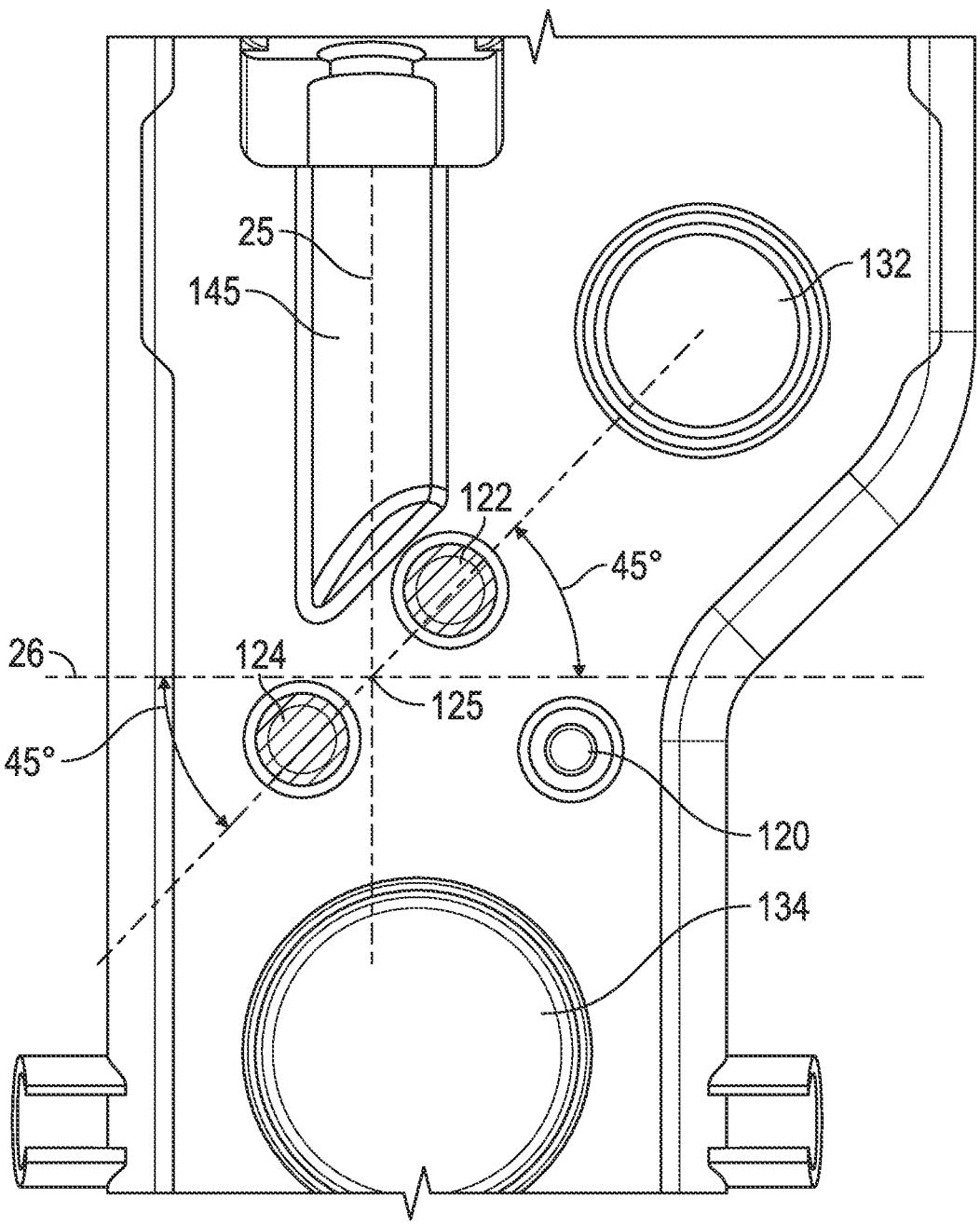
FIG. 3D illustrates an enlarged view of an example of a pump chamber area of a first embodiment disposable IV pump cassette, in accordance with aspects of the present disclosure.

As illustrated in the example of FIG. 3D, inlet-side valve 122 and outlet-side valve 124 may be positioned 180° away from each other for optimizing valve actuation mechanics. In certain embodiments, piston 145 is aligned below the opening of pump chamber and parallel to a longitudinal axis 25 of the general center of the pump chamber. In an alternate embodiment, piston 145 is aligned above the opening/access 125 of the pump chamber and parallel to a longitudinal axis 25 of the general center of pump chamber. It is to be appreciated that piston pump techniques can provide repeatedly precise positive displacement of fluid in the pump chamber. Moreover, piston pump techniques as described in the present disclosure may be readily adapted to be syringe pump embodiments.

Referring to FIGS. 3A-3C, pump drive interface 142 and pump actuator 242 may be configured as a reciprocating motion mechanism (e.g., a scotch-yoke configuration) in certain implementations. In such implementations, pump drive interface 142 may include opposing ramp portions for guiding a rotatable pin of pump actuator 242 toward an elongate slot of pump drive interface 142. For example, the outer edges of the opposing ramp portions may be arranged a distance that will ensure engagement with the rotatable pin of pump actuator 242. When the rotatable pin contacts one of the ramp portions, the pump drive interface 142 will move to align the elongate slot of pump drive interface 142 with the with the rotatable pin of pump actuator 242. However, it is to be appreciated that other pump drive assemblies are contemplated with cassette 100 and cassette recess 200 in accordance with the present disclosure.

For example, pump drive assembly may comprise an orthogonal pump drive mechanism whereby a pump actuator of an interface module applies a force orthogonal to a plane of interface-facing frame portion as described with respect to example cassette 500 and cassette recess 600 embodiments described herein.

In certain embodiments, cassette recess 200 may include an upstream pressure sensing probe 232 and downstream pressure sensing probe 234 enabling measurement of in-line pressure and fault isolation to a section of the fluid pathway. For example, upstream pressure sensing probe 232 may operably contact upstream pressure dome 132 through a corresponding opening of interface-facing frame portion 116. Similarly, downstream pressure sensing probe 234 may operably contact downstream pressure dome 134 through a corresponding opening of frame portion 116.

With reference to the examples of FIGS. 3B and 3C, the x-y positioning of cassette 100 within cassette recess 200 can be constrained by the positioning port 120 and positioning protrusion 220 mating interface, as well as fluid pathway extension member 128 and sensor slot 228 mating interface (e.g., air-in-line detector feature). In this regard, cassette 100 and cassette recess 200 can have two points of contact in the z-axis direction (e.g., an axis through and transverse to a general plane of the interface-facing surface of cassette body 110 of cassette 100 and cassette-facing surface of cassette recess 200) for interlock alignment of the cassette with respect to the x-y positioning of the interface side of the cassette body 110.

According to certain aspects, positioning port 120 may be located proximal to inlet-side valve 122 and outlet-side valve 124, and correspondingly mating positioning protrusion 220 may be located proximal to inlet-side valve actuator 222 and outlet-side valve actuator 224. In this regard, the cassette 100 may be positioned properly without over constraining the cassette 100.

In some embodiments, the latching engagement of slider 170 with cassette recess 200 may be less relevant to the x-y positioning in the cassette body 110 for properly aligning features on the interface-facing frame portion 116.

In other words, the controlling index for proper x-axis and y-axis alignment of the interface-facing frame portion 116 is the positioning port 120 and positioning protrusion 220 mating interface, in certain embodiments. In some embodiments, the positioning port 120 and positioning protrusion 220 mating interface, and fluid pathway extension member 128 and sensor slot 228 mating interface, together form the controlling index for proper x-axis and y-axis alignment of the interface-facing frame portion 116 (e.g., dual-feature x-y positioning scheme).

However, in certain embodiment, the latching engagement of slider 170 with cassette recess 200 provides tight tolerances for z-axis positioning of the cassette body 110 and corresponding interface-facing frame portion 116 for operation with the cassette-facing surface 216 of cassette recess 200 (e.g., z-axis alignment or distances require for proper operation of the pressure sensors as well as valve actuators). It is to be understood that techniques of z-axis alignment or depth other than slider protrusion 174 positioning are contemplated. For example, positioning protrusion or pin may include a locking or stabilizing feature (e.g., a transverse aperture or engagement flanges) that may be removably coupled with a corresponding receiving port feature or mechanism in either the cassette 100 or cassette recess 200. In other words, a snap engage type of component interfacing scheme.

It is to be understood that positioning protrusion 220 may have various cross sectional geometries in addition to the circular cross-section protrusion/pin-type illustrated in FIG. 3C and other figures. For example, pin may have a triangular, square, or other polygonal cross-section. For instance, a polygonal shape may be used to provide tighter tolerances to the x-y positioning of the cassette body 110 when cassette 100 has an air-in-line features the does not protrude into and received by cassette recess 200. Alternatively or in addition, the slider 170 may be configured have to tighter tolerances with respect to the x-axis and/or y-axis. For example, the x-axis tolerance may be substantially tight so as to avoid or substantially limit any minor or miniscule rotation of the cassette body 110 during prolonged continuous operation with infusion pump system 10, 11. Moreover, the positioning port 120 and positioning protrusion 220 mating interface can be reversed in some implementation (e.g., the positioning protrusion may be disposed on cassette 100).

However, in some implementations of cassette 100 and cassette recess 200, a dual-feature x-y positioning scheme as described herein can be advantageous so as to avoid too much stress on a single mating feature. For example, positioning protrusion 220 having a circular cross-section cooperatively engaging with positioning port 120 can provide tight tolerances for either the x-axis or y-axis alignment of interface-facing frame portion 116, but not necessarily both x-axis or y-axis alignment as rotation between positioning protrusion 220 and positioning port 120 can occur. However, in conjunction with a second x-y positioning such as fluid pathway extension member 128 and sensor slot 228 mating interface, tight tolerances can be achieved without undue stress on either of the x-y positioning features, as well as the cassette 100 and cassette recess 200 in general.

Accordingly, advantages of the x-y positioning schemes disclosed herein include, but are not limited to, preventing sheering to sensor features (e.g., upstream pressure sensing probe 232 and downstream pressure sensing probe 234 may not engage with sensors until they are properly aligned by the x-y positioning features, aiding in full and proper valve operation (e.g., inlet-side valve actuator 222 and outlet-side valve actuator 224 may not fully close a corresponding valve if misaligned on the x-axis and/or y-axis occurs), and assisting with communicating a correct timing for latching slider 170 of cassette 100 with cassette recess 200 (e.g., caregiver can sense engagement of x-y positioning features between cassette 100 and cassette recess 200).

Figure 4A:
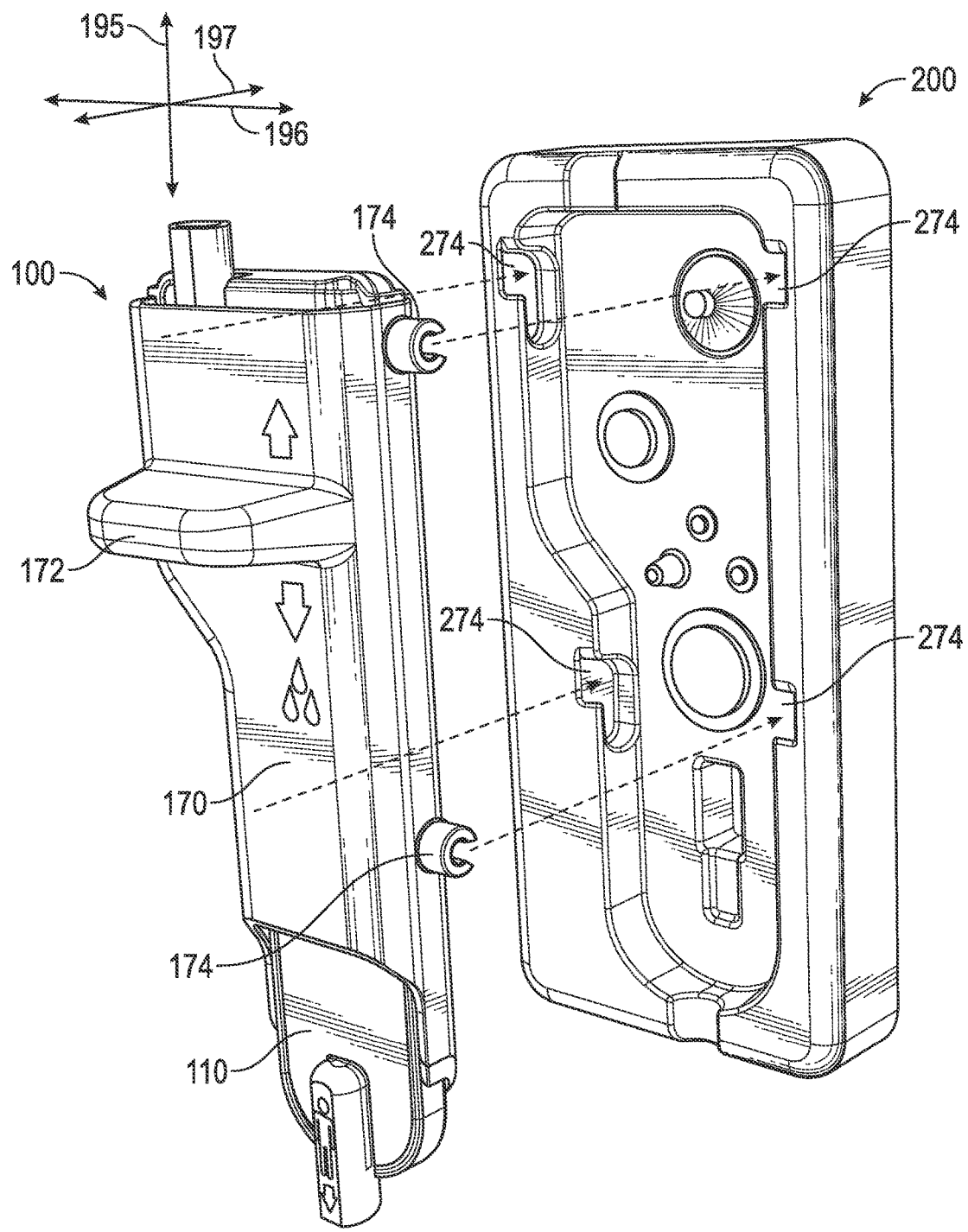
FIG. 4A illustrates perspective views of examples of a first embodiment disposable IV pump cassette and cassette recess, in accordance with aspects of the present disclosure.
Figure 4B:
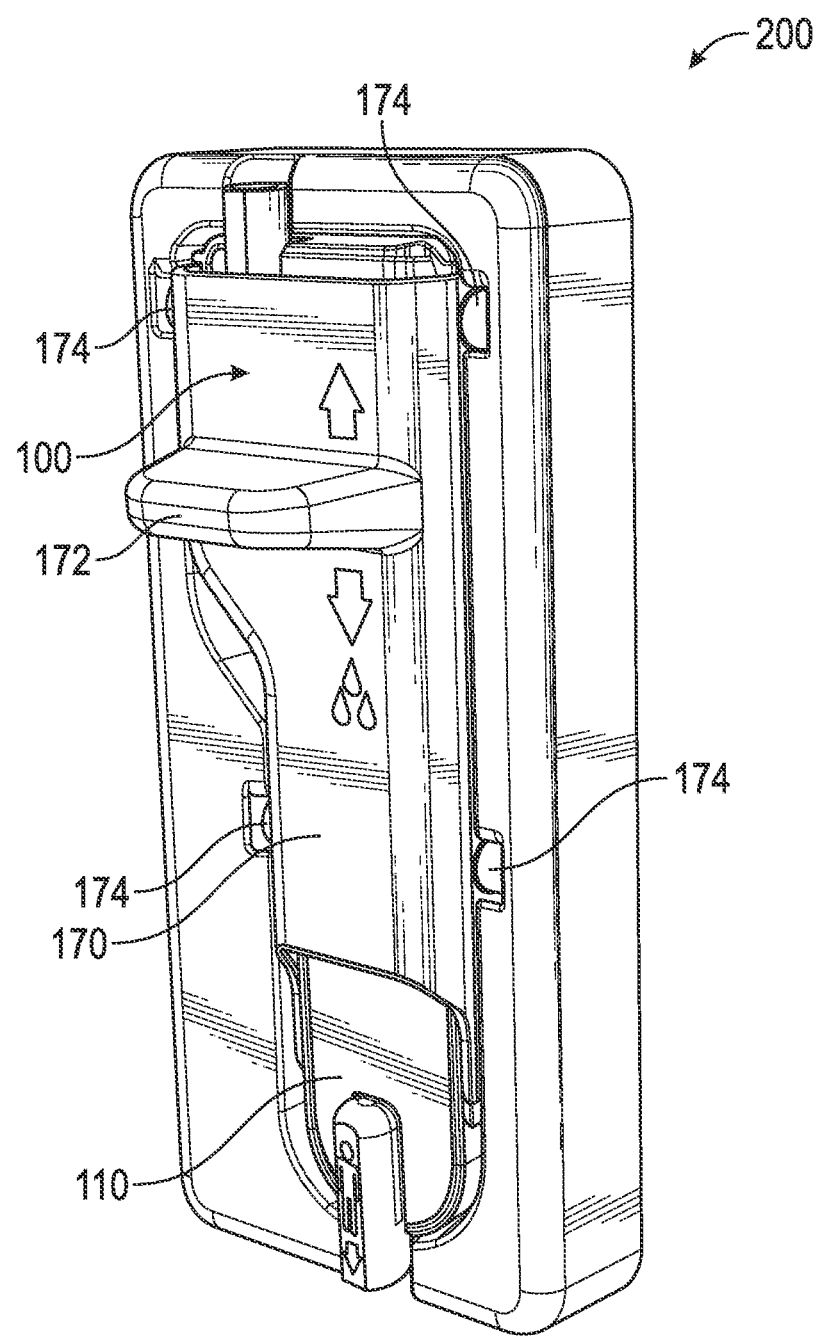
FIG. 4B illustrates perspective views of examples of a first embodiment disposable IV pump cassette and cassette recess, in accordance with aspects of the present disclosure.
Figure 4C:
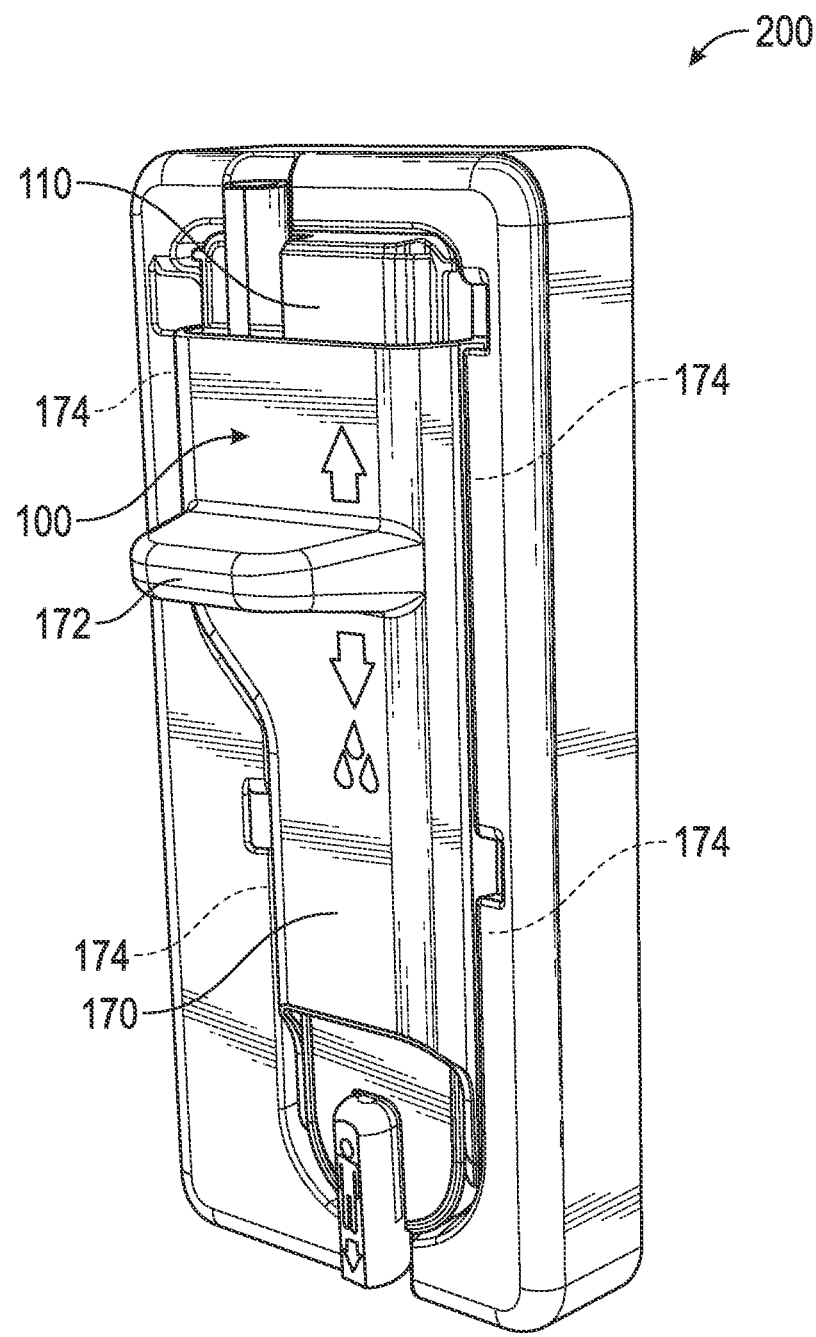
FIG. 4C illustrates perspective views of examples of a first embodiment disposable IV pump cassette and cassette recess, in accordance with aspects of the present disclosure.

FIGS. 4A-4C illustrate an example of a cassette engagement sequence with cassette 100 and cassette recess 200. Cassette 100 may be aligned such that the plurality of protrusions 174 on slider 170 may be aligned along z-axis 197 for engagement with the plurality of slots 274 of cassette recess 200. In accordance with certain aspects, cassette 100 may have a longitudinal length along y-axis 195, a lateral width along x-axis 196, and a depth along z-axis 197. As illustrated in FIG. 4A and described herein, the depth of the cassette 100 may be a smaller dimension than either the length or the width of cassette 100. In this regard, cassette 100 is front loaded into cassette recess 200.

As illustrated in FIG. 4B, the plurality of protrusions 174 on slider 170 of cassette 100 may engage with the plurality of slots 274 of cassette recess 200 such that cassette 200 is substantially seated (but not latched) within cassette recess 200. Next, as illustrated in FIG. 4C, slider 170 may be longitudinally articulated along y-axis 195 such that cassette 100 is latched within cassette recess 200. It is to be noted that in some embodiments, loading of cassette 100 within cassette recess 200 may be laterally oriented (e.g., 90° rotation of z-axis 197 so that x-axis 196 and y-axis 195 are switched).

Figure 5A:
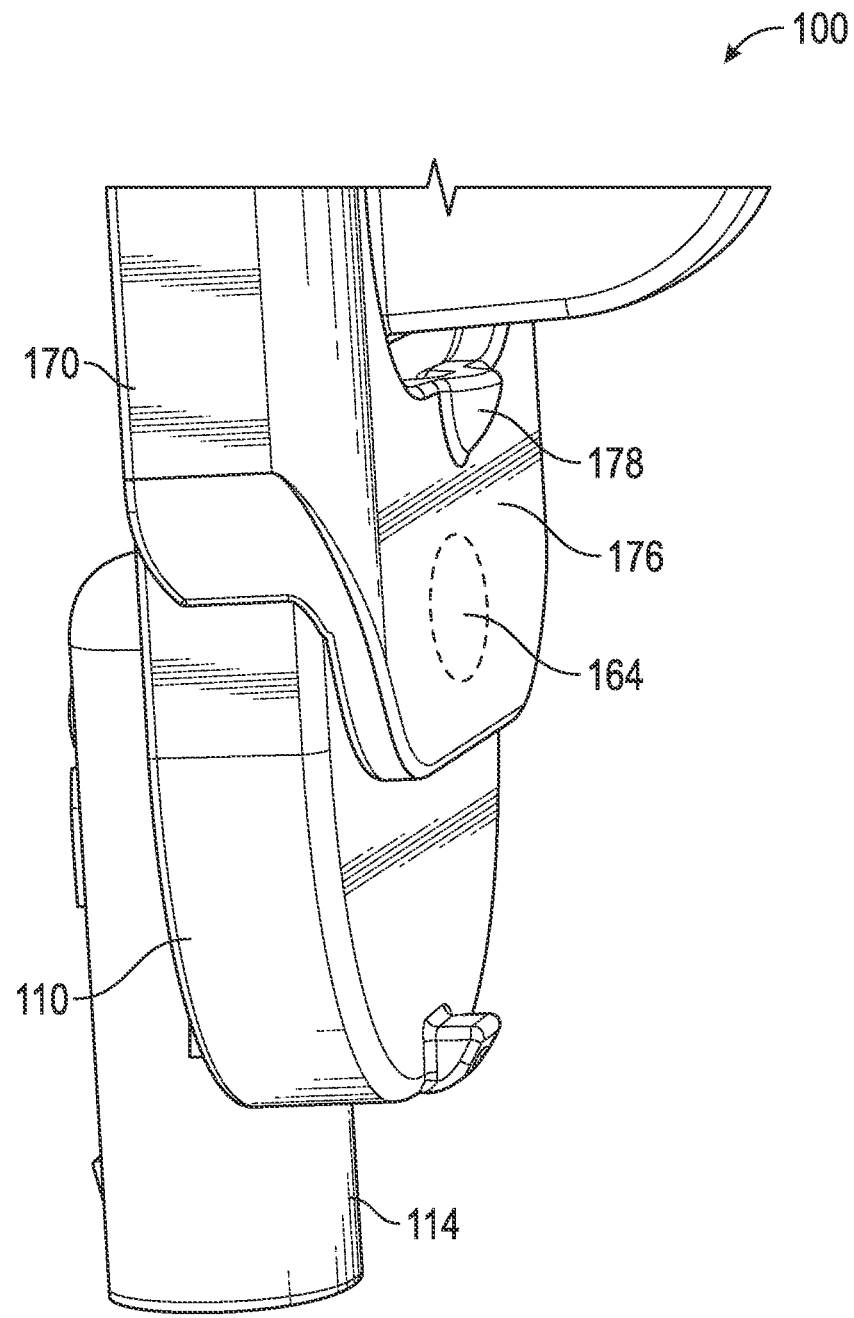
FIG. 5A illustrates an enlarged perspective view of an example of a first embodiment disposable IV pump cassette, in accordance with aspects of the present disclosure.
Figure 5B:
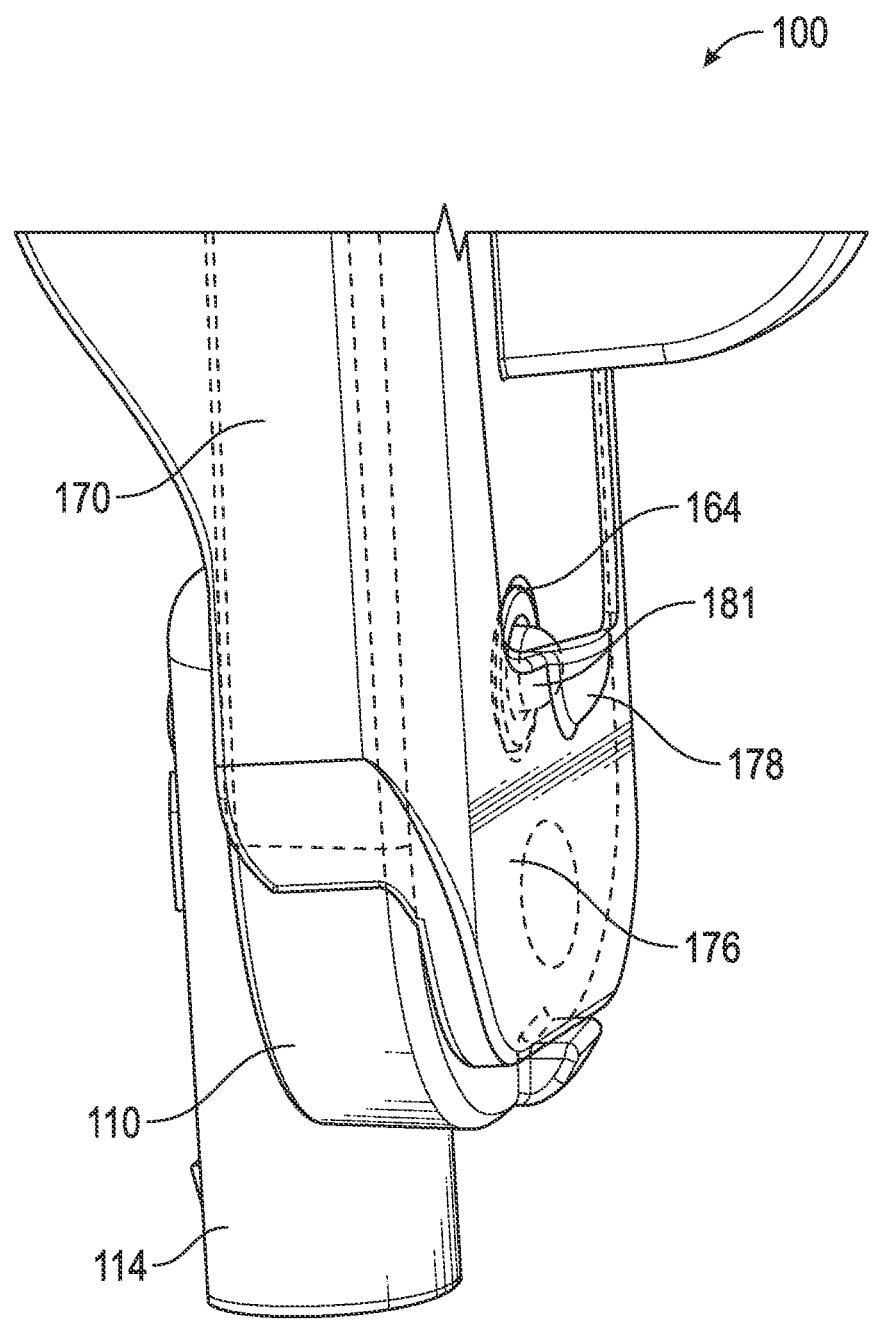
FIG. 5B illustrates an enlarged perspective view of an example of a first embodiment disposable IV pump cassette, in accordance with aspects of the present disclosure.
Figure 5C:
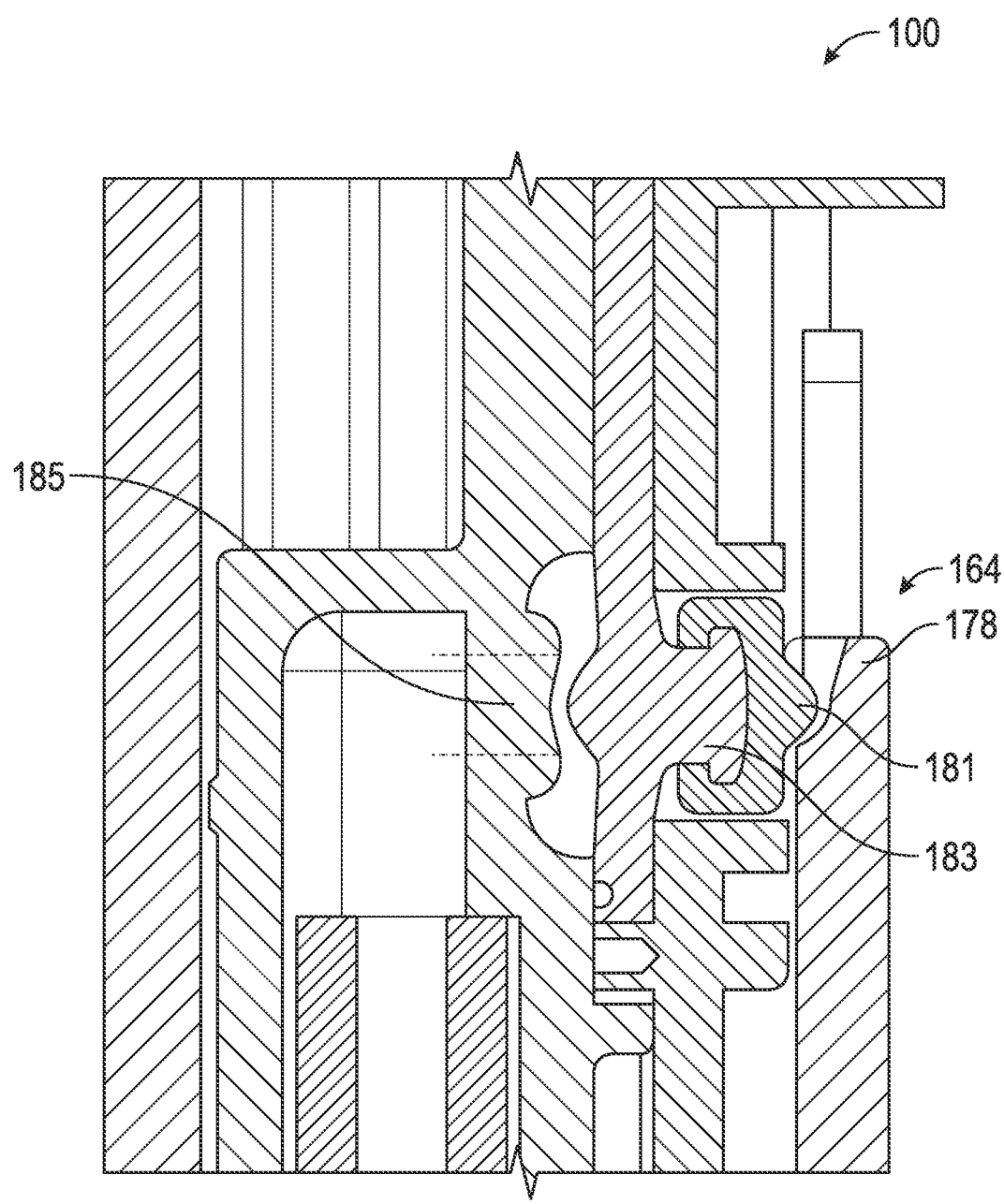
FIG. 5C illustrates a cross-sectional view of an example of a portion of a first embodiment disposable IV pump cassette, in accordance with aspects of the present disclosure.
Figure 5D:
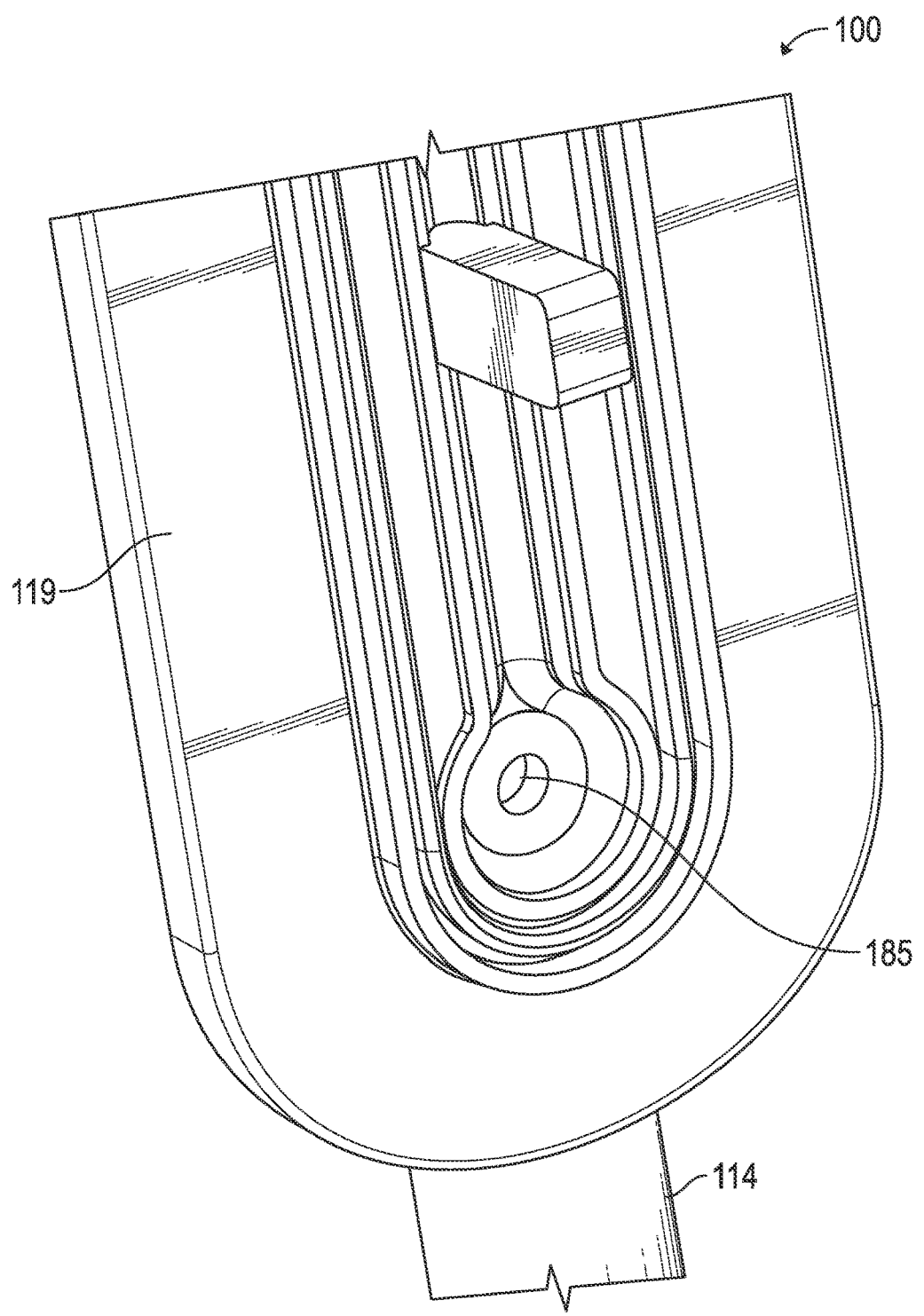
FIG. 5D illustrates a perspective view of an example of a portion of a first embodiment disposable IV pump cassette, in accordance with aspects of the present disclosure.

With reference to the example cassette engagement sequence of FIGS. 4A-4C, aspects of flow stop valve are provided with additional reference to the examples of FIGS. 5A and 5B. In certain embodiments, flow stop valve 164 may be configured to restrict and/or regulate fluid flow proximal to outlet 114 of cassette body 110. In order to insert cassette 100 into cassette recess 200, slider 170 should be articulated to a first position with respect to cassette body 110 (e.g., articulated upwardly in certain implementations; FIG. 4A). In the first position, flow stop valve 164 is aligned under a portion (e.g., flat surface) of interface-facing slider section 176 of slider 170 (FIG. 5A). When the slider 170 is positioned in the first position, the portion of interface-facing slider section 176 contacts and activates flow stop valve 164 such that fluid flow is occluded at that position of the fluid pathway proximal to outlet 114 cassette body 110. Therefore, fluid leakage can be avoided during the final preparation stages (e.g., after priming of cassette 100) and prior to insertion into cassette recess 200. In accordance with certain configurations, the first position of slider 170 may correspond to a position of cassette 100 for engaging and disengaging with cassette recess 200.

During insertion of cassette 100, once cassette body 110 is placed in cassette recess 200 (FIG. 4B), slider 170 can be articulated to a second position with respect to cassette body 110 (e.g., articulated downwardly in certain implementations; FIG. 4C). In this second position cassette 100 will be latched within cassette recess 200 by virtue of protrusions 174 being engaged with slots 274. In the second position, flow stop valve 164 is aligned under a stop valve guard 178 (e.g., ramped or recessed surface) of interface-facing slider section 176 of slider 170 (FIG. 5B). When the slider 170 is positioned in the second position, the portion of interface-facing slider section 176 does not contact flow stop valve 164 (or alternatively does not contact flow stop valve 164 sufficiently to activate flow stop valve 164), and flow stop valve 164 operates to allow fluid to flow freely through flow stop valve 164 to outlet 114.

In accordance with certain embodiments, stop valve guard 178 may be positioned proximal to an edge along interface-facing slider section 176 of slider 170 such that when cassette 100 is securely latched or locked within cassette recess 200 (e.g., in the second position; FIG. 4C), stop valve guard 178 is positioned above flow stop valve 164 (FIG. 5B). In this regard, stop valve guard 178 can protect flow stop valve 164 from being inadvertently depressed and activated to restrict fluid flow while cassette 100 is in use. For example, a force applied to the slider side of cassette 100 while locked within cassette recess 200 would not depress flow stop valve 164 as the lateral tolerances of the slidable coupling between cassette 100 and slider 170 are tighter than a distance between the inner surface of the stop valve guard 178 and an outer surface of the flow stop valve 164. In this regard, distances between stop valve guard 178 and flow stop valve 164 may be optimized such that anticipated forces applied to cassette 100 (e.g., from a user or caregiver inadvertently bumping cassette 100 or road vibrations in moving ambulance setting) may not cause an undesired activation of flow stop valve 164.

Similarly, when cassette 100 is to be disengaged from cassette recess 200, slider 170 can be unlatched or unlocked from cassette recess 200 by accessing slider grip 172 and articulating slider 170 back to the first position with respect to cassette body 110 (FIG. 4B). Some amount of force may be required by the user to articulate slider 170 to the first position as the plurality of protrusions 174 may be securely latched with corresponding slots 274 while the slider 170 is in the second position. Once slider 170 is in the first position, cassette 100 may be removed from cassette recess 200 by pulling slider grip 172 outwardly.

Furthermore, slider 170 may be articulated from the first position to the second position when cassette 100 is not engaged with cassette recess 200. Thus, flow stop valve 164 will operate to allow fluid to flow freely through flow stop valve 164 to outlet 114. Therefore, cassette 100 may be primed with fluid while being disengaged from cassette recess 200 when slider 170 is in the second position (but not latched with cassette recess 200).

It is to be understood that in other implementations, the stop valve guard feature can be a recess distal from an edge of interface-facing slider section 176, or an aperture or slit extending through interface-facing slider section 176, for example. Moreover, in some embodiments, flow stop valve and stop valve guard features may be positioned on the slider-facing side of cassette body 110.

The examples of FIGS. 5A-5D illustrate aspects of a flow stop valve. It is to be understood that various constructions of flow stop valve 164 are contemplated in the present disclosure. For example, in accordance with certain embodiments, striker 181 is configured to redirect the longitudinally introduced force applied by movement interface-facing slider section 176 into a more generally orthogonal force applied to top membrane portion 183 of flow stop valve 164. In some aspects, striker 181 can be a hard plastic (e.g., polycarbonate) dome-shaped piece disposed over and co-molded with top membrane portion 183. In other aspects, striker 181 may be constrained in a manner for engagement with top membrane portion 183 (e.g., situated in an aperture above top membrane portion 183). As such, potential sheering forces longitudinally applied directly to the membrane portion 183 of the flow stop valve 164 may be avoided in accordance with certain embodiments. Flow stop valve 164 may include through-hole base portion 185 (e.g., through base portion 119) for releasable engagement with top membrane portion 183. Top membrane portion 183 urged by striker 181 is configured to circumferentially seal through-hole base portion 185 so that fluid flow is restricted to outlet 114 in accordance with certain aspects.

Figure 5E:
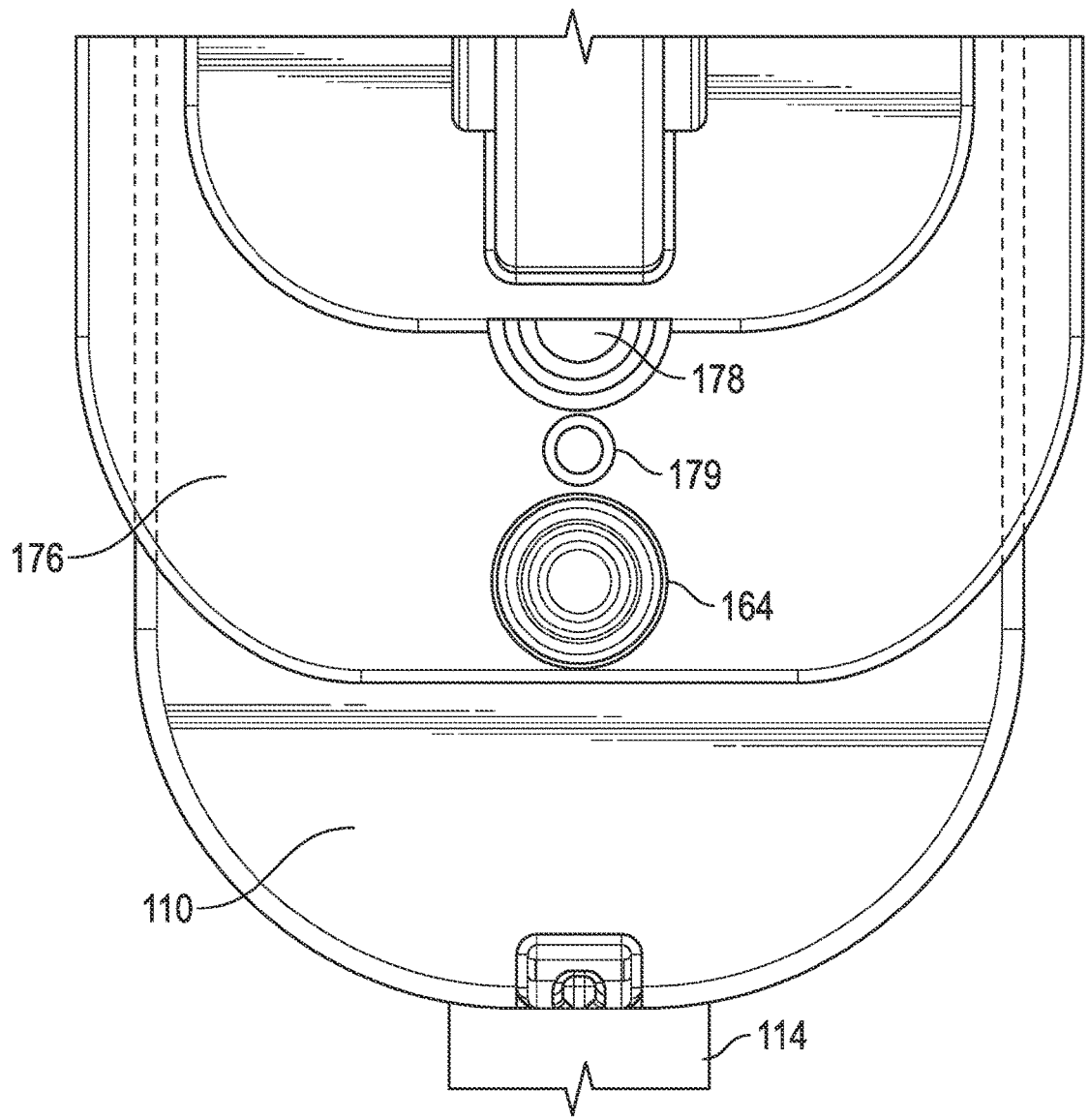
FIG. 5E illustrates a perspective view of an example of a portion of a first embodiment disposable IV pump cassette, in accordance with aspects of the present disclosure.
Figure 5F:
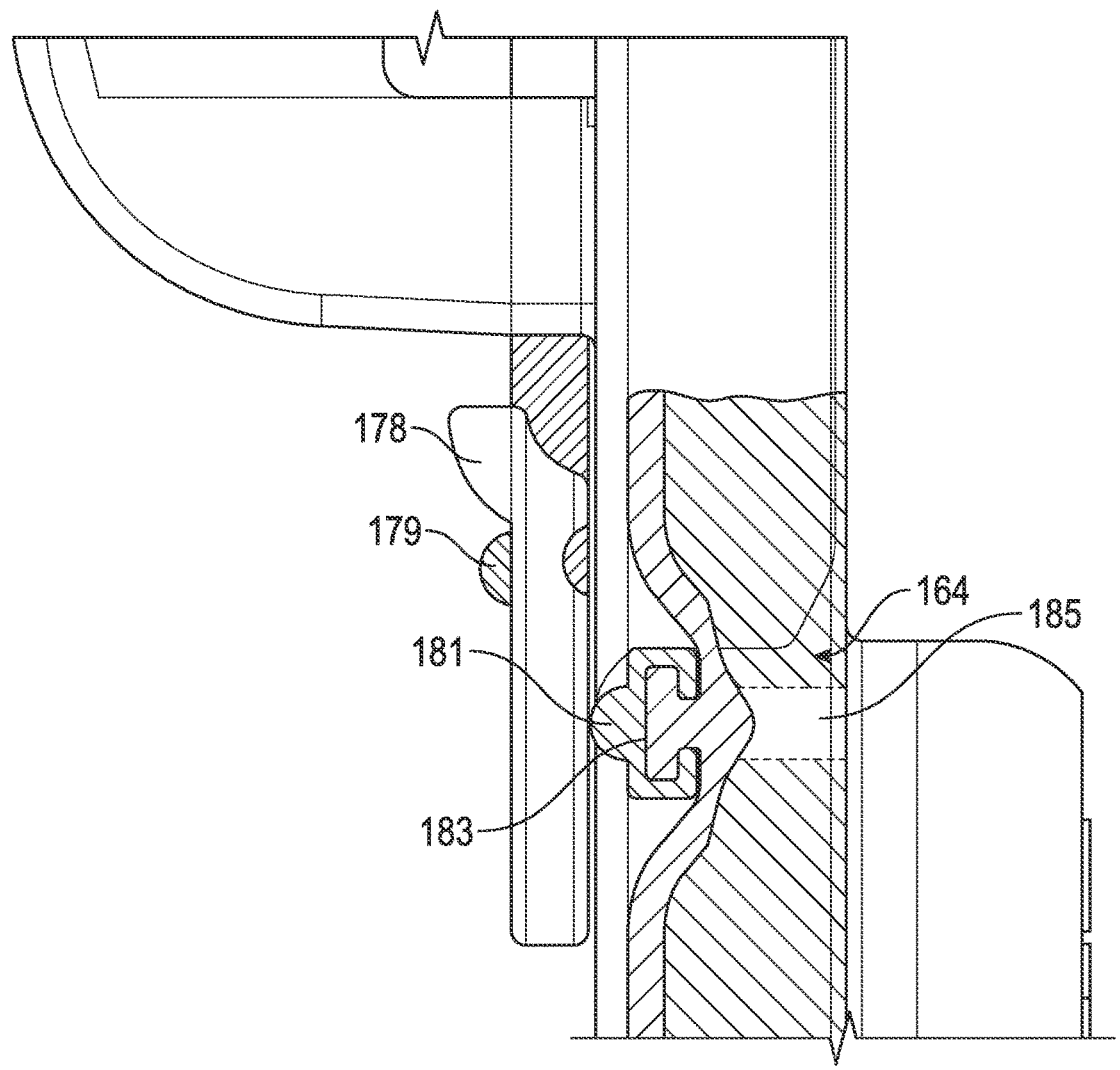
FIG. 5F illustrates a view of an example of a portion of a first embodiment disposable IV pump cassette, in accordance with aspects of the present disclosure.

In accordance with some embodiments, slider 170 may interface with flow stop valve 164 to regulate the fluid flow therethrough. As illustrated in the examples of FIGS. 5E and 5F, interface-facing slider section 176 may include one or more cassette-facing detents 179 for contacting striker 181 such that top membrane portion 183 partially occludes through-hole base portion 185 to regulate fluid flow to outlet 114. The one or more cassette-facing detents 179 may be longitudinally aligned corresponding to slider 170 motion with respect to striker 181. Accordingly, the resulting reduced fluid flow through outlet 114 may be beneficial during priming and preparation procedures when cassette 100 is not engaged with cassette recess 200. In some embodiments, when striker 181 makes contact with the one or more cassette-facing detents 179, an audible click may be heard or discernable vibration may be felt by the user or caregiver during the slider engagement process.

It is to be appreciated that in addition to the other noted advantages, the flow stop valve features described herein provide a flow stop operation of cassette 100 that does not involve interactions with infusion pump system 10, 11, cassette recess 200 or any mechanical or electrical component thereof.

Figure 6A:
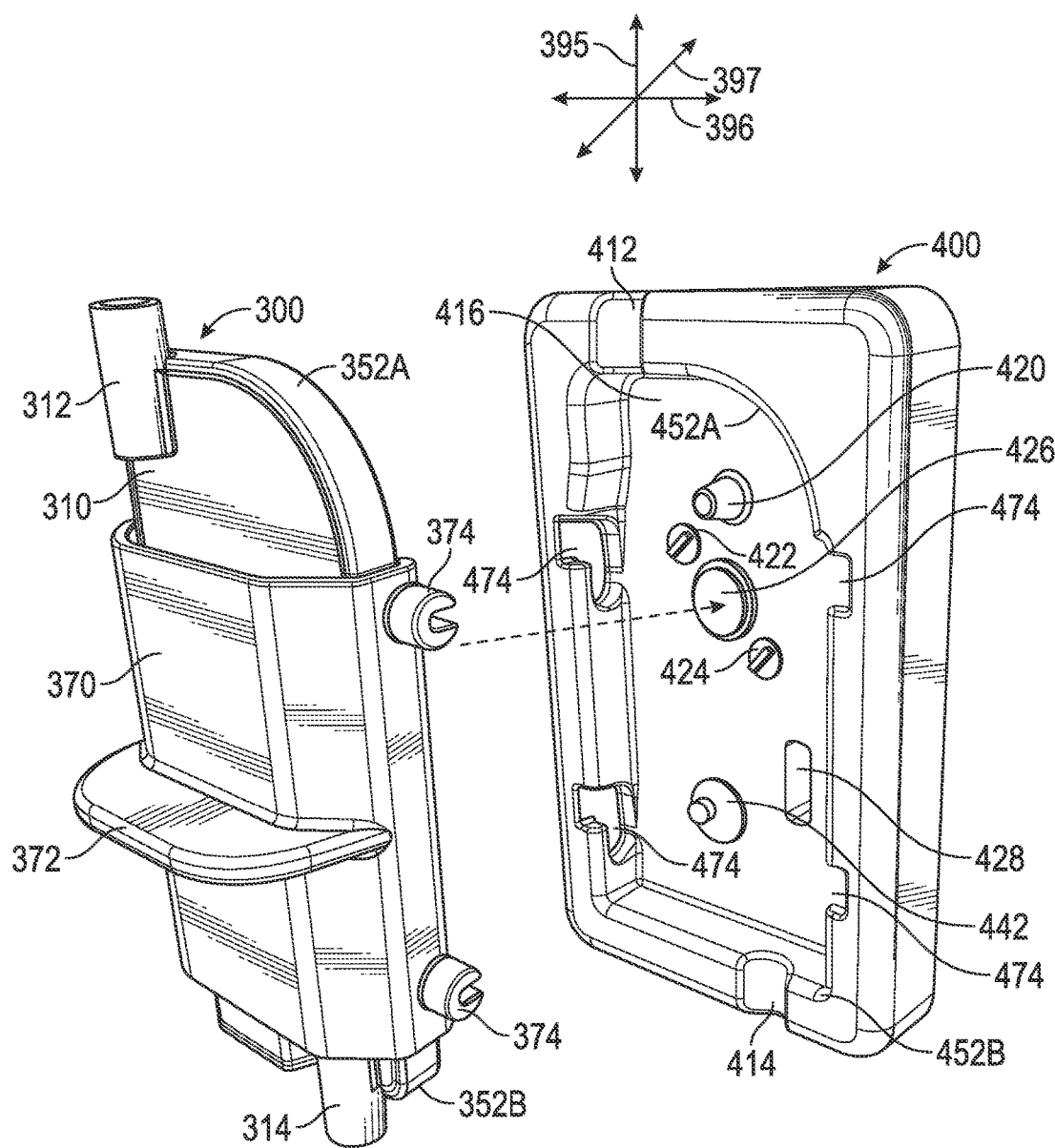
FIG. 6A illustrates perspective views of examples of second embodiment disposable IV pump cassette and cassette recess, in accordance with aspects of the present disclosure.
Figure 6B:
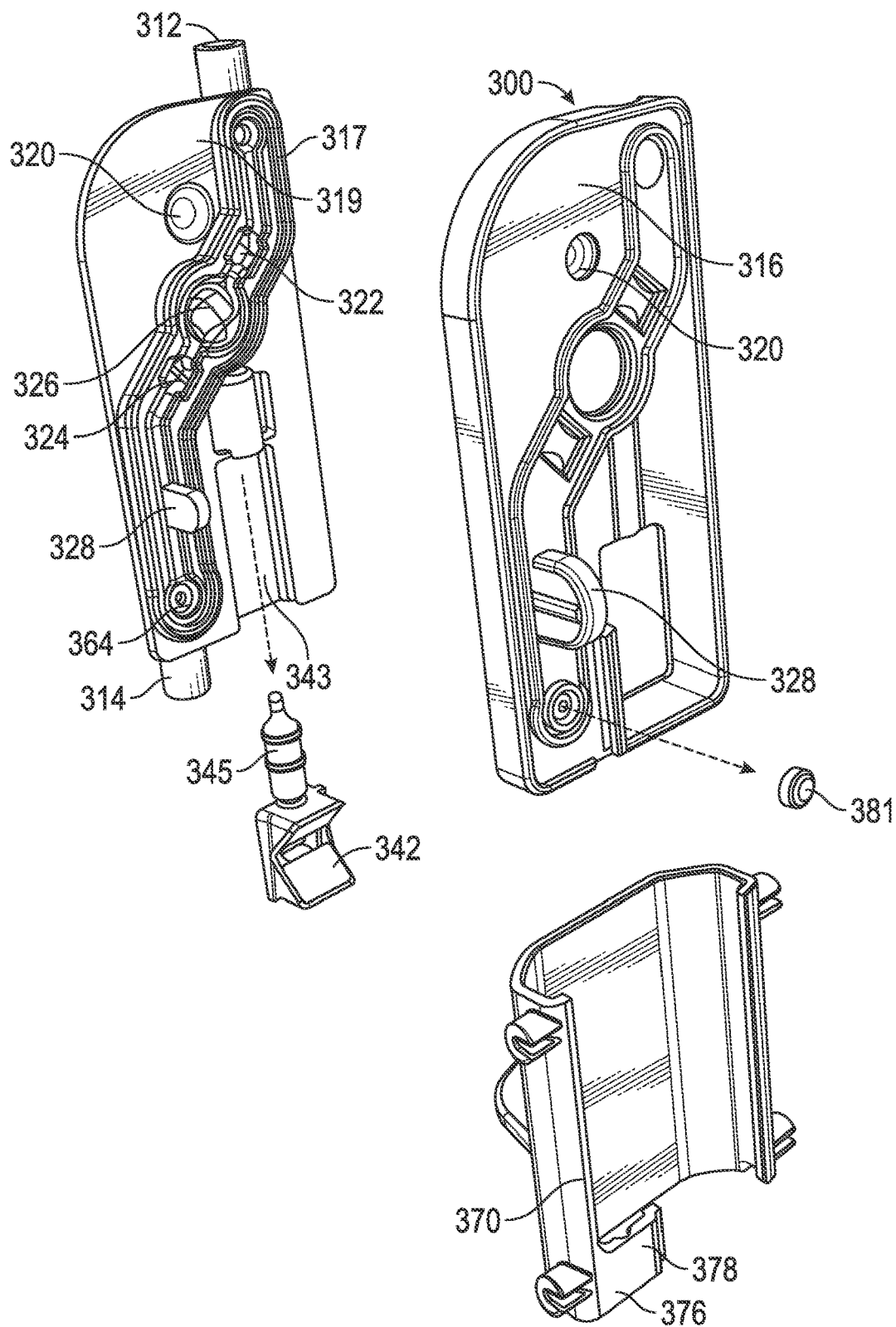
FIG. 6B is an exploded detail view illustrates a perspective view of second embodiment disposable IV pump cassette, in accordance with aspects of the present disclosure.

FIGS. 6A and 6B illustrate another example of a disposable IV cassette 300 and corresponding cassette recess 400 of an interface module. In accordance with other embodiments, cassette 300 may comprise a cassette body 310 and a slider 370. Cassette 300 may be operatively coupled to cassette recess 400.

In accordance with some embodiments, cassette 300 may comprise a cassette body 310 and a slider 370. Slider 370 can be fixably and slidably engaged with cassette body 310 such that slider 370 may articulate longitudinally with respect to cassette body 310, but will be constrained within range of sliding motion such that the slider remains coupled to the cassette body 310. In some embodiments, cassette 300 may be configured so that slider 370 does not extend around cassette body 310 (FIG. 6B).

In some embodiments, slider 370 includes a slider grip 372 and a plurality of protrusion 374 that are configured to be releasably lockable with a plurality of slots 474 of the cassette recess 400 (e.g., L-shaped locking channels). The plurality of protrusions 374 may be disposed at various locations on slider 370.

Edges 352 of cassette 300 and corresponding perimeter of cassette recess 400 may include at least one arcuate edge 352a contrasted with at least one opposite corner edge 352b, for example. Therefore, orientation of cassette 300 with respect to loading engagement with corresponding arcuate perimeter edge 452a and corner edge 452b of cassette recess 400 may be readily apparent to a user or caregiver.

In accordance with some aspects, an overall size of cassette 300 and cassette recess 400 may be reduced. For example, in some embodiments, cassette body 310 may extended longitudinally a length between 65 mm and 75 mm, for example, by utilizing a single pump chamber/reservoir for sensing probe. Additionally, cassette body 310 may extended laterally a width between 34 mm and 39 mm, and may extend a depth between 10 mm and 14 mm. Fluid pathway extension member 328 may further extend between 8 mm to 10 mm. In some aspects, slider grip 372 may extend between 10 mm to 14 mm from cassette body 310.

For orientation reference with respect to the examples illustrated of FIG. 6A, longitudinal axis or y-axis 395, latitudinal axis or x-axis 396, and depth axis or z-axis 397 are provided. In this regard, depth aspects of cassette 300 is shown in the example of FIG. 6A.

The process of cleaning of inlet recess 412, outlet recess 414, and cassette recess 400 is made efficient by the shallow recess configuration in accordance with some embodiments should any fluid or debris accumulate within cassette recess 400. For example, the plurality of slots 474 arranged within cassette recess 400 can reached and cleaned with a swab.

The shallow recess configuration of cassette recess 400, and associated longitudinal alignment of cassette 300 such that a smaller of volumetric dimensions of cassette 300 (e.g., depth being smaller than length and width in some embodiments) further enables additional space for arrangement of mechanical couplings and operational interfaces and optimizes the overall space requirements of cassette recess 400 and infusion pump system, or the like, in general.

Various types, placement, and orientations of the plurality of protrusions 374 disposed on slider 370 are contemplated as described herein. Moreover, in accordance with some aspects, features of cassette recess 400 are designed to avoid wear down and/or risk of malfunction. For example, the plurality of slots 474 arranged within cassette recess 400 may not include any movable latching mechanism in some embodiments as such movable latching mechanisms may be susceptible to excessive wear and mechanical failure over repeated use with multiple disposable IV cassettes 300.

Cassette 300 can be loaded into cassette recess 400. In this regard, the loading of the interface-facing side of cassette body 310 can avoid sheer forces applied to the sensors, alignment features, and other engaging interfaces of cassette body and cassette-facing surface 416 of cassette recess 400.

With reference to the examples of FIG. 6B, cassette body 310 may comprise interface-facing frame portion 316 and slider-facing base portion 319 with membrane 317 disposed substantially therebetween (e.g., portions of membrane 317 may extend through some openings of frame portion 316). In accordance with some embodiments, membrane 317 can be a compliant material co-molded to the base portion 319 and sealingly engaged with frame portion 316 for defining a fluid pathway through cassette body 310 from inlet 312 to outlet 314. In some embodiments, membrane 317 may also be co-molded to striker 381 for defining, in part, a flow stop valve 364.

Mating edges of frame portion 316 and base portion 319 may be connected by fusing, welding, gluing, or the like. Membrane 317 and base portion 319 may further define a plurality of other features, some of which may be accessed through openings in frame portion 319.

Frame portion 316, membrane 317, and/or base portion 319 may define features in or along the fluid pathway, in accordance with some embodiments.

For example, beginning from inlet 312, the fluid pathway may include features such as, but not limited to, inlet-side valve 322, pump chamber/sensing reservoir 326, outlet-side valve 324, fluid pathway extension member 328, and flow stop valve 364. Other features that are not in or along the fluid pathway, but are disposed on cassette body 310, may include positioning port 320. With respect to extension member 328, a portion of the fluid pathway can be extended away or protrude orthogonally from the generally flat and planar exterior surface of interface-facing frame portion 316 so as to make the fluid in the fluid pathway available for other detection techniques performed by infusion pump system 10, 11.

As illustrated, fluid pathway extension member 328 may be formed from orthogonally extending portions of frame portion 316, membrane 317, and base portion 319. However, in other embodiments, a fluid pathway access point may be configured for air-in-line detection, for example, from a section of the exterior surface of interface-facing frame portion 316.

One or more fluid sensors may be disposed within sensor slot 428 such as ultrasonic sensors configured as an air-in-line detector. In some embodiments, extension member 328 may be disposed on cassette body 310 and positioned along the fluid pathway between pump chamber/sensing reservoir 326 and flow stop valve 364.

Cassette body 310 may include a pump drive assembly in accordance with some embodiments. For example, the pump drive assembly may include pump drive mechanism 342 for receiving pump actuator 442 of cassette recess 400. Pump drive mechanism 342 can be operatively coupled to piston 345 slidably engaged within piston guide 343 casing (e.g., generally cylindrical or frustoconical casing) such that reciprocal movement of piston 345 may change a total volume of pump chamber pump chamber/sensing reservoir 326 thereby urging fluid through the fluid pathway of cassette body 310.

In some embodiments, pump drive assembly may be configured to produce a 3.5 mm piston stroke for operation with pump chamber/sensing reservoir 326 configured to be a 10 mm outer diameter reservoir. Moreover, pump drive assembly may be arranged below pump chamber/sensing reservoir 326, in accordance with some embodiments.

With cassette 300 primed and secured in cassette recess 400, an example pumping operation may comprise activating outlet-side valve actuator 424 such that outlet-side valve 324 is closed or sealed while activating inlet-side valve actuator 422 such that inlet-side valve 322 is opened. Opening of inlet-side valve 322 may coincide with or occur shortly after a reverse stroke of piston 345 (e.g., a movement of piston 345 away from pump chamber/sensing reservoir 326). Accordingly, fluid can flow from inlet 312 to pump chamber/sensing reservoir 326.

Pumping operation may further comprise activating outlet-side valve actuator 424 such that outlet-side valve 324 is open while activating inlet-side valve actuator 422 such that inlet-side valve 322 is closed or sealed. Opening of outlet-side valve 324 may coincide with or occur shortly before a forward stroke of piston 345 (e.g., a movement of piston 345 toward pump chamber/sensing reservoir 326 such that contact is by a head of piston 345 is made with a portion of pump chamber/sensing reservoir 326). Thus, fluid can flow from pump chamber/sensing reservoir 326 to outlet 314.

In some embodiments, cassette recess 400 may include pump chamber sensing probe 426 to enable measurement of in-line pressure. For example, pump chamber sensing probe 426 may operably contact pump chamber/sensing reservoir 326 sized to be sufficient for pressure sensing through a corresponding opening of interface-facing frame portion 316.

As illustrated in the example of FIG. 6A, cassette 300 may be aligned such that the plurality of protrusions 374 on slider 370 may be aligned along z-axis 397 for engagement with the plurality of slots 474 of cassette recess 400. In accordance with some aspects, cassette 300 may have a longitudinal length along y-axis 395, a lateral width along x-axis 396, and a depth along z-axis 397. The depth of cassette 300 may be a smaller dimension than either the length or the width of cassette 300. In this regard, cassette 300 is loaded into cassette recess 400.

In accordance with some examples, the x-y positioning of cassette 300 within cassette recess 400 can be constrained by the positioning port 320 and positioning protrusion 420 mating interface, as well as fluid pathway extension member 328 and sensor slot 428 mating interface. In this regard, cassette 300 and cassette recess 400 can have two point of contact in the z-axis direction (e.g., an axis through and transverse to a general plane of the interface-facing surface of cassette body 310 of cassette 300 and cassette-facing surface 416 of cassette recess 400) for interlock alignment of the cassette with respect to the x-y positioning of the interface side of the cassette body 310.

In some embodiments, positioning port 320 may be located proximal to inlet-side valve 322 and aligned above pump chamber/sensing reservoir 326. Positioning protrusion 420 may be located proximal to inlet-side valve actuator 422 and aligned above pump chamber sensing probe 426. Accordingly, the cassette 300 may be positioned properly to aid in sensing accuracy for a single sensing reservoir implementation without over constraining the cassette 300.

In some embodiments, the positioning port 320 and positioning protrusion 420 mating interface, and fluid pathway extension member 328 and sensor slot 428 mating interface, together form the controlling index for proper x-axis and y-axis alignment of the interface-facing frame portion 316 (e.g., dual-feature x-y positioning scheme).

Flow stop valve 364 may be configured to restrict and/or regulate fluid flow proximal to outlet 314 of cassette body 310, in accordance with some embodiments. In order to insert cassette 300 into cassette recess 400, slider 370 should be articulated to a first position with respect to cassette body 310 (e.g., articulated upwardly in some implementations). In the first position, flow stop valve 364 may be aligned under a portion (e.g., flat surface) of interface-facing slider section 376 of slider 370. When the slider 370 is positioned in the first position, the portion of interface-facing slider section 376 contacts and activates flow stop valve 364 such that fluid flow is occluded at that position of the fluid pathway proximal to outlet 314 cassette body 310.

Therefore, fluid leakage can be avoided during the final preparation stages (e.g., after priming of cassette 300) and prior to insertion into cassette recess 400. During insertion of cassette 300, once cassette body 310 is placed in cassette recess 400, slider 370 can be slid to a second position with respect to cassette body 310 (e.g., articulated downwardly in some implementations).

In the second position, flow stop valve 364 may be aligned under a stop valve guard 378 (e.g., ramped or recessed surface) of interface-facing slider section 376 of slider 370. When the slider 370 is positioned in the second position, the portion of interface-facing slider section 376 does not contact flow stop valve 364 (or alternatively does not contact flow stop valve 364 sufficiently to activate flow stop valve 364), and flow stop valve 364 operates to allow fluid to flow freely through flow stop valve 364 to outlet 314. Therefore, cassette 300 may be operable for fluid flow rate regulation via cassette recess 400.

In accordance with some embodiments, stop valve guard 378 may be positioned proximal to an edge along interface-facing slider section 376 of slider 370 such that when cassette 300 is securely latched or locked into cassette recess 400 (e.g., in the second position), stop valve guard 378 is positioned above flow stop valve 364. In this regard, stop valve guard 378 can protect flow stop valve 364 from being inadvertently depressed and activated to restrict fluid flow while cassette 300 is in use. For example, a force applied to the slider side of cassette 300 while locked within cassette recess 400 would not depress flow stop valve 364 as the lateral tolerances of the slidable coupling between cassette 300 and slider 370 may be tighter than a distance between the inner surface of the stop valve guard 378 and an outer surface of the flow stop valve 364. In this regard, distances between stop valve guard 378 and flow stop valve 364 may be optimized such that anticipated forces applied to cassette 300 and/or cassette recess 400 may not cause an undesired activation of flow stop valve 364.

Similarly, when cassette 300 is to be disengaged from cassette recess 400, slider 370 can be unlatched or unlocked from cassette recess 400 by accessing grip 372 and articulation slider 370 back to the first position with respect to cassette body 310. Some amount of force may be required by the user or caregiver to move slider 370 to the first position as the plurality of protrusions 374 may be securely latched with corresponding slots 474 while the slider 270 is in the second position. Once slider 370 is in the first position, cassette 300 may be removed from cassette recess 400 by pulling grip 372 outwardly.

Slider 370 may be articulated from the first position to the second position when cassette 300 is not engaged with cassette recess 400 or interface module. Thus, flow stop valve 364 will operate to allow fluid to flow freely through flow stop valve 364 to outlet 314. Therefore, cassette 300 may be primed with fluid while being disengaged from cassette recess 400 when slider 370 is in the second position (but not latched within cassette recess 400).

In accordance with some embodiments, striker 381 of flow stop valve 364 is configured to redirect the longitudinally introduced force applied by movement interface-facing slider section 376 into a more generally orthogonal force applied a top membrane portion or other valve actuation mechanism of flow stop valve 364. In some aspects, striker 381 can be a hard plastic (e.g., polycarbonate) dome-shaped piece disposed over and co-molded the top membrane portion.

In accordance with some embodiments, slider 370 may interface with flow stop valve 364 to regulate the fluid flow therethrough. Interface-facing slider section 376 may include one or more cassette-facing detents or a ramp or incline portion fixably movable with respect to striker 381 such that flow stop valve 364 can be partially occluded to regulate fluid flow to outlet 314.

It is to be further appreciated that cassette 100, 300 and the various features thereof may be constructed from a few number of components (e.g., formed from four to seven parts in accordance with certain embodiments) as described herein given the benefit of the present disclosure.

Figure 7A:
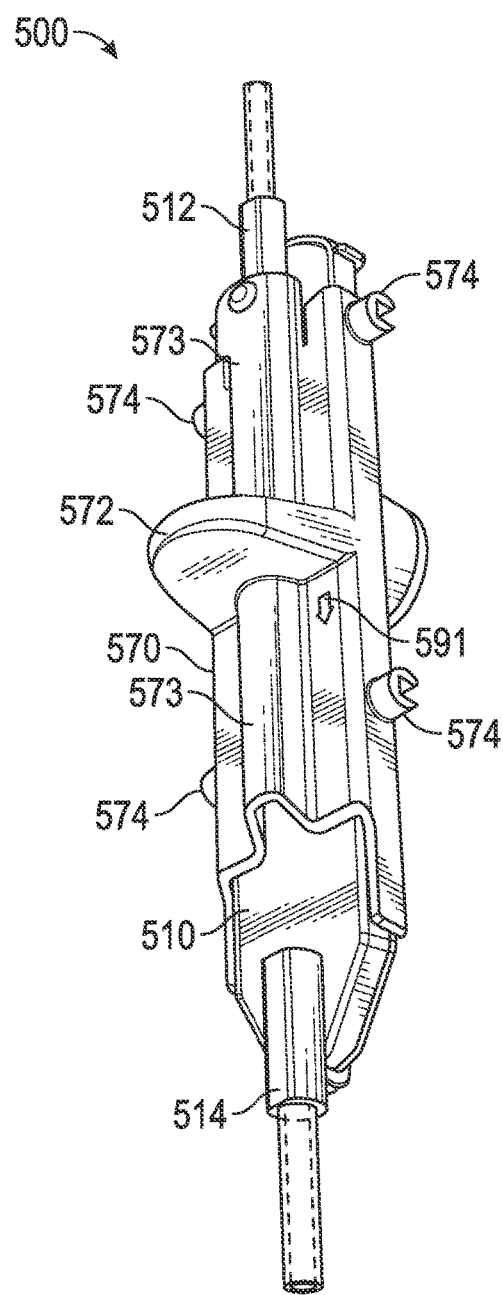
FIGS. 7A and 7B illustrate perspective views of examples of a third embodiment disposable IV pump cassette and cassette recess, in accordance with aspects of the present disclosure.
Figure 7B:
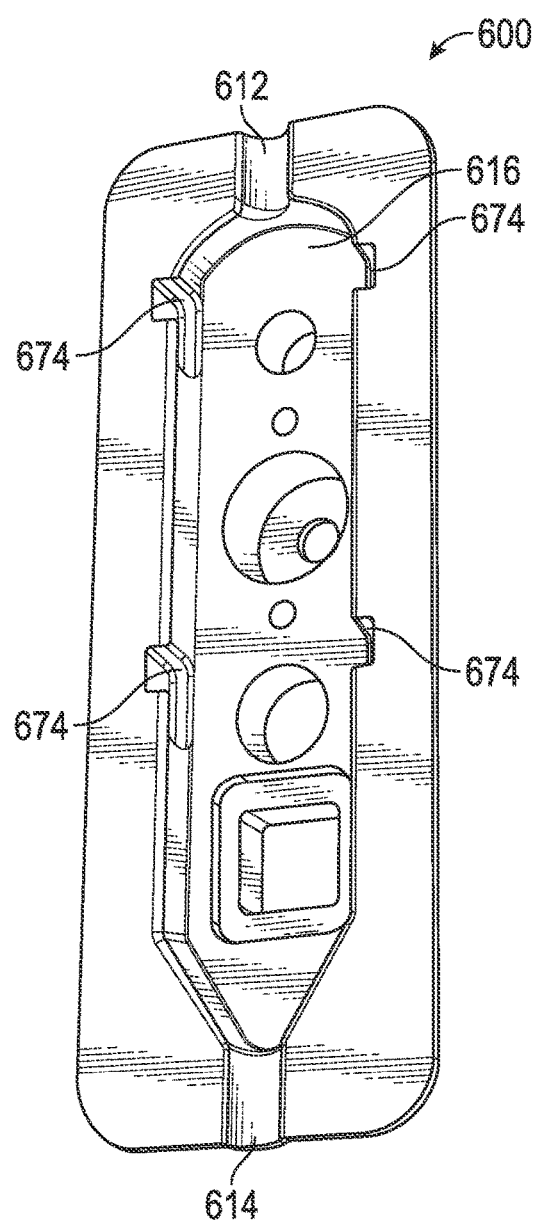

FIGS. 7A and 7B illustrate examples of a disposable IV pump cassette 500 and corresponding cassette recess 600 of an interface module. In accordance with certain embodiments, cassette 500 may comprise a cassette body 510 and a slider 570. Cassette 500 may include certain may include certain visual indicators related to operation aspects of the cassette and the infusion pump system in general. For example, cassette may include identifiable images such as arrows indicating that the slider 570 may articulate longitudinally 591 with respect to cassette body 510 and a patient figure proximal to outlet 514. In accordance with some aspects, cassette 500 may include one or more lens areas 573 for magnification of the fluid pathway within the cassette body 510. The one or more lens areas 573 may be disposed on the slider 570 extending at least a portion of the fluid pathway within the cassette body 510. In some embodiments, the one or more lens areas 573 may extend longitudinally along the slider 570. In accordance with some aspects, the one or more lens areas 573 may provide magnification for greater than approximately 50% of the fluid pathway extending within the cassette body 510 from inlet 512 to outlet 514. In this regard, during priming or prepping a cassette 500, as well as during operation of the cassette 500, a user or caregiver may use the one or more lens areas 573 to ensure that any visible air bubbles throughout a substantial portion or the fluid pathway have been removed and fluid is flowing properly. In accordance with some aspects, one or more cassette-seated sensors may be disposed within the cassette recess 600 so as to inform central processing unit 12 that the cassette is locked or secured into place within the cassette recess 600 or seat.

Slider 570 can be fixably and slidably engaged with cassette body 510 such that slider 570 may articulate longitudinally 591 with respect to cassette body 510, but may be constrained within range of sliding motion such that the slider remains coupled to the cassette body 510, for example. Slider 570 may be formed from rigid plastic or polymer material having lubricating characteristics (e.g., incorporating silicon or polytetrafluoroethylene (PTFE) additives), and is clear or translucent in accordance with certain embodiment. In some embodiments, slider 570 may be polycarbonate. Slider 570 includes a slider grip 572 or handle portion and a plurality of protrusion 574 or lugs that are configured to be releasably lockable with a plurality of slots 674 of the cassette recess 600 (e.g., L-shaped locking channels). In this regard, cassette 500 can be self-latched into the cassette recess 600. Accordingly, a door or lever action is not required in order to retain the cassette 500 within the cassette recess 600. As such, when the cassette is used in an infusion pump system in accordance with certain aspects of the present disclosure, a front area of the cassette 500 including grip 572 can be accessed during operation of the infusion pump system.

Figure 7C:
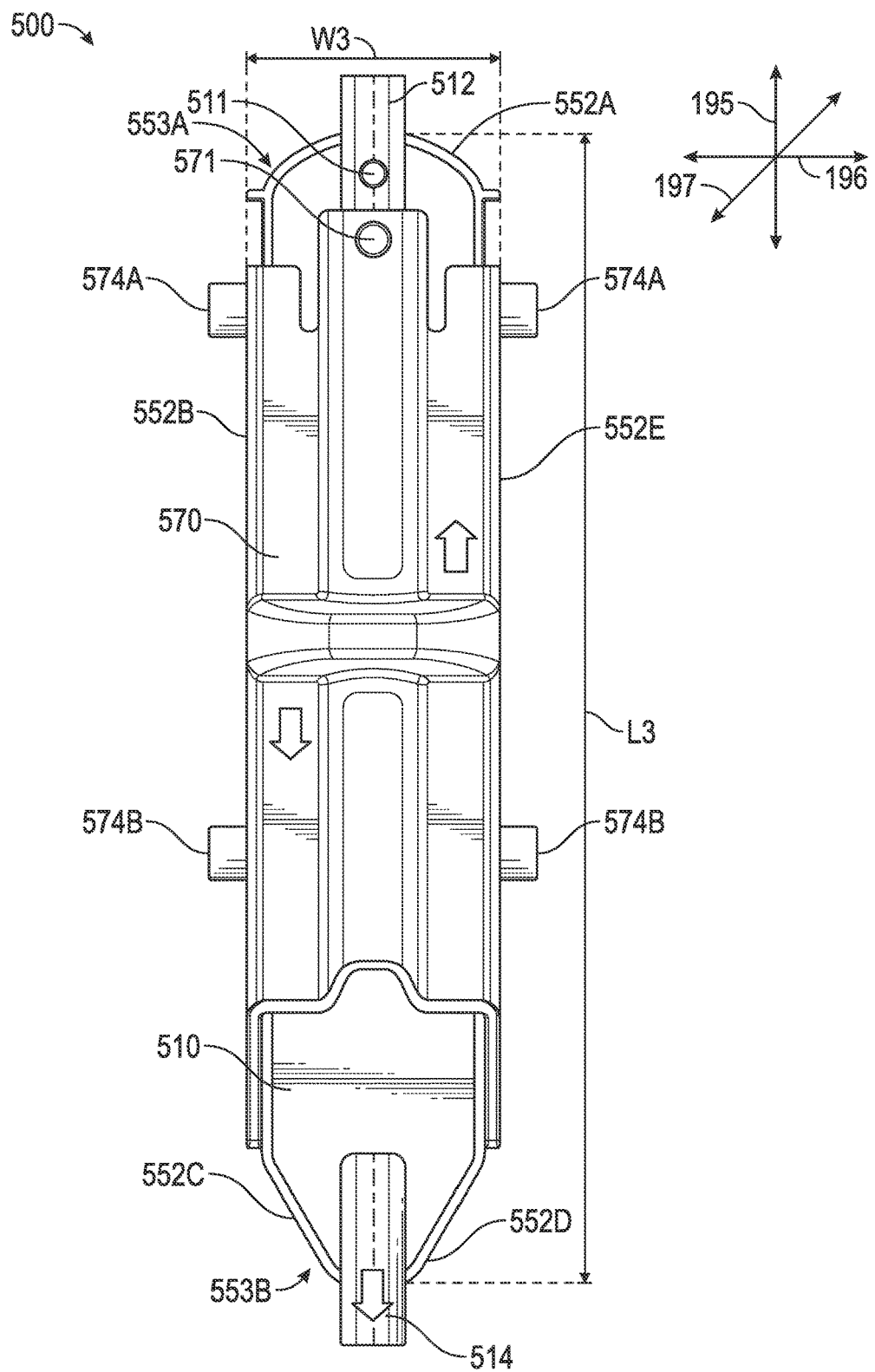
FIG. 7C illustrates a front perspective view of an example of a third embodiment disposable IV pump cassette, in accordance with aspects of the present disclosure.

Similar to other described embodiments, the plurality of protrusions 574 may be disposed at various locations on slider 570. As illustrated in the example of FIG. 7C, slider 570 may comprise a first pair of protrusions 574a and a second pair of protrusions 574b. The first pair of protrusions 574a may be spaced apart a similar distance (e.g., width W3) as the second pair of protrusions 574b. Thus, opposite sides (e.g., left and right sides according to an example orientation) of cassette 500 can be substantially parallel in certain embodiments. In accordance with some aspects, W3 may be between 21 mm and 25 mm in some embodiments. Cassette 500 may comprise a first end portion 553a (e.g., top portion according to an example orientation) of cassette body 510 that is shaped differently that a second end portion 553b (e.g., bottom portion according to an example orientation) of cassette body 510.

For example, first end 553a can be slightly rounded or squared off with respect to the sides of cassette body 510, whereas second end 553b can be angled or otherwise generally pointed (e.g., indicative of a direction of fluid flow through cassette 500). Inlet 512 may be substantially longitudinally aligned with outlet 514, in accordance with certain embodiments. In this regard, cassette 500 orientation within cassette recess 600 is clear to a user or caregiver such that a cassette 500 is not inadvertently installed (or inadvertently positioned when being primed) in an inverted manner.

Accordingly, perimeter edges 552 of cassette 500 and corresponding perimeter edges of cassette recess 600 may include one or more perimeter edges for engagement between cassette 500 and cassette recess 600. For example, the perimeter edges 552 may correspond to a perimeter opening of cassette recess 600 for front-loading cassette 500 into cassette recess 600. In accordance with certain implementations, front-loading a cassette means that the cassette engages with a cassette recess disposed on a surface of an interface unit in a direction of the smallest of the cassette's three general dimensions (e.g., a depth along a z-axis as illustrated in the figures). In this regard, a surface of an interface unit may be on located on a front, side, or rear surface with respect to a general front of the interface unit (e.g., where the electronics and display are located) and still be considered to be front-loading surface. Additionally, in some implementation, a front-loaded cassette may be readily accessible to a user or caregiver to remove such that no cover prohibits access to the installed cassette. However, in other implementations, a locked or latched cover may exist on the interface unit to protect or limit access to the installed cassette. It is to be further understood that the front-loaded cassette need not be installed with the cassette's longitudinal axis extending vertically with respect to an upright position of the interface unit. For example, some interface units may include cassette recesses oriented such that the longitudinal axis of the front-loading cassette is oriented horizontally with respect to the interface unit.

Figure 7D:
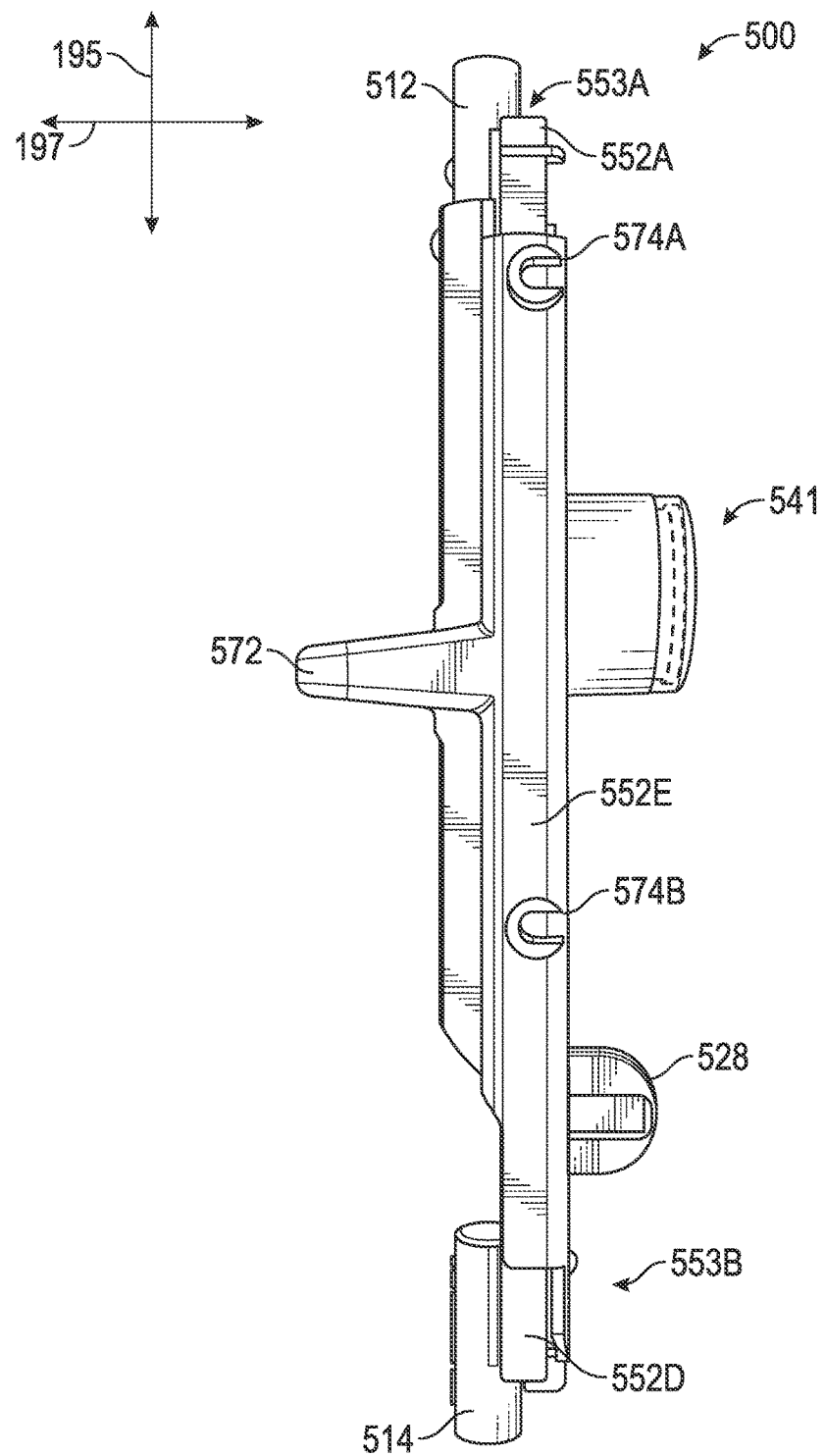
FIG. 7D illustrates a side perspective view of an example of a third embodiment disposable IV pump cassette, in accordance with aspects of the present disclosure.

With reference to FIGS. 7C and 7D, cassette body 510 (with or without slider 570) may comprise top lateral edge 552a, straight longitudinal side edge 552b, angled bottom edge 552c, angled bottom edge 552d, and straight longitudinal side edge 552e. Straight longitudinal side edge 552b and straight longitudinal side edge 552e may be generally parallel and opposing edges as described herein, in accordance with certain example aspects.

First and second end portion 553a, 553b, may provide benefit by enabling visual identification as well as prohibiting improper orientation or seating of cassette 500 with a corresponding cassette recess 600. Additionally, minimizing a size of cassette 500 and optimizing a surface area of one or more corresponding cassette recess 600 may be achieved by the elongate longitudinal design of cassette 500. Moreover, in certain embodiments, inlet 512 may be substantially longitudinally aligned with outlet 514 with the fluid pathway extending in a generally straight line from inlet 512 to outlet 514, thereby simplifying user or caregiver troubleshooting of cassette 500 during operation of infusion pump system 10, 11, as well as allowing free flow of fluid during priming of cassette 500.

In some embodiments, cassette 500 may include detent 511 and corresponding recess 571. For example, detent 511 may be position on or proximate to inlet 512 be positioned on the slider An overall size of cassette 500 and cassette recess 600 may be reduced, in accordance with some aspects. For example, in certain embodiments, cassette body 510 may extended longitudinally a length (L3) between approximately 85 mm and 128 mm. In this regard, cassette body 510 may be dimensioned as having an elongate body section with a length larger than a width. For orientation reference with respect to the various views of the examples illustrated of FIGS. 7C and 7D, longitudinal axis or y-axis 195, latitudinal axis or x-axis 196, and depth axis or z-axis 197 are provided.

In this regard, depth aspects of cassette 500 is shown in the example of FIG. 7D. For example, in certain embodiments, cassette body 510, or a substantial portion thereof, may extend depth (D3) between 6 mm and 8 mm. Fluid pathway extension member 528 may further extend between 8 mm to 10 mm, and pump structure 541 may further extend between 10 mm to 16 mm, in accordance with some embodiments. In certain aspects, slider grip 572 may extend between 10 mm to 14 mm from cassette body 510. It is to be appreciated that the process of cleaning of inlet recess 612, outlet recess 614, and cassette recess 600 is made efficient in the shallow recess configuration in accordance with certain embodiments should any fluid or debris accumulate within cassette recess 600. The shallow recess configuration of cassette recess 600, and associated longitudinal alignment of cassette 500 such that a smaller of volumetric dimensions of cassette 500 (e.g., depth being smaller than length and width in certain embodiments) further enables additional space for arrangement of mechanical couplings and operational interfaces and optimizes the overall space requirements of cassette recess 600 and infusion pump system in general.

Various types, placement, and orientations of the plurality of protrusions 574 disposed on slider 570 are contemplated in the present disclosure. In accordance with certain aspects, features of cassette recess 600 are designed to avoid wear down and/or risk of malfunction. For example, the plurality of slots 674 arranged within cassette recess 600 may be devoid of any movable latching mechanism in certain embodiments as such movable latching mechanisms may be susceptible to excessive wear and mechanical failure over repeated use with multiple disposable IV cassettes 500. In operation, cassette 500 can be loaded directly into cassette recess 600. In this regard, the direct loading of the cassette 500 will enable avoidance of sheer forces that might otherwise be applied to the sensors, alignment features, and other engaging interfaces of cassette-facing surface 616 of cassette recess 600 from interaction with the interface-facing side of cassette body 510 as it is loaded into cassette recess 600.

It is to be understood that modification to the various features of cassette 500 can be made to accommodate the various cassette features and coupling techniques of other embodiments disclosed herein.

Figure 8A:
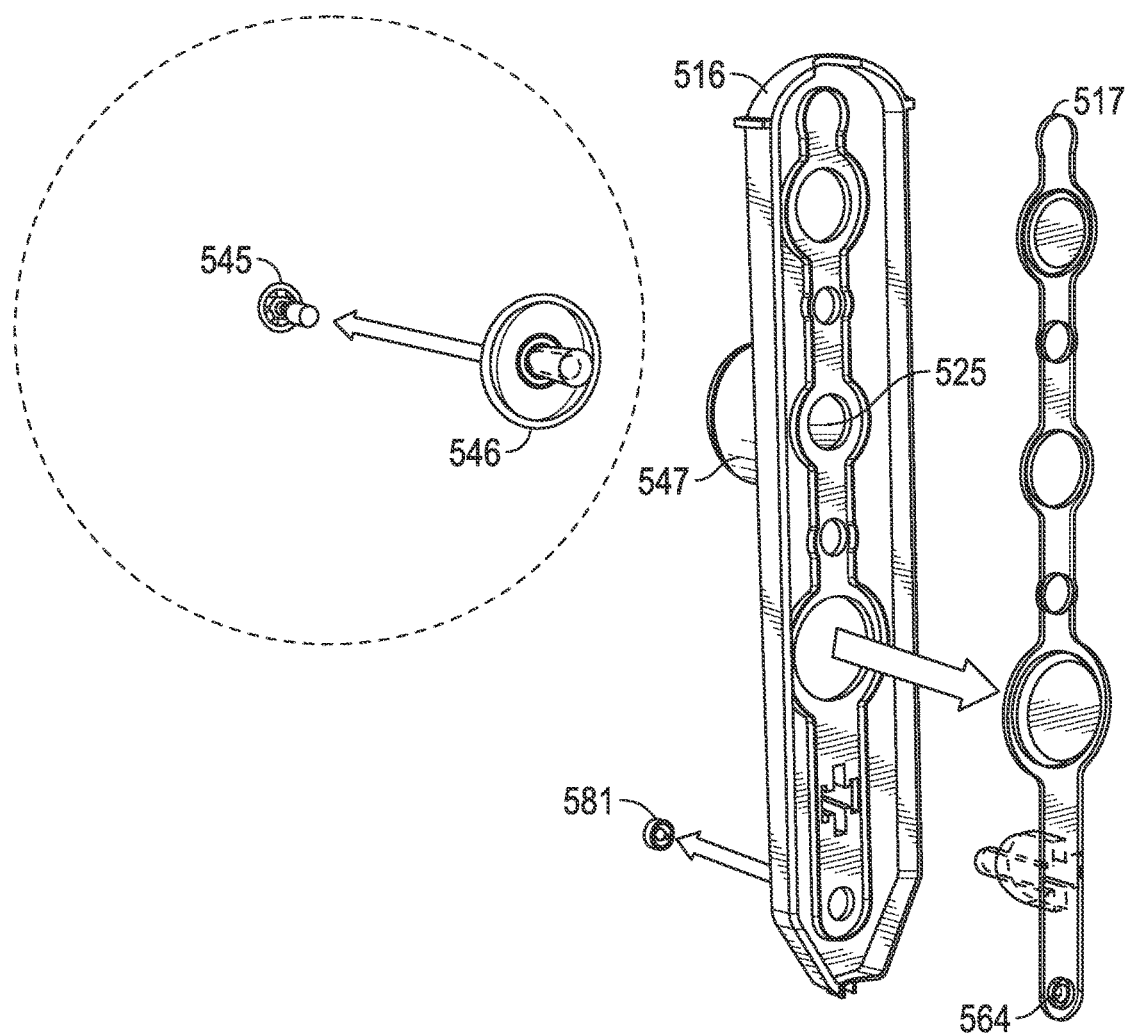
FIGS. 8A and 8B are exploded perspective detail views illustrating an example of a third embodiment disposable IV pump cassette, in accordance with aspects of the present disclosure.
Figure 8B:
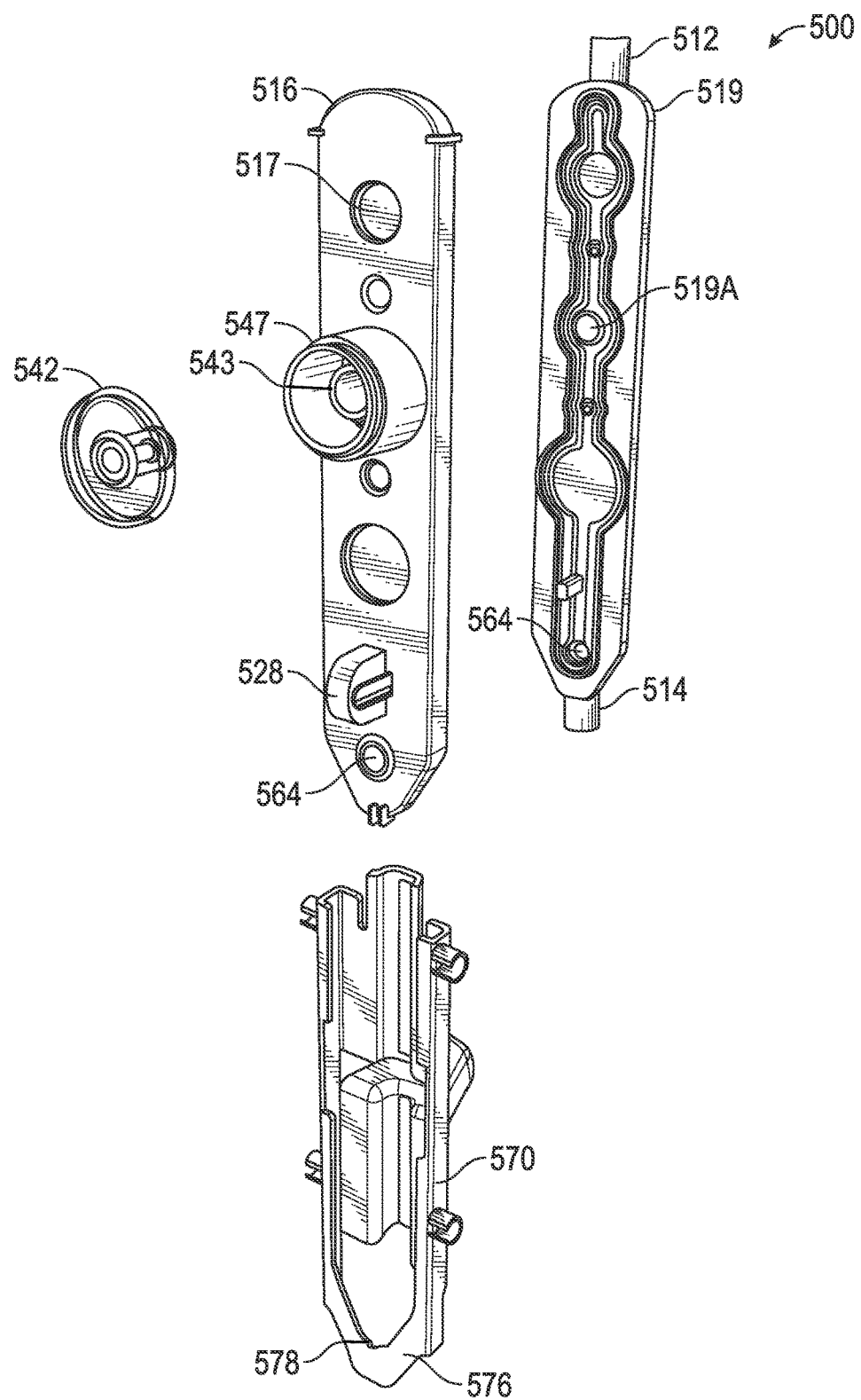
Figure 8C:
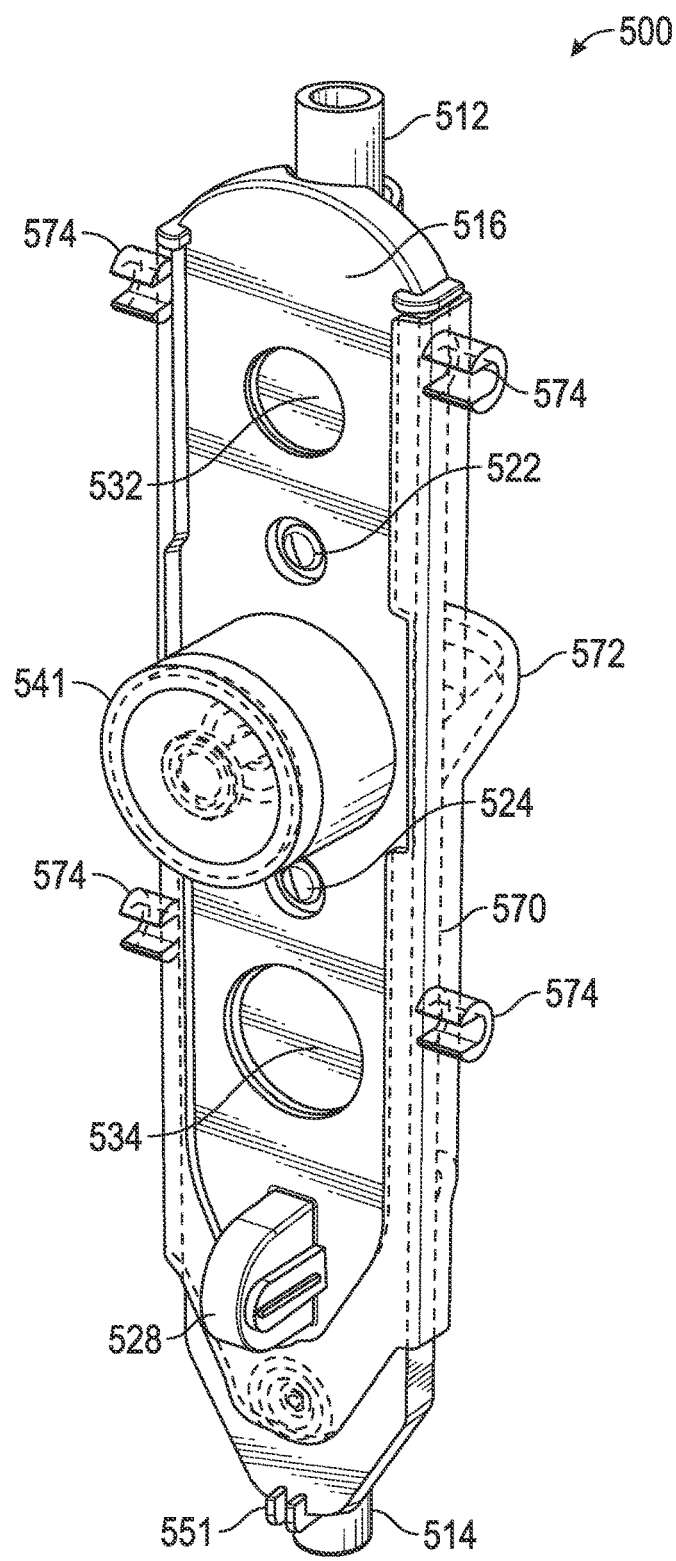
FIG. 8C illustrates a perspective view of an example of a third embodiment disposable IV pump cassette, in accordance with aspects of the present disclosure.

Referring now to the examples of FIGS. 8A-8C, cassette body 510 may comprise interface-facing frame portion 516 and slider-facing base portion 519 with membrane 517 disposed substantially therebetween (e.g., portions of membrane 517 may extend through some openings of frame portion 516). In accordance with certain embodiments, membrane 517 can be a compliant material co-molded to the frame portion 516 and sealingly engaged with base portion 519 for defining a fluid pathway through cassette body 510 from inlet 512 to outlet 514. Mating edges of frame portion 516 and base portion 519 may be connected by fusing, welding, gluing, or the like. Membrane 517 and base portion 519 may further define a plurality of other features, some of which may be accessed through openings in frame portion 516.

Frame portion 516, membrane 517, and/or base portion 519 may define features in or along the fluid pathway, in accordance with certain embodiments. For example, beginning from inlet 512, the fluid pathway may include features such as, but not limited to, upstream pressure dome 532 (e.g., an inlet-side compliant reservoir), inlet-side valve 522, pump chamber 525 (e.g., within a pump chamber wall 543 of pump structure 541), outlet-side valve 524, a downstream pressure dome 534, (e.g., an outlet-side compliant reservoir), fluid pathway extension member 528, and flow stop valve 564.

In certain embodiments, for example, first pair of protrusions 574a and second pair of protrusion 574b may be disposed on slider 570 such that when slider 570 is engaged with and locked into cassette recess 600 and corresponding slots 674, the first pair of protrusions 574a is positioned or laterally aligned with upstream pressure dome 532 and corresponding inlet-side pressure sensing probe recess 632a, and the second pair of protrusions 574b is positioned or laterally aligned with downstream pressure dome 534 and corresponding outlet-side sensing probe recess 634a. In this regard, structural integrity of cassette 500 and pressure sensing operations may be optimized in accordance with aspects of the present disclosure.

Other features of cassette 500 disposed on cassette body 510, may include pump structure 541 having an exterior support wall 574 that can be used as a positioning protrusion, for example, and slider stopper 551. With respect to extension member 528, a portion of the fluid pathway can be extended away or protrude orthogonally from the generally flat and planar exterior surface of interface-facing frame portion 516 so as to make the fluid in the fluid pathway available for certain detection techniques performed by infusion pump system 10, 11. As illustrated in the example of FIGS. 8A-8C, fluid pathway extension member 528, as well as pump structure 541, may be formed from orthogonally extending portions of frame portion 516, membrane 517, and/or base portion 519.

In accordance with certain embodiments, membrane 517 may be formed from a thermoplastic elastomer (TPE). Characteristics of certain TPEs can enable effective co-molding with other materials, for example, polycarbonate. Accordingly, in some embodiments, membrane 517 may be co-molded to frame portion 516 and striker 581 may be co-molded to a portion of membrane 517 defining a flow stop valve 564. However, in some embodiments, membrane 517 can be formed from silicon, a silicon-based compound, an elastomeric material suitably compliant for fluid flow, or the like.

In accordance with certain embodiments, interface-facing frame portion 516 and slider-facing base portion 519 may be formed from a rigid plastic such as, but not limited, a polycarbonate. Additionally, the rigid plastic of frame portion 516 and base portion 519 may be clear or translucent. The material of membrane 517 (e.g., TPE or other compliant material) and rigid plastic slider 570 may also be clear or translucent, thereby allowing a user or caregiver to readily observe fluid passage through a substantial portion of the fluid pathway of cassette body 510. In some embodiments, the fluid pathway portion of cassette body 510 will be clear or translucent, and other portions will be frosted so as to direct a user or caregiver's attention to the fluid pathway.

In some implementations, slider 570, base portion 519, and membrane 517 may be clear or translucent (or at least some portions along the fluid pathway), and the frame portion 516 may not be translucent. For example, the frame portion 516 may be colored in a manner so as to contrast against a color or tint of the fluid expected to be used with cassette 500. In some embodiments, one or more lens areas 573 may be disposed on base portion 519 alternatively, or in addition to, one or more lens areas 573 disposed on slider 570.

Figure 8D:
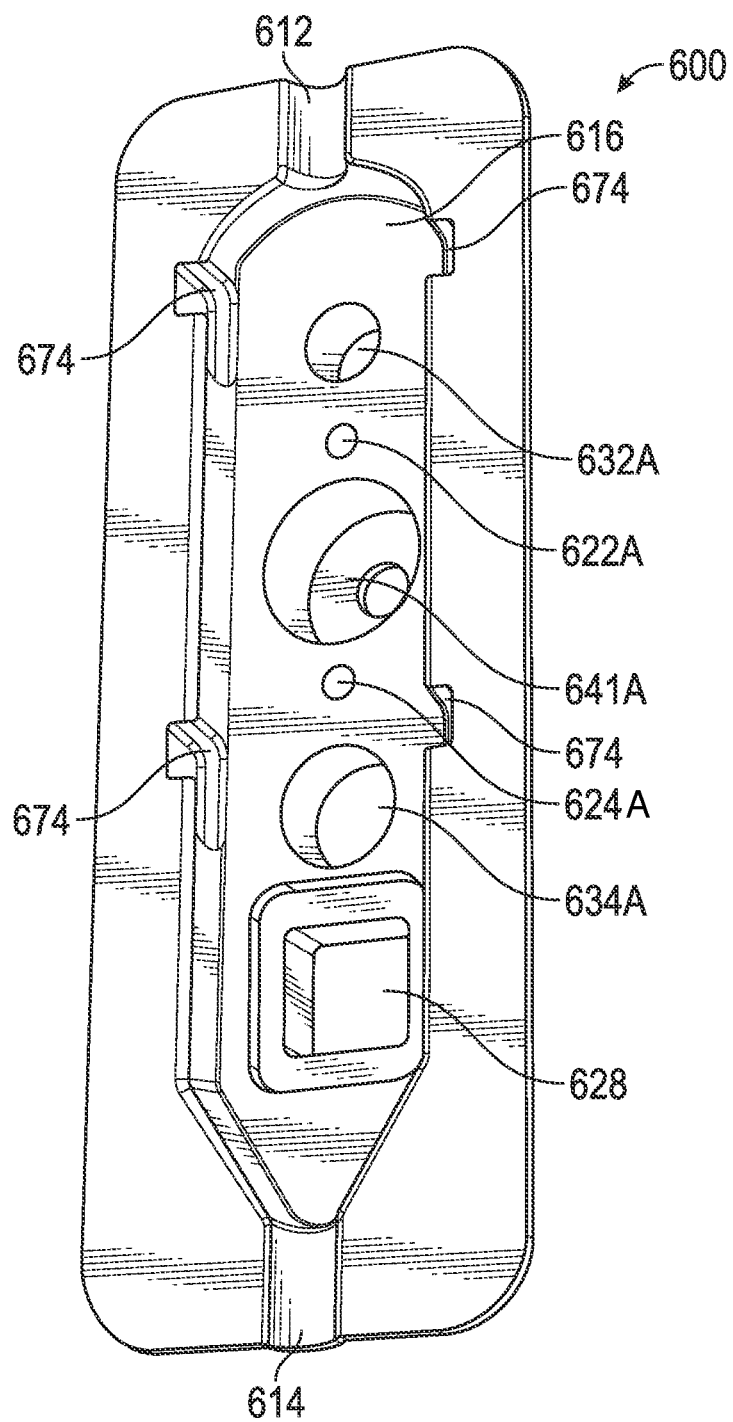
FIG. 8D illustrates a perspective view of an example of a third embodiment cassette recess, in accordance with aspects of the present disclosure.

With additional reference to the example of FIG. 8D, one or more fluid sensors may be disposed within sensor slot 628. The one or more fluid sensors disposed within sensor slot 628 can be ultrasonic sensors configured with an air-in-line detector, for example. In certain embodiments, extension member 528 may be disposed on cassette body 510 and positioned along the fluid pathway between downstream pressure dome 534 and flow stop valve 564. However, in some embodiments, extension member 528 can be positioned at other locations along the fluid pathway. Additionally, in other embodiments, a plurality of extension members 528 with a plurality of corresponding sensor slots 628 may be positioned along a fluid pathway of cassette body 510.

As illustrated in the examples of FIG. 8A-8E, cassette body 510 may include a pump structure 451 in accordance with certain embodiments. For example, the pump structure 541 may include piston assembly 542 for receiving pump actuator 642 of cassette recess 600. As such, cassette 500 with pump structure 541 may be configured for orthogonal piston assembly operation whereby a pump actuator of an interface module applies a force orthogonal to a general plane of interface-facing frame portion 516. Piston assembly 542 can include piston 545 co-molded with elastomeric seal member 546; however, other piston assemblies are contemplated under the present disclosure. Elastomeric seal member 546 may be secured to a portion of support wall 547 (e.g., an outer rim portion) distal to a general plane of the interface-facing surface of cassette body 510 so that piston assembly 542 may be slidably engaged with pump chamber wall 543. A chamber seal surface 546a of elastomeric seal member 546 that is internal to the pump structure 541 may be slidably engaged with an internal surface of the pump chamber wall 543 such that the seal surface 546a constitutes a moveable wall portion of pump chamber 525. Chamber base section 519a of base portion 519 may constitute an opposing stationary wall portion of the pump chamber 525.

In this regard, pump chamber 525 may be defined by pump chamber wall 543, chamber base section 519a, and seal surface 546a, in accordance with certain embodiments. Thus, movement of the piston assembly 542 and associated seal surface 546a can change a volume of pump chamber 525 to urge fluid through the fluid pathway of cassette body 510. As such, the fluid pathway may be controllable by operation of the pump chamber 525, inlet-side valve 522, outlet-side valve 524, and flow stop valve 564, for example.

In certain embodiments, slider grip 572 (or like portion of slider 570) may be positioned such that slider grip 572 is proximate to pump structure 541 (e.g., laterally respect to z-axis 197) such that a single hand of a user or caregiver can be used to prime cassette and articulate the slider 570 to control fluid flow. For example, a user or caregiver may place and secure slider grip 572 between two fingers of a first hand and use the thumb of the first hand to manually pump the pump structure 541 by pressing on an exterior portion of the piston assembly 542. The user or caregiver may apply a force to the exterior portion of the piston assembly 541 that is substantially orthogonal to a general plane of an interface-facing surface of the pump cassette 500, for example. The user or caregiver may articulate slider 570 with leverage from the thumb of the first hand in contact with the pump structure 541 (or proximate thereto) from a first position to a second position to occlude or allow fluid flow through cassette 500 when the cassette 500 is not engaged with cassette recess 600. Thus, in some embodiments, slider grip 572 may be positioned on slider 570 such that slider grip 572 is proximal to pump structure 541 and distal from inlet 512 in any articulable position of the slider 570 (e.g., from the first position to the second position) operably engaged with cassette body 510. In this regard, the pump cassette 500 may be ergonomically designed for quick priming.

Pumping operation of infusion pump system 10, 11 when cassette 500 is primed and seated in cassette recess 600 may comprise activating outlet-side valve actuator 624 (not shown in FIG. 8C) in outlet-side valve actuator slot 624a such that outlet-side valve 524 is closed or sealed while activating inlet-side valve actuator 622 (not shown in FIG. 8C) in inlet-side valve actuator slot 622a such that inlet-side valve 522 is opened. Opening of inlet-side valve 522 may coincide with or occur shortly after a reverse stroke of piston 545 of piston assembly 542 (e.g., a movement of piston 545 and associated seal surface 546a away from chamber base section 519a, thereby enlarging a volume of pump chamber 525). Accordingly, fluid can flow from upstream pressure dome 532 to pump chamber 525. Alternatively, outlet-side valve 524 may comprise a one-way valve mechanism that permits flow of fluid under normal conditions in one direction (from a fluid container to a patient). Additionally, inlet-side valve 522 may also comprise a one-way valve mechanism permitting flow of fluid in one direction (from a fluid container to a patient) under normal operating conditions. In this configuration, cassette recess 600 would not need to incorporate either outlet-side valve actuator 624 or inlet-side valve actuator 622. Outlet-side valve 524 and inlet-side valve 522 may limit flow of fluid in one direction, but permit flow in an opposite direction in the event fluid pressure overcomes a cracking pressure of the valves.

Continuing with the valve-operated implementation, pumping operation may comprise activating outlet-side valve actuator 624 such that outlet-side valve 524 is open while activating inlet-side valve actuator 622 such that inlet-side valve 522 is closed or sealed. Opening of outlet-side valve 524 may coincide with or occur shortly before a forward stroke of piston 545 (e.g., a movement of piston 545 and associated seal surface 546a toward chamber base section 519a, thereby reducing a volume of pump chamber 525). Thus, fluid can flow from pump chamber 525 to downstream pressure dome 534 and consequently urging fluid out outlet 514.

In certain embodiments, compliant upstream pressure dome 532 and/or downstream pressure dome 534 can address any back pressure issues in the IV set, thereby allowing for an accurate and precise volume of fluid entering pump chamber 525 to be pumped. Additionally, in some embodiments, downstream pressure dome 534 may be larger (e.g., 12 mm) than upstream pressure dome 532 (e.g., 8 mm) so as to address more frequent pressure changes (e.g., temporary or minor occlusions) on the patient side of the IV set, for example.

Figure 8E:
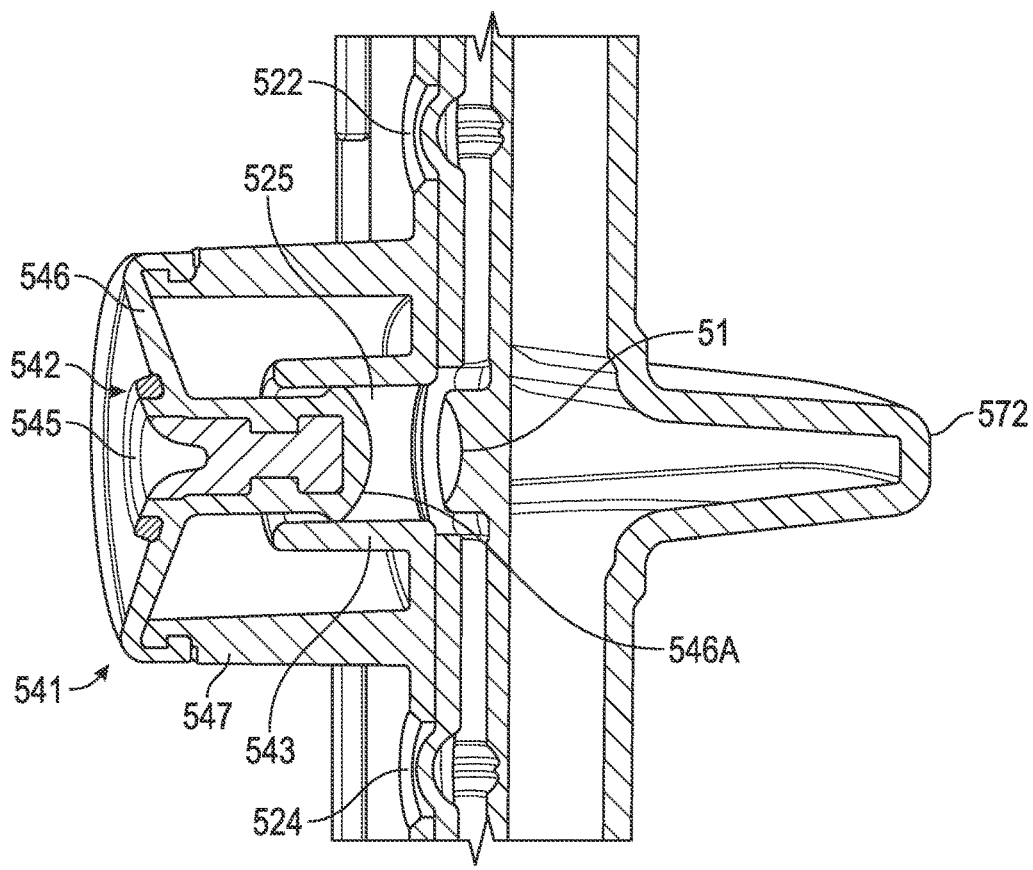
FIG. 8E illustrates an enlarged cross-sectional view of an example of a pump chamber area of a third embodiment disposable IV pump cassette, in accordance with aspects of the present disclosure.

As illustrated in the example of FIGS. 8B and 8E, inlet-side valve 522, pump chamber 525, and outlet-side valve 524 may be longitudinally aligned within cassette body 510, in accordance with certain embodiments. Thus, width and valve operation aspects may be further optimized. It is to be appreciated that orthogonal piston pump techniques as described with respect to cassette 500 and cassette recess 600 can provide repeatedly precise positive displacement of fluid in the pump chamber 525.

Figure 8F:
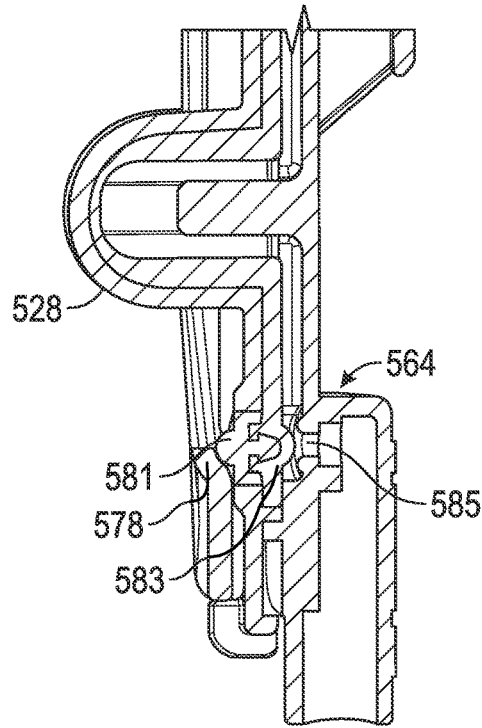
FIG. 8F illustrates an enlarged cross-sectional view of an example of a flow stop valve portion of a third embodiment disposable IV pump cassette, in accordance with aspects of the present disclosure.

FIG. 8F is a cross-sectional view of illustrating aspect of flow stop valve 564. In accordance with certain embodiments, striker 581 is configured to redirect the longitudinally introduced force applied by movement interface-facing slider section 576 into a more generally orthogonal force applied to top membrane portion 583 of flow stop valve 564.

In some aspects, striker 581 can be a hard plastic (e.g., polycarbonate) dome-shaped piece disposed over and co-molded with top membrane portion 583. In other aspects, striker 581 may be constrained in a manner for engagement with top membrane portion 583 (e.g., situated in an aperture above top membrane portion 583). As such, potential sheering forces longitudinally applied directly to the membrane portion 583 of the flow stop valve 564 may be avoided in accordance with certain embodiments. Flow stop valve 564 may include through-hole base portion 585 (e.g., through base portion 519) for releasable engagement with top membrane portion 583. Top membrane portion 583 urged by striker 581 is configured to circumferentially seal through-hole base portion 585 so that fluid flow is restricted to outlet 514 in accordance with certain aspects.

In accordance with some embodiments, a portion of slider 570 may interface with flow stop valve 564 to regulate the fluid flow therethrough. As illustrated in the example of FIG. 8F, the portion of interface-facing slider section 576 does not contact flow stop valve 564 (or in some implementations does not contact flow stop valve 564 sufficiently to activate flow stop valve 564), and flow stop valve 564 operates to allow fluid to flow freely through flow stop valve 564 to outlet 514.

In accordance with certain embodiments, stop valve guard 578 may be positioned proximal to an edge along interface-facing slider section 576 of slider 570 such that when cassette 100 is securely latched or locked within cassette recess 600, stop valve guard 578 is positioned above flow stop valve 564. In this regard, stop valve guard 578 can protect flow stop valve 564 from being inadvertently depressed and activated to restrict fluid flow while cassette 500 is in use.

Figure 9A:
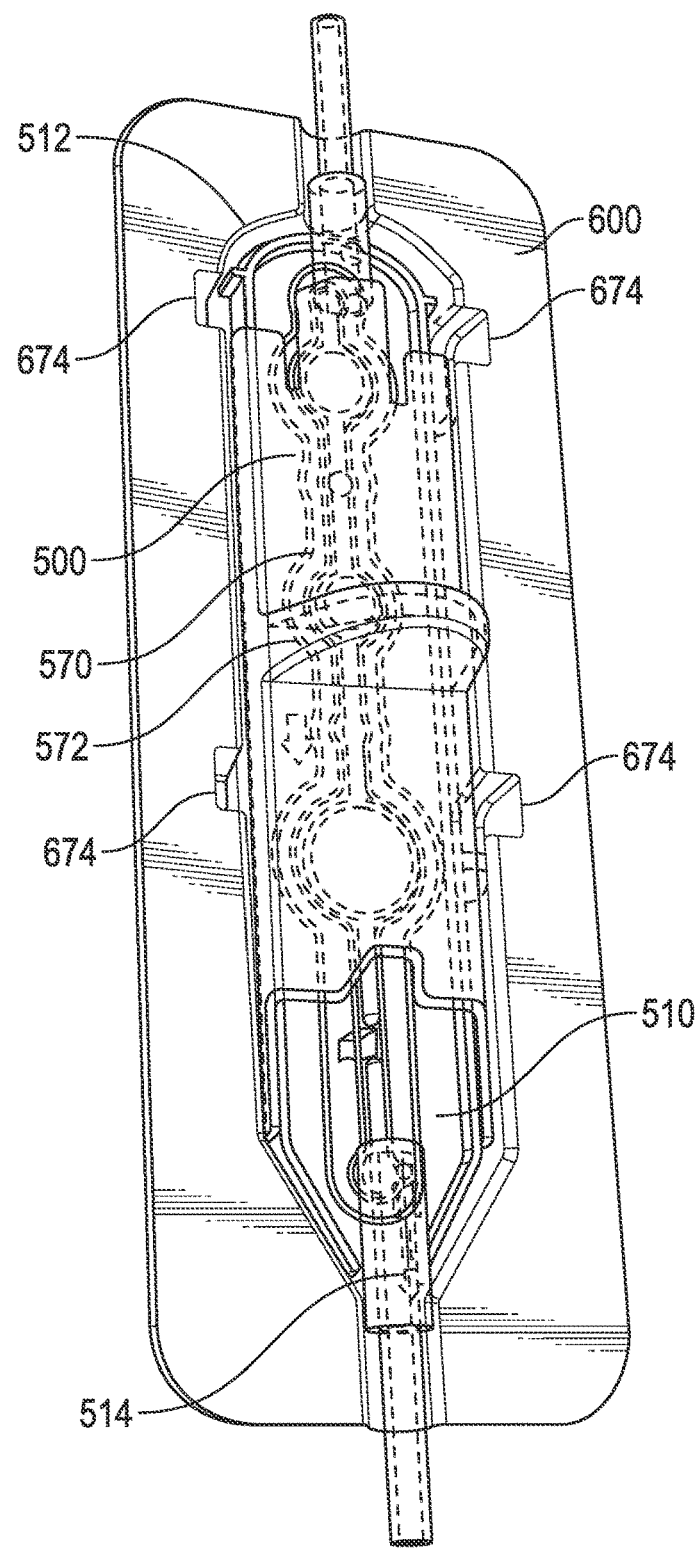
FIG. 9A illustrates perspective views of examples of a third embodiment disposable IV pump cassette and cassette recess, in accordance with aspects of the present disclosure.
Figure 9B:
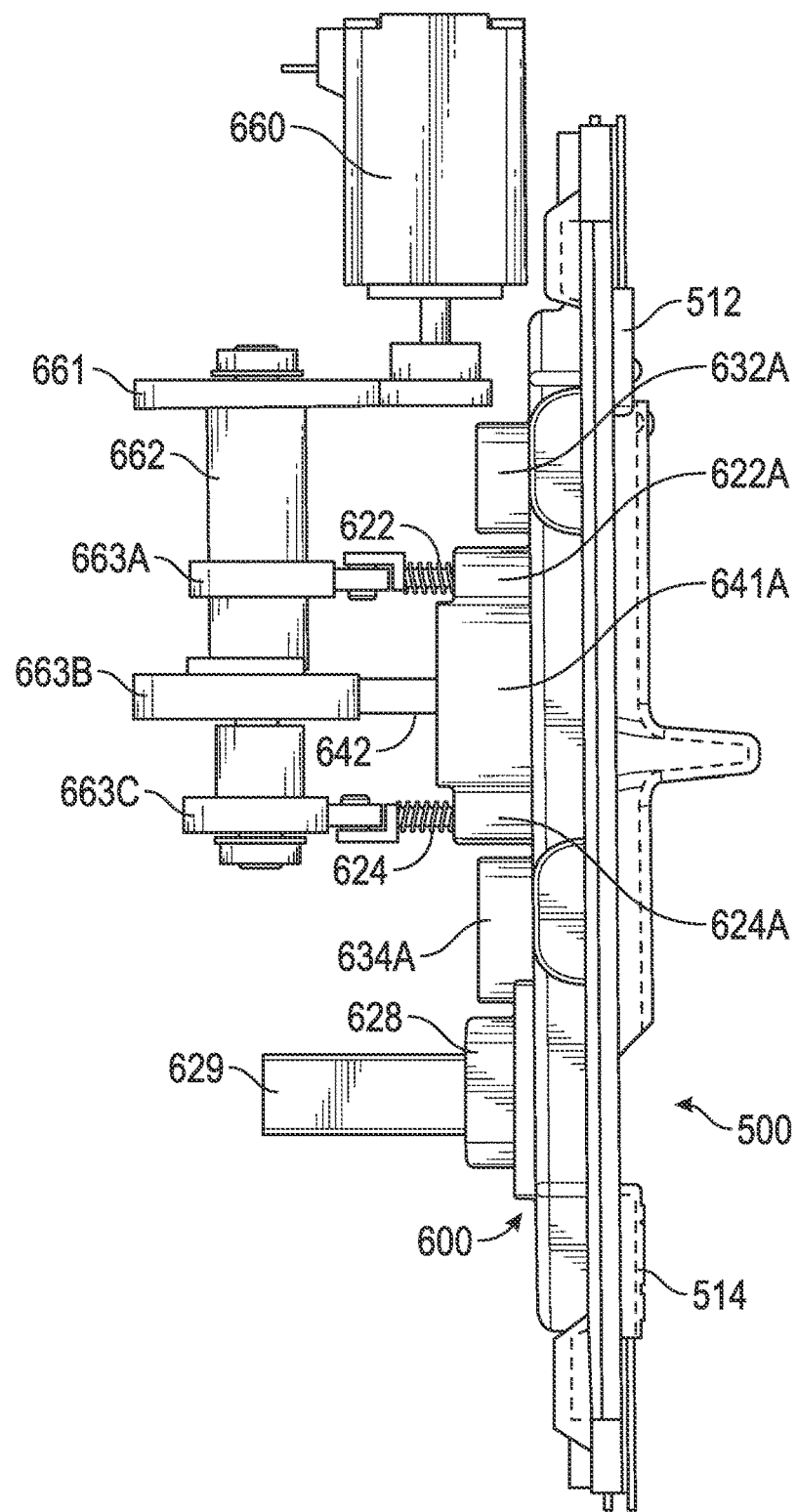
FIG. 9B illustrates side perspective views of examples of a third embodiment disposable IV pump cassette and cassette recess, along with examples of interface structures, in accordance with aspects of the present disclosure.

As illustrated in FIGS. 9A and 9B, slider 570 may be longitudinally articulated such that cassette 500 is latched within cassette recess 600 in accordance with certain orientations of the cassette 500 and cassette recess 600. Cassette recess 600 may include interface structures operable in conjunction with infusion pump systems 10, 11. For example, pump actuator 642 may be configured to provide a force aligned with piston 545 that is substantially orthogonal to a general plane of the interface-facing surface of the pump cassette 500 in certain implementations. In such implementations, pump actuator 642 may engaged with the elastomeric seal member 546 when pump structure 541 is positioned in pump structure recess 641a so that the piston 545 is retracted when the pump actuator 642 performs a reverse stroke (e.g., away from the cassette 500). However, in some implementations, the elastomeric seal member 546 provides sufficient resiliency or counter force to retract piston 545.

In addition to pump structure recess 641a, cassette recess 600 includes inlet-side valve actuator slot 622a and outlet-side valve actuator slot 624a, which are operatively coupled to inlet-side valve actuator 622 and outlet-side valve actuator 624, respectively, in accordance with some embodiments. Pump actuator 642, inlet-side valve actuator 622, and outlet-side valve actuator 624 may be disposed proximate to the back surface of the cassette recess 600, and during operation, portions of pump actuator 642, inlet-side valve actuator 622, and outlet-side valve actuator 624 may extend beyond the back surface (e.g., during a forward stoke of the pump actuator 642 on piston 545 or during a forward stroke of inlet-side valve actuator 622 or outlet-side valve actuator 624 to close inlet-side valve 522 or outlet-side valve 524, respectively).

In accordance with some embodiments, motor 660 operatively coupled to the infusion pump system 10, 11 (e.g., processing unit 12, 13). For example, processing unit 12, 13 may provide signals to control a speed of the rotation of motor 660. Motor 660 may be mechanically coupled to camshaft 662 such that a motor shaft is operative to rotate the camshaft 662. In this regard, the camshaft 662 may be operatively coupled to motor shaft via gear disk 661. However, in other embodiments, motor shaft and camshaft 662 may be one in the same.

In certain embodiments, shaft 662 may include a plurality of cams 663a-c for operating inlet-side valve actuator 622, pump actuator 642, and outlet-side valve actuator 624. Each of cams 663a-c may be formed and/or aligned with respect to the camshaft 662 to provide for proper valve and pump actuator operation as described herein. Accordingly, in certain embodiments, a single camshaft may be utilized in-line to operate both valve and pump actuators (e.g., reducing gearing requirements in comparison to some scotch-yoke pumping configurations). However, it is to be appreciated that other pump drive assemblies are contemplated with cassette 500 and cassette recess 600, in accordance with the present disclosure.

In some embodiments, sensor slot 628 may comprise an air-in-line detector 629. Air-in-line detector 629 may be operable to detect air in the controllable fluid path of cassette 500 via fluid pathway extension member 528, for example. Cassette recess 600 may include various mechanical couplings and operational interfaces, such as but not limited to an inlet-side pressure sensing probe within and/or proximate to inlet-side pressure sensing probe recess 632a and an outlet-side pressure sensing probe within and/or proximate to outlet-side pressure sensing probe recess 634a thereby enabling measurement of in-line pressure and fault isolation to a section of the fluid pathway. For example, inlet-side pressure sensing probe may operably contact upstream pressure dome 532 through a corresponding opening of interface-facing frame portion 516. Similarly, outlet-side pressure sensing probe may operably contact downstream pressure dome 534 through a corresponding opening of frame portion 516.

With reference to the examples of FIGS. 8C, 8D, 9A, and 9B, the x-y positioning of cassette 500 within cassette recess 600 can be constrained by the pump structure 541 and pump structure recess 641a mating interface, as well as fluid pathway extension member 528 and sensor slot 628 mating interface. In this regard, cassette 500 and cassette recess 600 can have two points of contact in the z-axis direction (e.g., an axis through and transverse to a general plane of the interface-facing surface of cassette body 510 of cassette 500 and cassette-facing surface of cassette recess 600) for interlock alignment of the cassette with respect to the x-y positioning of the interface side of the cassette body 510.

It is to be understood that pump structure 541 may have various cross sectional geometries in addition to the circular cross-section support wall illustrated in the example of FIG. 8C and other figures. For example, an external support wall of pump structure 541 may have a triangular, square, or other polygonal cross-section. Alternatively or in addition, the slider 570 may be configured have to tighter tolerances with respect to the x-axis and/or y-axis. For example, the x-axis tolerance may be substantially tight so as to avoid or substantially limit any minor or miniscule rotation of the cassette body 510 during prolonged continuous operation with infusion pump system 10, 11.

During insertion of cassette 500, once cassette body 510 is placed in cassette recess 600, slider 570 can be longitudinally articulated to from a first position to a second position with respect to cassette body 510 (e.g., articulated downwardly in certain implementations; FIG. 9A). In this second position cassette 500 will be latched within cassette recess 600 by virtue of protrusions 574 being engaged with slots 674. In the second position, flow stop valve 564 is aligned under a stop valve guard 578 (e.g., ramped, rounded, or recessed surface) of interface-facing slider section 576 of slider 570 (FIGS. 8B and 8F). When the slider 570 is positioned in the second position, the portion of interface-facing slider section 576 does not contact flow stop valve 564 (or alternatively does not contact flow stop valve 564 sufficiently to activate flow stop valve 564), and flow stop valve 564 operates to allow fluid to flow freely through flow stop valve 564 to outlet 514.

Figure 10A:
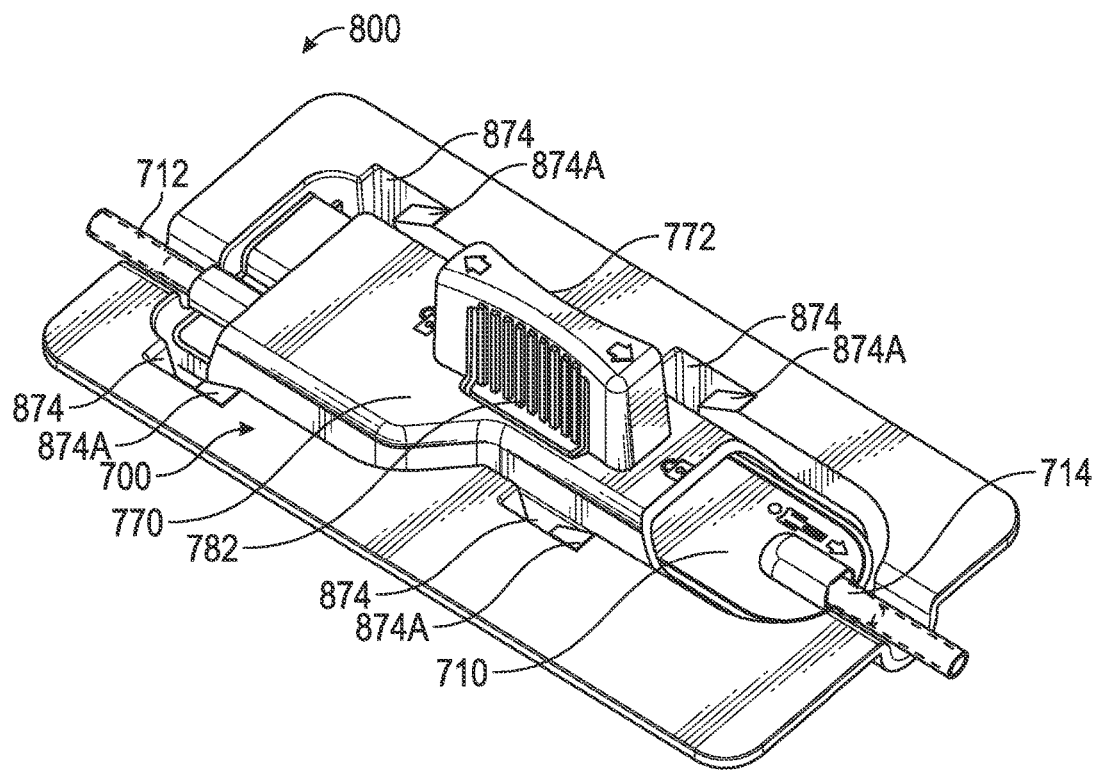
FIG. 10A illustrates perspective views of examples of a fourth embodiment disposable IV pump cassette and cassette recess, in accordance with aspects of the present disclosure.
Figure 10B:
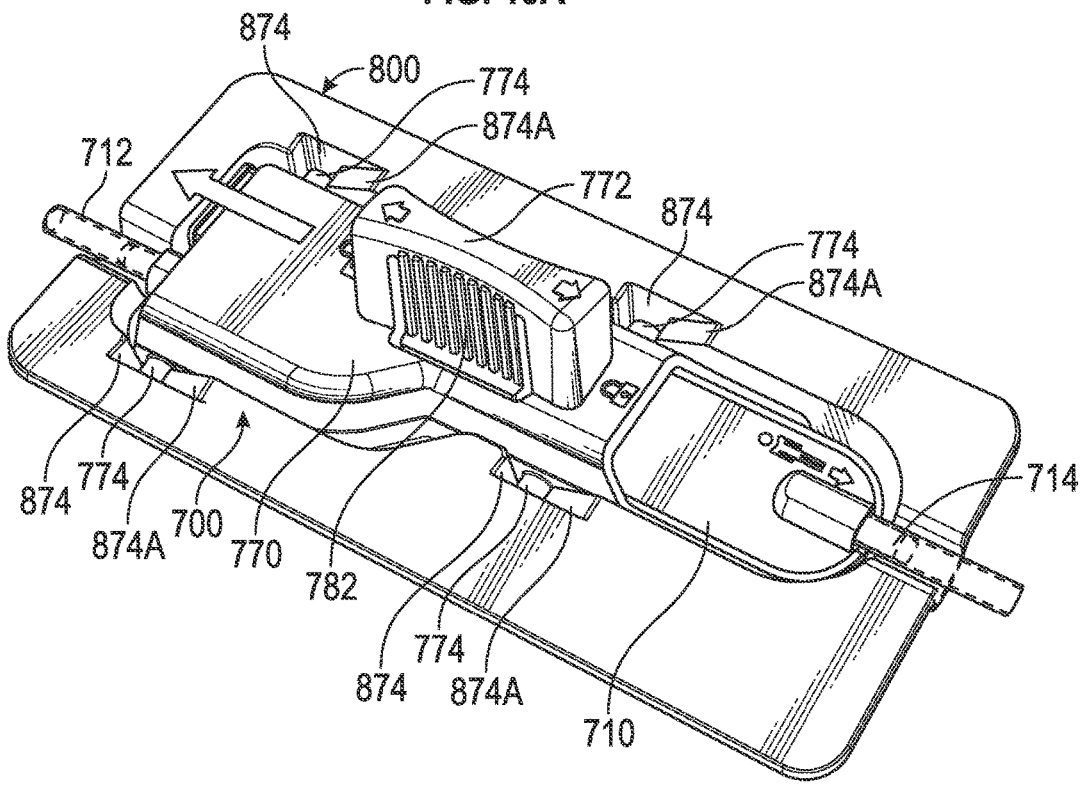
FIG. 10B illustrates perspective views of examples of a fourth embodiment disposable IV pump cassette and cassette recess, in accordance with aspects of the present disclosure.

FIGS. 10A and 10B illustrate examples of cassette 700 within cassette recess 800 in accordance with certain embodiments. Cassette 700 and cassette recess 800 may have similar components and features as like numbered components and features in other example embodiments described herein.

The plurality of protrusions 774 on slider 770 may be engaged with the plurality of slots 874 of cassette recess 800 such that cassette 700 is secured within cassette recess 800 for operation. Cassette recess 800 may configured to receive the pump cassette such that each of the plurality of protrusions 774 may contact a respective flat face ramp portion 874a of each of the plurality of cassette engagement slots 874. The plurality of protrusions 774 may contact and slide along the respective flat face ramp portions 874a to engage with the other portions of the cassette engagement slots 874 (e.g., the deeper portions of the L-channel). In some embodiments, each of the plurality of protrusion 774 may also comprise a flat face portion 774a (FIG. 11A) such that each flat face portion 774a may contact and slide along the respective flat face ramp portion 874a.

Figure 10C:
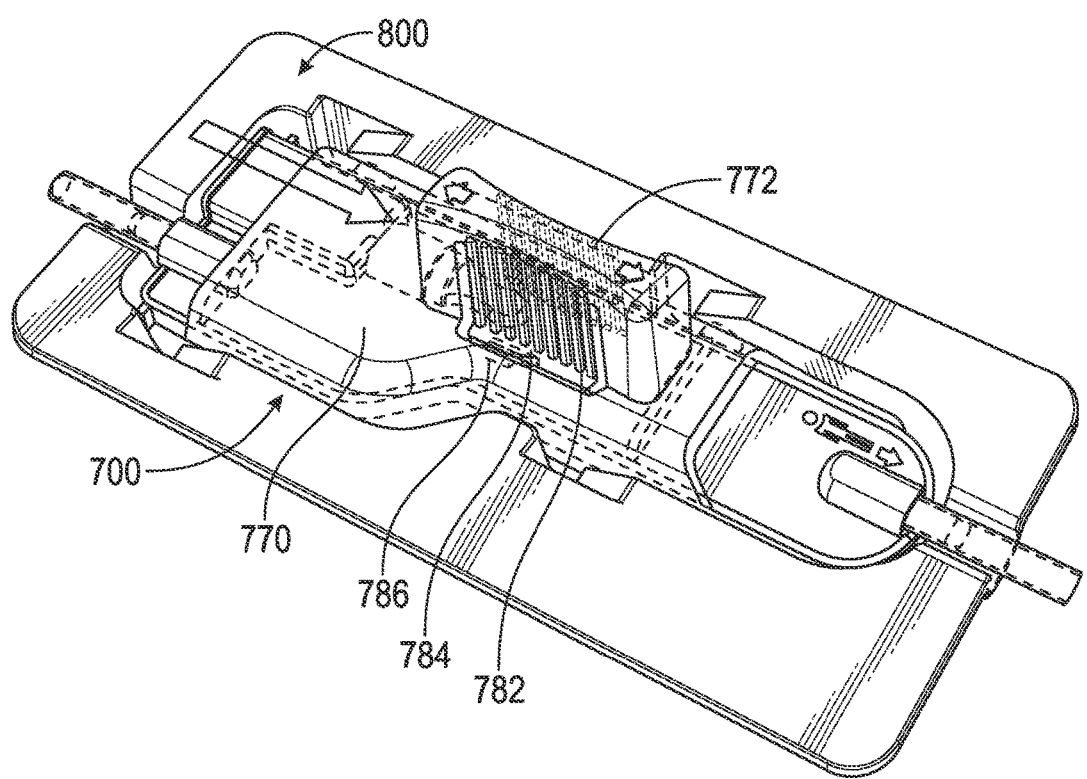
FIG. 10C illustrates perspective views of examples of a fourth embodiment disposable IV pump cassette and cassette recess, in accordance with aspects of the present disclosure.
Figure 11A:
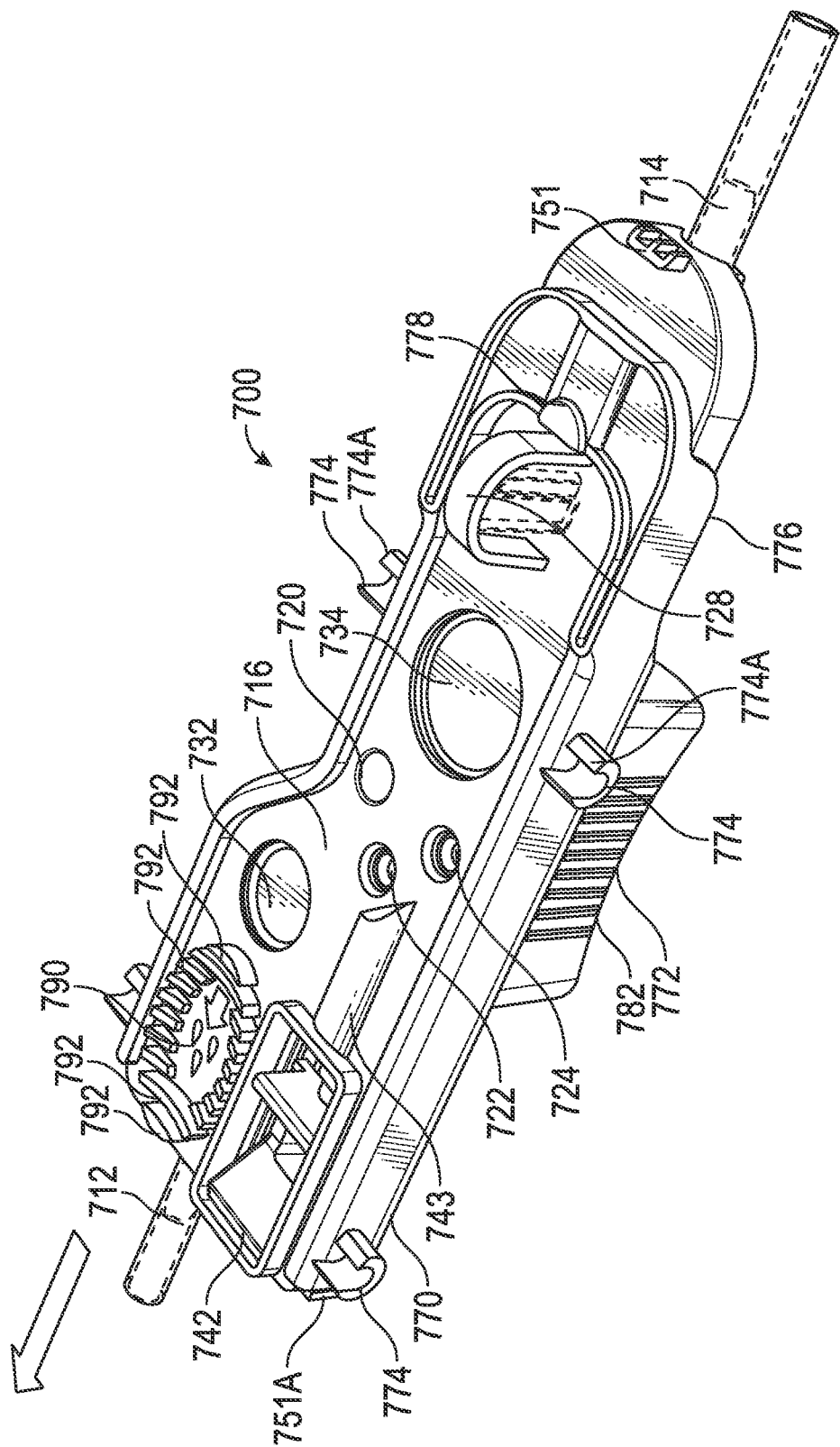
FIG. 11A illustrates perspective views of an example of a fourth embodiment disposable IV pump cassette, in accordance with aspects of the present disclosure.
Figure 11B:
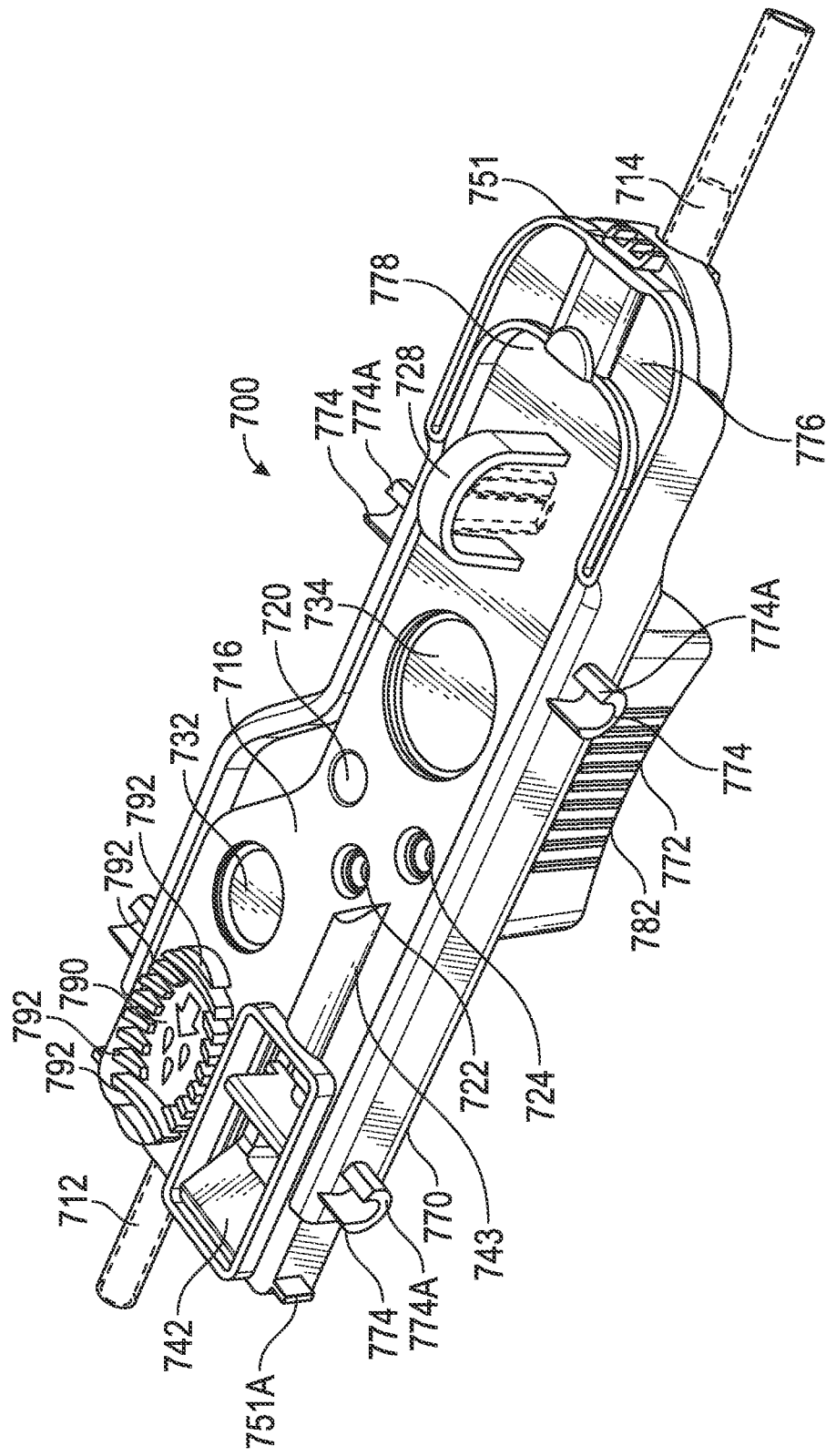
FIG. 11B illustrates perspective views of an example of a fourth embodiment disposable IV pump cassette, in accordance with aspects of the present disclosure.

With reference to the example cassette engagement positions of FIGS. 10A-10C, other aspects of cassette 700 are provided with additional reference to the examples of FIGS. 11A and 11B. For example, flow stop valve 764 may be configured to restrict and/or regulate fluid flow proximal to outlet 714 of cassette body 710. In some embodiments, slider 770 may be articulated from a first position (e.g., slider 770 oriented toward top of cassette body 710) to a second position (e.g., slider 770 oriented toward bottom of cassette body 710) after priming and/or staging procedures have been completed and cassette 700 is to be installed into cassette recess 800. During insertion of cassette 700, cassette body 710 may be generally aligned with cassette recess 800 and the flat face portions 774a of the plurality of protrusions 774 may contact the respective flat face ramp portions 874a of the cassette engagement slots 874.

As illustrated in the example of FIG. 10C, slider 770 may be a lockable slider in the second position in accordance with certain embodiments. For example, slider 770 may include slider grip 772 having a flexible portion 782 that is configured to allow the slider to change from a locked state to an unlocked state along such that the slider 770 can articulate a longitudinal path. Flexible portion 782 may include a polygon tab 784 that interfaces with a body tab 786 disposed on a slider-facing side of cassette body 710 when the flexible portion 782 is in an unbiased state (e.g., not being squeezed or pinched by the user). For example, polygon tab 784 may have a square face that contacts a respective square face of body tab 786 when the slider 770 is in the second position such that the polygon tab 784 is aligned below the body tab 786. Thus, to articulate slider 770 from the second position to the first position (e.g., articulating the slider 770 upwardly with respect to the cassette body 710), flexible portion 782 must be biased (e.g., squeezed or pinched by the user), such that the polygon tab 784 is no longer aligned below nor is obstructed by the body tab 786. Hence, the slider 770 can freely articulate upwardly to the first position. Flexible portion 782 may be capable or being biased by one or more slots disposed on the slider grip 772, for example.

Polygon tab 784 may include an angled face that is aligned above the body tab 786 when the slider 770 is in the first position. Thus, when slider 770 is articulated from the first position to the second position (e.g., articulating the slider 770 downwardly with respect to the cassette body 710), the polygon tab 784 will not be obstructed by the body tab 786 and the angled face of the polygon tab 784 will cause the polygon tab 784 to slide around the body tab and bias the flexible portion 782. When the polygon tab 784 extends beyond the body tab while the slider 770 is being longitudinally articulated, the flexible portion 782 may snap back to the unbiased state and generate an audible sound (e.g., a click) and or vibration in the slider grip 772 when the flexible portion 782 contact the body tab 786, for example, enabling the user or caregiver to infer that the slider 770 has reached the second position and is now locked.

It is to be appreciated that, in other embodiments, slider 770 may be configured to be lockable at multiple lockable positions along a longitudinal path with respect to the rigid body for which the slider 770 articulates, such as but not limited to the first position and one or more intermediate positions. Such embodiments may be configured by variation of the size and/or shape of the polygon tab 784 and the body tab 786, for example. However, other techniques for locking and/or biasing the various slider 770 and slider grip 772 embodiments may be used as would be understood given the benefit of the present disclosure.

In accordance with certain embodiments, slider grip 772 may be generally elongate and longitudinally aligned parallel to the two opposing edge sections of cassette body 710. For example, a width of the slider grip 772 may be less than a length of the slider grip 772, and the slider grip 772 may be positioned in a relative center of cassette 700 to enhance balance and alignment features during the process of inserting the cassette 700 into cassette recess 800.

With reference to FIGS. 11A and 11B, slider 770 can be articulated between the first position and second position with respect to cassette body 710 such that flow stop valve 764 is actuated by one or more portions of the slider 770. For example, flow stop valve 764 may be actuated by contact with interface-facing slider section 776 when the slider 770 is in the first position. Thus, fluid flow through the fluid pathway may be occluded in the first position. Flow stop valve 764 may be activated by contact with interface-facing slider section 776 when the slider 770 is in the first position. Thus, fluid flow through the fluid pathway may be occluded in the first position. When the slider 770 is positioned in the second position, a portion of interface-facing slider section 776 (e.g., stop valve guard 778) does not contact flow stop valve 764 (or alternatively does not contact flow stop valve 764 sufficiently to activate flow stop valve 764), and flow stop valve 764 operates to allow fluid to flow freely through flow stop valve 764 to outlet 714.

Furthermore, slider 770 may be articulated between the first position and the second position when cassette 700 is not engaged with cassette recess 800 with the aid of grip feature 790. In certain embodiments, grip feature 790 may be arranged on an exterior surface of interface-facing frame portion 716 of cassette body 710, and may be defined in part by a plurality ribs 792 extending from the exterior surface of the interface-facing portion 716. However, in some embodiments, grip feature 790 may include a recessed portion extending into the exterior surface of interface-facing frame portion 716 (e.g., an indentation on the exterior surface that does not extend beyond a thickness of interface-facing frame portion 716). Grip feature 790 may be generally oval-shaped indicative of a thumb or finger support for a user or caregiver, for example.

In an example method, while holding cassette 700, a user or caregiver may place a thumb of his or her first hand on grip feature 790 and longitudinally articulate, with one or more fingers of his or her first hand, for example, slider 770 of cassette 700 with respect to the cassette body 710 from a first position in which flow stop valve 764 occludes fluid flow to a second position in which flow stop valve 764 allows fluid flow. As noted herein, slider 770 of cassette 700 may be in an unlocked state in accordance with certain embodiments when the slider 770 is in the first position such that the user would not need to pinch the flexible portion 782 of the slider grip 772 (or otherwise apply a force other than a longitudinal force to the slider 770) to articulate the slider 770 from the first position to the second position. In embodiments where the first position is lockable, the flexible portion 782 of the slider grip 772 may be biased to unlock the slider 770 with the one or more finger of the first hand or one or more fingers and a thumb of the second hand, for example.

FIGS. 12A and 12B illustrate examples of a disposable IV pump cassette 900 and corresponding cassette recess 1000 of an interface module. In accordance with certain embodiments, cassette 900 may comprise a cassette body 910 and a slider 970. Cassette 900 may include certain may include certain visual indicators related to operation aspects of the cassette and the infusion pump system in general. For example, cassette may include identifiable images such as fluid drops indicating position of slider 970 for free-flow (e.g., flow stop valve 964 in an open position) and a patient figure proximal to outlet 914. In accordance with some aspects, one or more cassette-seated sensors may be disposed within the cassette recess 1000 so as to inform central processing unit 12 that the cassette is locked or secured into place within the cassette recess 1000 or seat. For example, cassette recess may include a window 1004 (or aperture) such that cassette identifier 902 (FIG. 13A) can be scanned. Cassette identifier 902 may include various information such as, but not limited to, a manufacturer, type, and use parameters of cassette 900. Moreover, cassette identifier 902 may be disposed on a top half of the exterior surface of interface-facing frame portion 916 with respect to gravity during use. Thus, a bottom half of the exterior surface of interface-facing frame portion 916 can be reserved for pump drive assembly and flow stop valve features, in accordance with certain embodiments.

Slider 970 can be fixably and slidably engaged with cassette body 910 such that slider 970 may articulate longitudinally with respect to cassette body 910, but will be constrained within range of sliding motion such that the slider remains coupled to the cassette body 910. Slider 970 may be formed from rigid plastic or polymer material having lubricating characteristics (e.g., incorporating silicon or polytetrafluoroethylene (PTFE) additives), and is clear or translucent in accordance with certain embodiment. In some embodiments, slider 970 may be polycarbonate. In accordance with certain aspects, slider 970 may be lockable at one or more positions, and may include a slider grip 972 for unlocking and articulating slider 970. Slider 970 may also include a plurality of protrusion 974 or lugs that are configured to mate and be releasably lockable with a plurality of slots 1074 of the cassette recess 1000 (e.g., L-shaped locking channels).

Each of the plurality of protrusion 974 may also comprise a flat face portion 974a that is configured to interface with a respective flat face ramp portions 1074a of the cassette engagement slots 1074. In this regard, cassette 900 can be self-guided and self-latched into the cassette recess 1000. Accordingly, a door or lever action is not required in order to retain the cassette 900 within the cassette recess 1000.

Figure 12C:
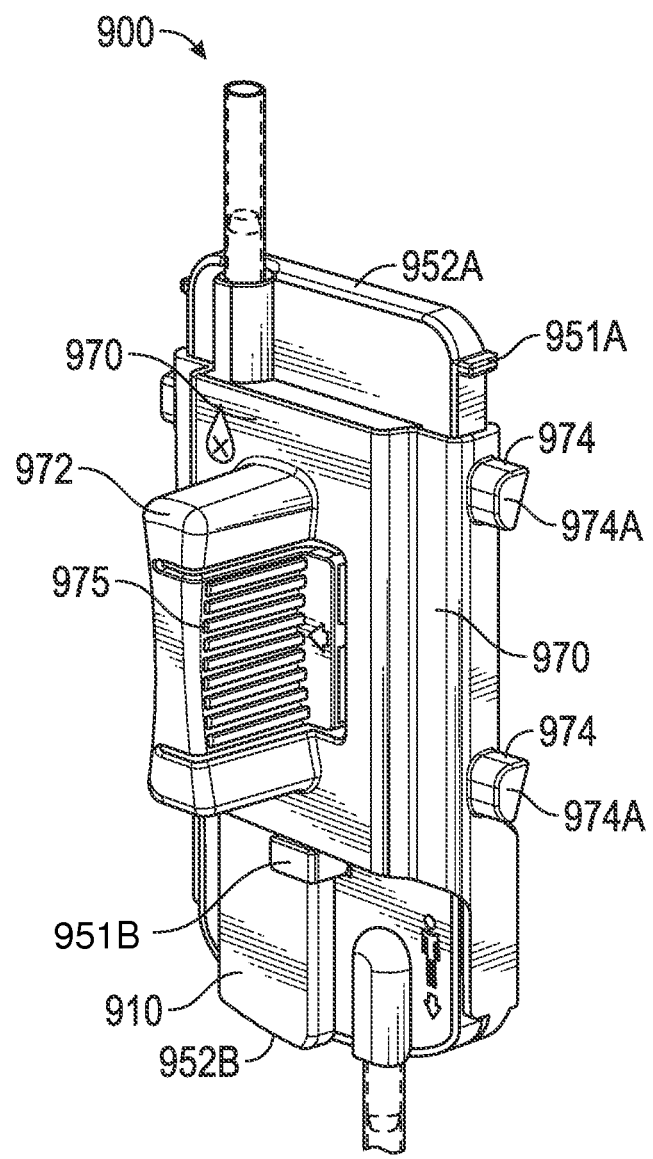
FIG. 12C illustrates a front perspective view of an example of a fifth embodiment disposable IV pump cassette, in accordance with aspects of the present disclosure.
Figure 13A:
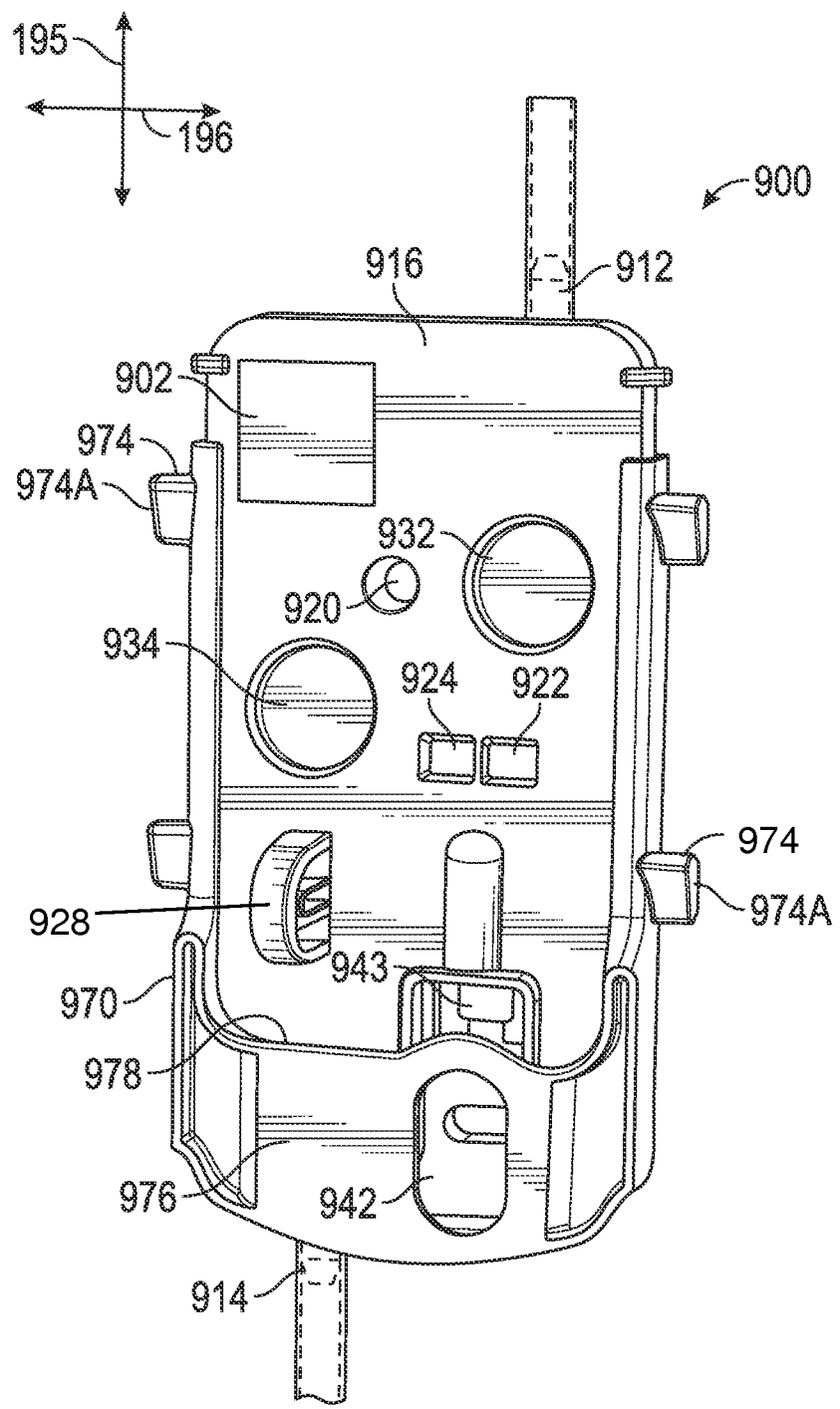
FIG. 13A illustrates a perspective view of an example of a fifth embodiment disposable IV pump cassette, in accordance with aspects of the present disclosure.
Figure 13B:
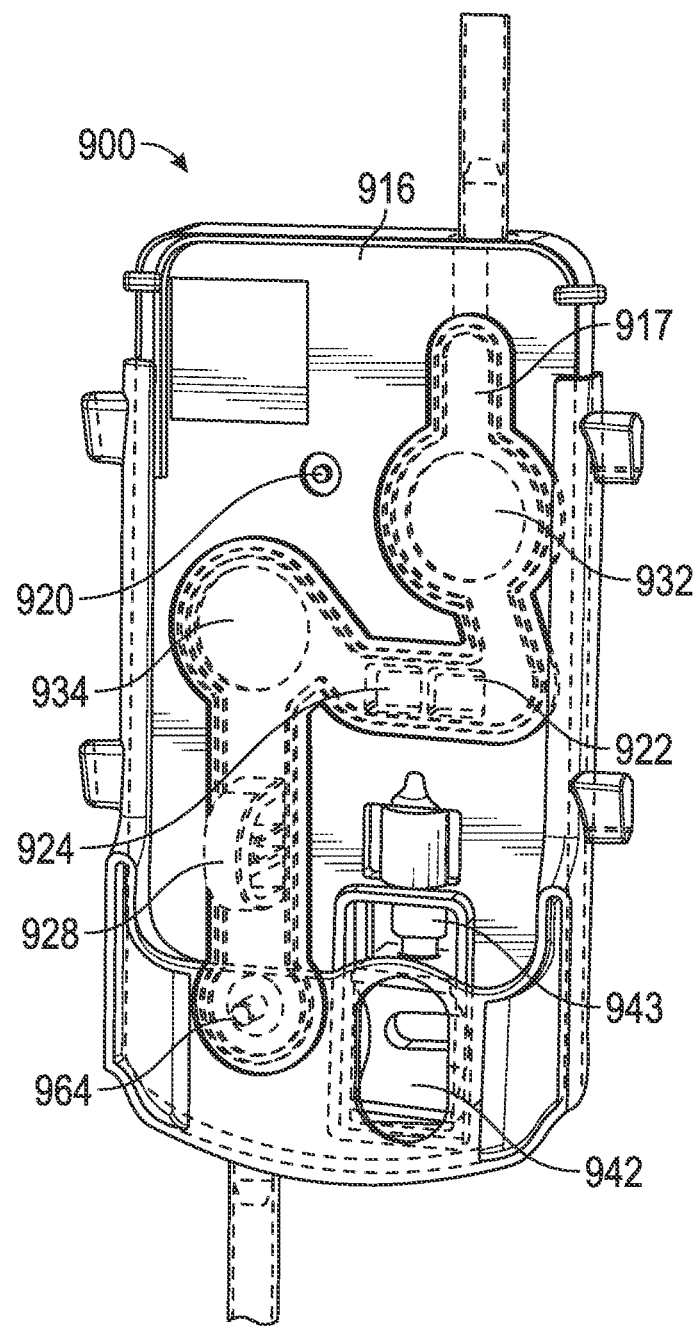
FIG. 13B illustrates a perspective view of an example of a fifth embodiment disposable IV pump cassette, in accordance with aspects of the present disclosure.

The plurality of protrusions 974 may be disposed at various locations on slider 970. As illustrated in the examples of FIGS. 12C and 13A, slider 970 may comprise a first pair of protrusions 974 disposed on opposing edges proximal to a top of slider 970, and a second pair of protrusions 974 disposed on opposing edges distal from the top of slider 970. The first pair of protrusions 974 may be spaced apart a same distance as the second pair of protrusions 974 in certain embodiments. Cassette 900 may include a different top edge shape 952a (e.g., generally straight) as compared to a bottom edge shape 952b (e.g., arcuate or partially rounded). In this regard, cassette 900 orientation within cassette recess 1000 (along with non-vertically aligned inlet recess 1012 and outlet recess 1014) is clear to a user or caregiver such that a cassette 900 is not inadvertently installed (or when being primed) in an inverted manner. Additionally, perimeter edges of cassette 900 and corresponding perimeter edges of cassette recess 1000 may include rounded corners and opposing and/or parallel straight longitudinal edges, in accordance with certain example aspects.

Such perimeter edge features may provide benefit by enabling visual identification as well as prohibiting improper orientation or seating of cassette 900 with a corresponding cassette recess 1000. Additionally, minimizing a size of cassette 900 and optimizing a surface area of one or more corresponding cassette recess 1000 may be achieved using arcuate perimeter edge configurations.

Additionally, an overall size of cassette 900 and cassette recess 1000 may be reduced, in accordance with some aspects. For example, in certain embodiments, cassette body 910 may extended longitudinally a length between 70 mm and 90 mm. For orientation reference with respect to the various views of the examples illustrated of FIGS. 12A through 14E, longitudinal axis or y-axis 195, latitudinal axis or x-axis 196, and depth axis or z-axis 197 are provided as a reference on certain figures (e.g., FIGS. 12D, 13A, and 14A-14D).

Figure 12D:
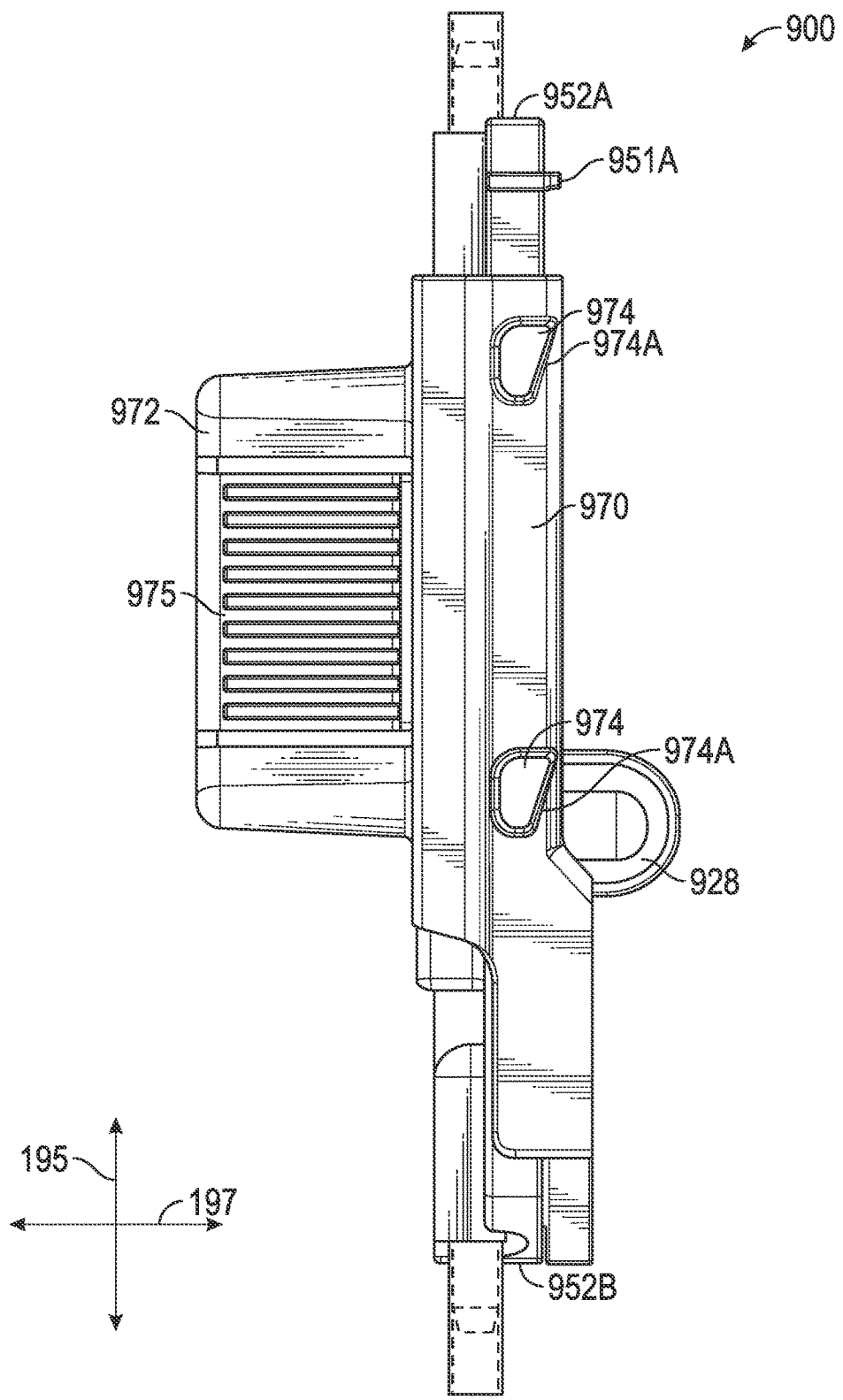
FIG. 12D illustrates a side perspective view of an example of a fifth embodiment disposable IV pump cassette, in accordance with aspects of the present disclosure.

In this regard, depth aspects of cassette 900 is shown in the example of FIG. 12D. For example, in certain embodiments, cassette body 910, or a substantial portion thereof, may extend depth between 5 mm and 10 mm. Fluid pathway extension member 928 may further extend between 8 mm to 10 mm. In certain aspects, slider grip 972 may extend between 9 mm to 16 mm from cassette body 910. It is to be appreciated that the process of cleaning of inlet recess 1012, outlet recess 1014, and cassette recess 1000 is made efficient in the shallow recess configuration in accordance with certain embodiments should any fluid or debris accumulate within cassette recess 1000. The shallow recess configuration of cassette recess 1000, and associated longitudinal alignment of cassette 900 such that a smaller of volumetric dimensions of cassette 900 (e.g., depth being smaller than length and width in certain embodiments) further enables additional space for arrangement of mechanical couplings and operational interfaces and optimizes the overall space requirements of cassette recess 1000 and infusion pump system in general.

Various types, placement, and orientations of the plurality of protrusions 974 disposed on slider 970 are contemplated in the present disclosure. Aspects of the various cassette-coupling techniques illustrated in the example cassette embodiments 100, 300, 500, 700 described herein may be further combined and arranged into additional configurations suitable for specific implementations given the benefit of the present disclosure.

Moreover, in accordance with certain aspects, features of cassette recess 1000 are designed to avoid wear down and/or risk of malfunction. For example, the plurality of slots 1074 arranged within cassette recess 1000 may be devoid of any movable latching mechanism in certain embodiments as such movable latching mechanisms may be susceptible to excessive wear and mechanical failure over repeated use with multiple disposable IV cassettes 900.

In operation, cassette 900 can be loaded directly into cassette recess 1000. In this regard, the direct loading of the cassette 900 will enable avoidance of sheer forces that might otherwise be applied to the sensors, alignment features, and other engaging interfaces of cassette-facing surface 1016 of cassette recess 1000 from interaction with the interface-facing side of cassette body 910 as it is loaded into cassette recess 1000. It is to be understood that modification to the various features of cassette 900 can be made to accommodate the various cassette-coupling techniques disclosed herein.

Cassette body 910 may comprise interface-facing frame portion 916 and slider-facing base portion 919 (FIGS. 12E, 13A, and 13B) with membrane 917 disposed substantially therebetween. Portions of membrane 917 may extend through or be accessible from some openings of frame portion 916 (e.g., upstream pressure dome 932, downstream pressure dome 934, inlet-side valve 922, and outlet-side valve 924). In accordance with certain embodiments, membrane 917 can be a compliant material co-molded to the frame portion 916 and sealingly engaged with base portion 919 for defining a fluid pathway through cassette body 910 from inlet 912 to outlet 914. Mating edges of frame portion 916 and base portion 919 may be connected by fusing, welding, gluing, or the like. Membrane 917 and base portion 919 may further define a plurality of other features, some of which may be accessed through openings in frame portion 916.

Frame portion 916, membrane 917, and/or base portion 919 may define features in or along the fluid pathway, in accordance with certain embodiments. For example, beginning from inlet 912, the fluid pathway may include features such as, but not limited to, upstream pressure dome 932 (e.g., an inlet-side compliant reservoir), inlet-side valve 922, pump chamber 925, outlet-side valve 924, downstream pressure dome 934 (e.g., an outlet-side compliant reservoir), fluid pathway extension member 928, and flow stop valve 964. Other features that are not in or along the fluid pathway, but are disposed on cassette body 910, may include positioning port 920 and slider stopper 951. With respect to extension member 928, a portion of the fluid pathway can be extended away or protrude orthogonally from the generally flat and planar exterior surface of interface-facing frame portion 916 so as to make the fluid in the fluid pathway available for certain detection techniques performed by infusion pump system 10, 11. As illustrated in the example of FIG. 12D, for example, fluid pathway extension member 928 may be formed from orthogonally extending portions of frame portion 916, membrane 917, and/or base portion 919.

Figure 12E:
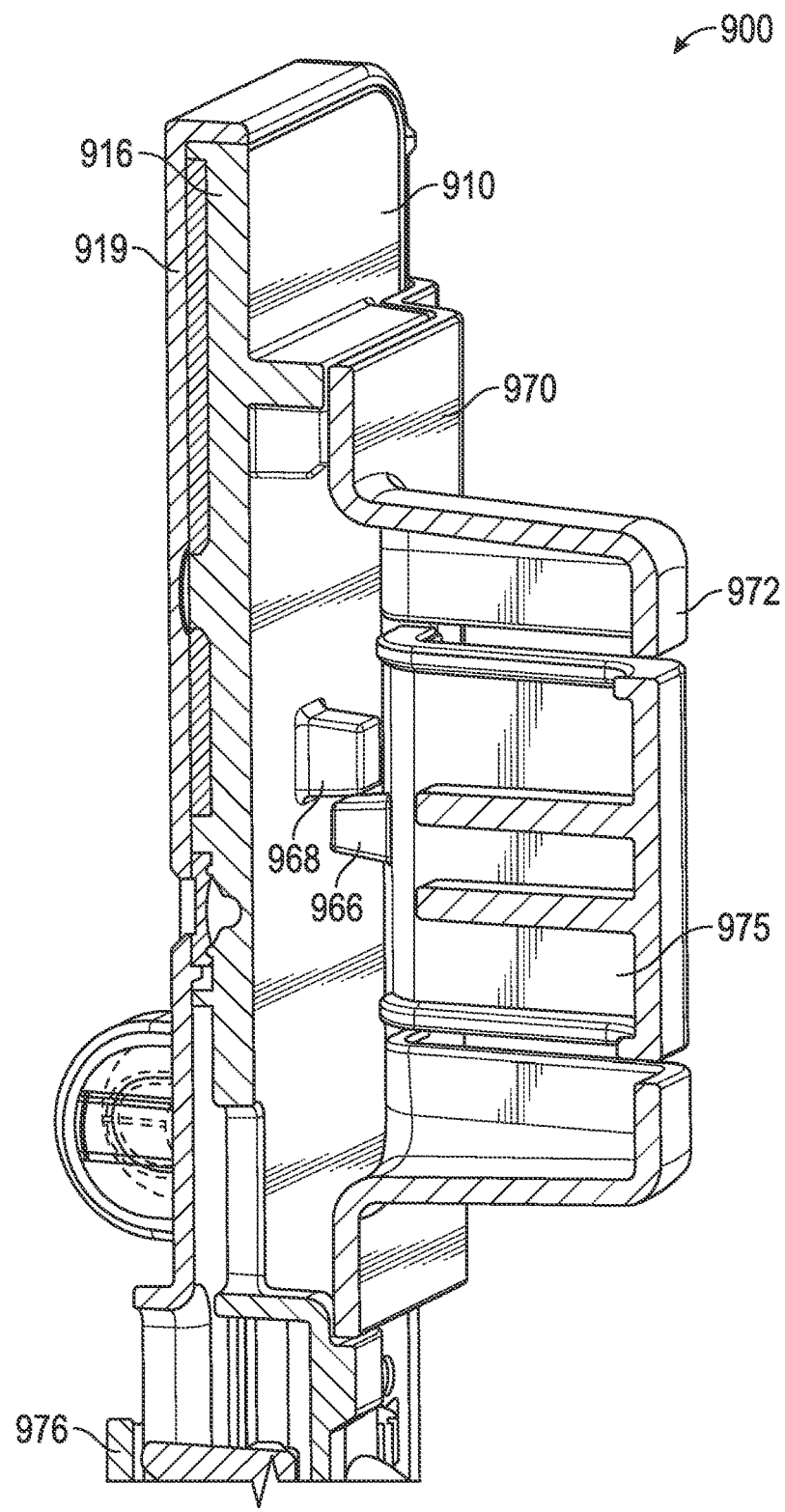
FIG. 12E illustrates an enlarged cross-sectional perspective view of an example of a fifth embodiment disposable IV pump cassette, in accordance with aspects of the present disclosure.

With reference to the examples of FIGS. 12C, 12D, and 12E (illustrating an enlarged, cross-sectional perspective view of cassette 900), slider 970 may be a lockable slider in a first and second position in accordance with certain embodiments. Thus, slider 970 may be configured to articulate such that the slider 970 is movably fixable at one or more positions with respect to cassette body 910. For example, slider 970 may include slider grip 972 having a flexible portion 975 that is configured to allow the slider to change from a locked state to an unlocked state such that the slider 970 can articulate along a longitudinal path. The longitudinal path of slider 970 may be constrained by one or more slider stoppers, for example top slider stopper 951a and bottom slider stopper 951b. Flexible portion 975 may include a slider grip tab 966 that interfaces with a body tab 968 disposed on a slider-facing side of cassette body 910 when the flexible portion 975 is in an unbiased state (e.g., not being squeezed or pinched by the user). For example, slider grip tab 966 may have a square face that contacts a respective square face of body tab 968 when the slider 970 is in the second position such that the slider grip tab 966 is aligned below the body tab 968. Thus, to articulate slider 970 from the second position to the first position (e.g., articulating the slider 970 upwardly with respect to the cassette body 910), flexible portion 975 must be biased (e.g., squeezed or pinched by the user), such that the slider grip tab 966 is no longer aligned below nor is obstructed by the body tab 968. Hence, the slider 970 can freely articulate upwardly to the first position. Flexible portion 975 may be capable or being biased by one or more slots disposed on the slider grip 972, for example.

Slider grip tab 966 may also include a square face that is aligned above the body tab 968 when the slider 970 is in the first position. Thus, to articulate slider 970 from the first position to the second position (e.g., articulating the slider 970 downwardly with respect to the cassette body 910), the flexible portion 975 must be biased (e.g., squeezed or pinched by the user), such that the slider grip tab 966 is no longer aligned above nor is obstructed by the body tab 968. Hence, the slider 970 can freely articulate downwardly to the second position. In some embodiments, when the slider grip tab 966 extends beyond the body tab while the slider 970 is being longitudinally articulated, and the user relates pressure to the flexible portion 975 (e.g., whereby the slider grip tab 966 and the body tab 968 are parallel aligned and contacting each other on respective sides), the flexible portion 975 may snap back to the unbiased state and generate an audible sound (e.g., a click) and/or vibration in the slider grip 972 when the flexible portion 975 contact the body tab 968. In this regard, the user or caregiver can infer that the slider 970 has reached the first or second position and is now locked.

It is to be appreciated that, in other embodiments, slider 970 may be configured to be lockable at multiple lockable positions along a longitudinal path with respect to the rigid body for which the slider 970 articulates, such as but not limited one or more intermediate positions. Such embodiments may be configured by variation of the size and/or shape of the slider grip tab 966 and the body tab 968, for example. However, other techniques for locking and/or biasing the various slider 970 and slider grip 972 embodiments may be used as would be understood given the benefit of the present disclosure.

In accordance with certain embodiments, slider grip 972 may be generally elongate and longitudinally aligned parallel to the two opposing edge sections of cassette body 910.

For example, a width of the slider grip 972 may be less than a length of the slider grip 972, and the slider grip 972 may be positioned in a relative center of cassette 900 (e.g., particularly when locked in the second position) to enhance balance and alignment features during the process of inserting the cassette 900 into cassette recess 1000.

In accordance with certain embodiments, membrane 917 may be formed from a thermoplastic elastomer (TPE). Characteristics of certain TPEs can enable effective co-molding with other materials, for example, polycarbonate. Accordingly, in some embodiments, membrane 917 may be co-molded to frame portion 916 and a striker may be co-molded to a portion of membrane 917 defining a flow stop valve 964. However, in some embodiments, membrane 917 can be formed from silicon, a silicon-based compound, an elastomeric material suitably compliant for fluid flow, or the like.

In accordance with certain embodiments, interface-facing frame portion 916 and slider-facing base portion 919 may be formed from a rigid plastic such as, but not limited, a polycarbonate. Additionally, the rigid plastic of frame portion 916 and base portion 919 may be clear or translucent. The material of membrane 917 (e.g., TPE or other compliant material) and rigid plastic slider 970 may also be clear or translucent, thereby allowing a user or caregiver to readily observe fluid passage through a substantial portion of the fluid pathway of cassette body 910. In some embodiments, the fluid pathway portion of cassette body 910 will be clear or translucent, and other portions will be frosted so as to direct a user or caregiver's attention to the fluid pathway.

In some implementations, slider 970, base portion 919, and membrane 917 may be clear or translucent (or at least some portions along the fluid pathway), and the frame portion 916 may not be translucent. For example, the frame portion 916 may be colored in a manner so as to contrast against a color or tint of the fluid expected to be used with cassette 900. In some embodiments, a lens area may be disposed on base portion 919 and/or slider 970.

Figure 13C:
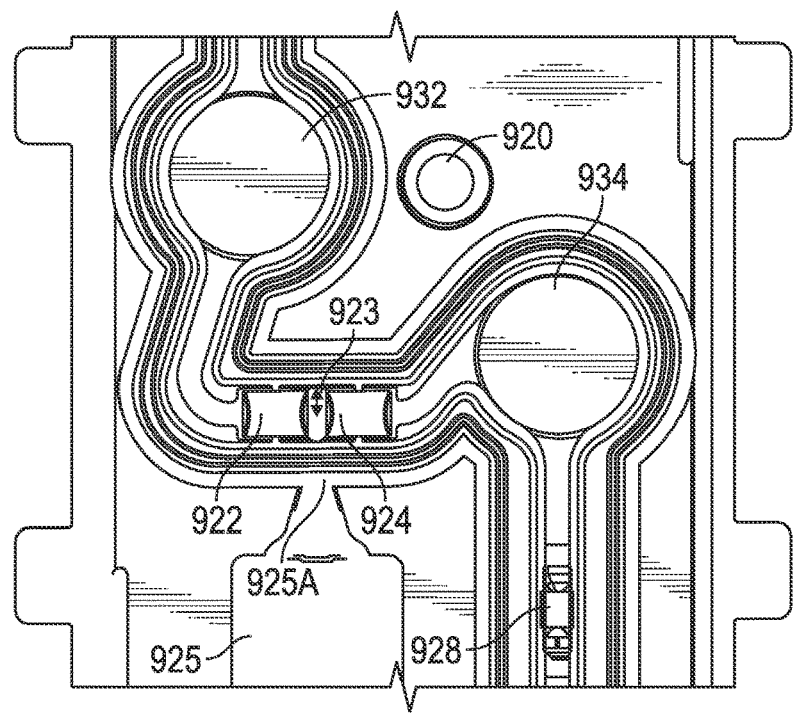
FIG. 13C illustrates an enlarged cross-sectional perspective view of an example of a fifth embodiment disposable IV pump cassette, in accordance with aspects of the present disclosure.
Figure 13D:
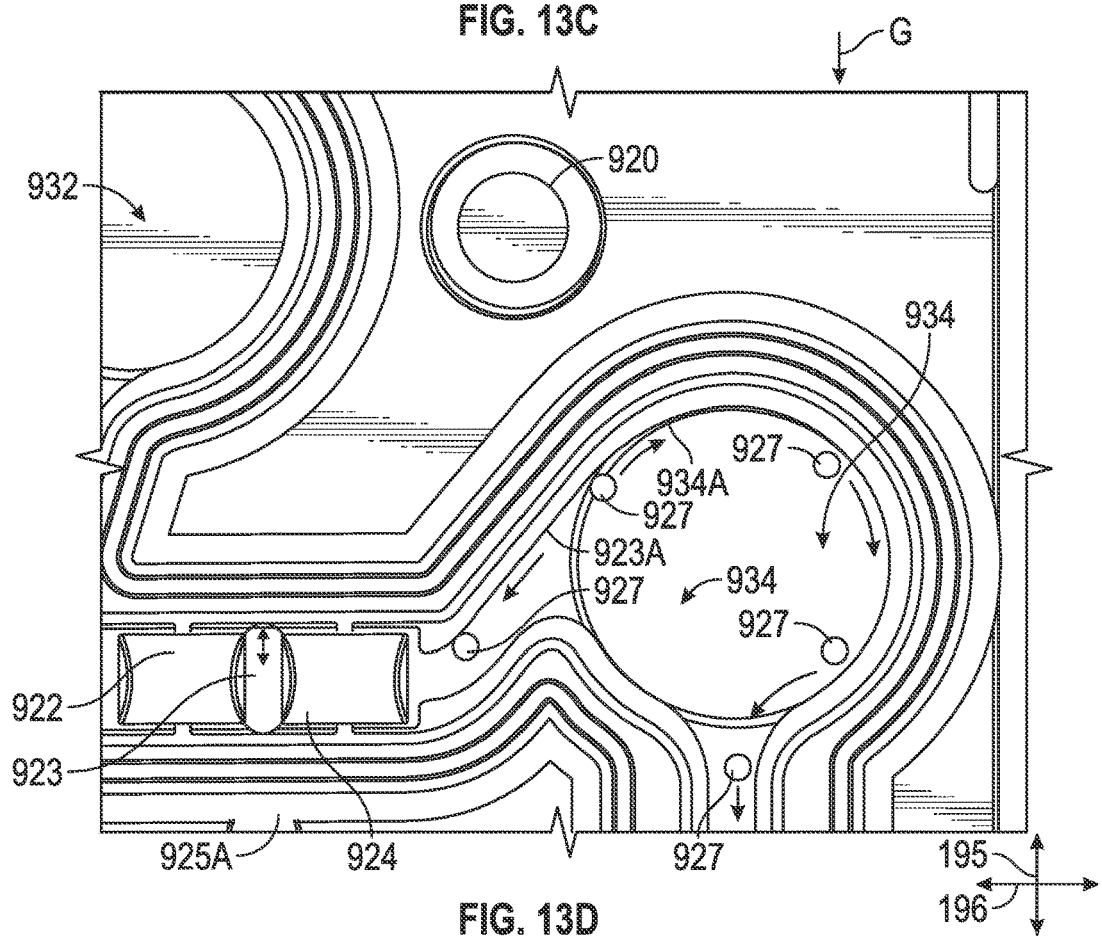
FIG. 13D illustrates an enlarged cross-sectional perspective view of an example of a fifth embodiment disposable IV pump cassette, in accordance with aspects of the present disclosure.
Figure 13E:
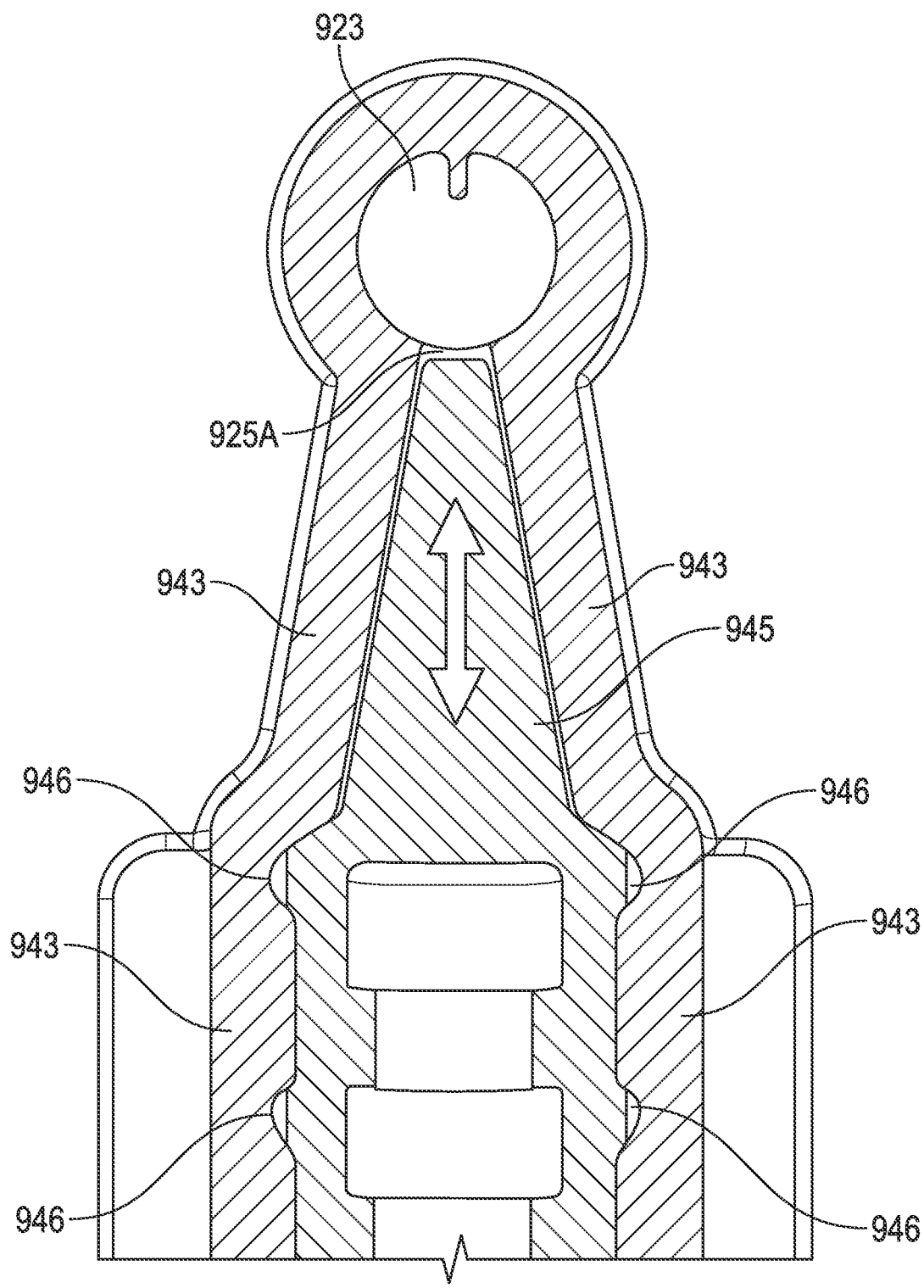
FIG. 13E illustrates an enlarged cross-sectional perspective view of an example of a fifth embodiment disposable IV pump cassette, in accordance with aspects of the present disclosure.

FIGS. 13C-13E are enlarged, longitudinal cross-sectional views of cassette body 910 proximate to pump chamber 925. Opening 925a of the pump chamber 925 (e.g., when piston 945 is retracted) is disposed between the inlet-side valve 922 and outlet-side valve 924 along a bottom the fluid pathway section 923. In some embodiments, the nose or tip of the piston 945 is substantially aligned with a bottom of fluid pathway section 923 (FIG. 13E) to eliminate any dead space (e.g., internal space where air may accumulate) in pump chamber 925 as well as reduce any drag associated with the fluid flow through the fluid pathway section 923. Thus, in some embodiments, the dead space is less than 1% of the total volume of the pump chamber 925. For example, in certain embodiments, the volume of the pump chamber is 80 microliters when the piston 945 is fully retracted in its reciprocating cycle.

In this regard, it can be advantageous to place the inlet-side valve 922 and outlet-side valve 924 close together along the fluid pathway section 923 proximal to the pump chamber 925. For example, a distance between the inlet-side valve 922 and outlet-side valve 924 is approximately between 4 millimeters and 7 millimeters in some embodiments. It is to be appreciated that piston pump techniques can provide repeatedly precise positive displacement of fluid in the pump chamber 925.

In accordance with certain embodiments, a section or tract of the fluid pathway leading from the area of the outlet-side valve 924 may comprise a straight edge portion 923a that is tangent to an arcuate edge 934a of the downstream pressure dome 934. The tangentially aligned straight edge 923a and arcuate edge 934a are top edge portions with respect to an orientation of the cassette 900 with respect to gravity, for example, as the cassette 900 would be installed into cassette recess 1000 such that longitudinal axis or y-axis 195 is substantially aligned with gravity.

With respect to the orientation of pump chamber 925 of cassette 900 and pump chamber having pump chamber opening/access 125 of cassette 100, in certain embodiments, it may be advantageous to have pump chamber 925 in order to prevent or limit the impact of air bubbles in pump chamber accuracy. For example, in pump chamber having pump chamber opening/access 125 during the delivery phase of the pump cycle, fluid will be expelled first and any air that accumulates in the pump chamber of cassette 100 and between the inlet-side valve 122, outlet-side valve 124 will remain thereby decreasing pumping accuracy of the system. In contrast, pump chamber 925 of cassette 900 will first expel any air that is in the pump chamber, thereby preventing air from accumulating in the pump chamber 925 and in the region between the inlet-side valve 922, outlet-side valve 924 and maintaining accuracy. For example, with additional reference to the example of FIG. 13F, one or more fluid sensors may be disposed within sensor slot 1028. The one or more fluid sensors disposed within sensor slot 1028 can be ultrasonic sensors configured as an air-in-line detector, for example. In certain embodiments, extension member 928 may be disposed on cassette body 910 and positioned along the fluid pathway between downstream pressure dome 934 and flow stop valve 964. However, in some embodiments, extension member 928 can be positioned at other locations along the fluid pathway such as, but not limited to, between inlet 912 and upstream pressure dome 932. Additionally, in other embodiments, a plurality of extension members 928 with a plurality of corresponding sensor slots 228 may be positioned along a fluid pathway of cassette body 910.

With reference to the examples illustrated in FIGS. 13A-13E, cassette body 910 may include a pump drive assembly in accordance with certain embodiments. For example, the pump drive assembly may include pump drive mechanism 942 for receiving pump actuator 1042 of cassette recess 1000. Pump drive mechanism 942 can be operatively coupled to piston 945 slidably engaged within piston guide 943 or casing (e.g., generally cylindrical or frustoconical casing) such that reciprocal movement of piston 945 may urge fluid into and out of the pump chamber 925 and through the fluid pathway of cassette body 910. In this regard, the pump chamber 925 may be defined by a portion of the piston guide 943 or casing distal from the pump drive mechanism 942 that is adjacent to and fluidly coupled with a tract or section of the fluid pathway between inlet-side valve 922 and outlet-side valve 924. Piston 945 may comprise one or more one or more slideable seals 946 for defining a changeable volume portion of the pump chamber during reciprocal movement of piston 945 slidably disposed within the piston guide 943. Thus, the volume in pump chamber 925 changes with the reciprocal motion of the piston 945 such that a volume of the pump chamber 925 may be varied by movement of the piston 945 in accordance with certain embodiments.

A wiper seal (not shown) may be positioned within or proximal to piston guide 943 and slidably engaged with piston 945 thereby reducing the possibility of any substances (e.g., dirt or dried fluid particles) near the cassette 900 from contacting one or more slidable seals of the piston 945. The one or more slideable seals 946 of the piston 945 may contact an internal wall piston guide 943 to form a movable barrier of the pump chamber 925. Additionally, piston 945 may include a reduced tip portion for more precise volumetric displacement of fluid into and out of pump chamber 925.

For example, pumping operation of infusion pump system 10, 11 when cassette 900 is primed and seated in cassette recess 1000 may comprise activating outlet-side valve actuator 1024 such that outlet-side valve 924 is closed or sealed while activating inlet-side valve actuator 1022 such that inlet-side valve 922 is opened. Opening of inlet-side valve 922 may coincide with or occur shortly after a reverse stroke of piston 945 (e.g., a movement of piston 945 away from pump chamber 925). Accordingly, fluid can flow from upstream pressure dome 932 to pump chamber 925. Alternatively, or in addition to, outlet-side valve 924 may comprise a one-way valve mechanism that permits flow of fluid under normal conditions in one direction (from a fluid container to a patient). Additionally, inlet-side valve 922 may also comprise a one-way valve mechanism permitting flow of fluid in one direction (from a fluid container to a patient) under normal operating conditions. In this configuration, cassette recess 1000 may not need to incorporate either outlet-side valve actuator 1024 or inlet-side valve actuator 1022. Outlet-side valve 924 and inlet-side valve 922 may limit flow of fluid in one direction, but permit flow in an opposite direction in the event fluid pressure overcomes a cracking pressure of the valves.

Continuing with the valve-operated implementation, pumping operation may comprise activating outlet-side valve actuator 1024 such that outlet-side valve 924 is open while activating inlet-side valve actuator 1022 such that inlet-side valve 922 is closed or sealed. Opening of outlet-side valve 924 may coincide with or occur shortly before a forward stroke of piston 945 (e.g., a movement of piston 945 toward the opening of the pump chamber 925 such that the volume of the pump chamber 925 is reduced). Thus, fluid can flow from pump chamber 925 to downstream pressure dome 934 and consequently urging fluid out outlet 914.

In certain embodiments, pump chamber 925 is a smaller volume than one or both of upstream pressure dome 932 and downstream pressure dome 934. Accordingly, larger and compliant upstream pressure dome 932 and/or downstream pressure dome 934 can address any backpressure issues in the IV set, thereby allowing for an accurate and precise volume of fluid entering pump chamber 925 to be pumped.

Referring to FIGS. 13A-13F, pump drive mechanism 942 and pump actuator 1042 may be configured as a reciprocating motion mechanism (e.g., a scotch-yoke configuration) in certain implementations. Pump drive mechanism 942 may be accessible by pump actuator 1042 via an aperture through interface-facing sider section 976. In such implementations, pump drive mechanism 942 may include opposing ramp portions for guiding a rotatable pin of pump actuator 1042 toward an elongate slot of pump drive mechanism 942. For example, the outer edges of the opposing ramp portions may be arranged a distance that will ensure engagement with the rotatable pin of pump actuator 1042. When the rotatable pin contacts one of the ramp portions, the pump drive mechanism 942 will move to align the elongate slot of pump drive mechanism 942 with the with the rotatable pin of pump actuator 1042. However, it is to be appreciated that other pump drive assemblies are contemplated with cassette 900 and cassette recess 1000 in accordance with the present disclosure.

In certain embodiments, cassette recess 1000 may include an upstream pressure sensing probe 1032 and downstream pressure sensing probe 1034 enabling measurement of in-line pressure and fault isolation to a section of the fluid pathway. For example, upstream pressure sensing probe 1032 may operably contact upstream pressure dome 932 through a corresponding opening of interface-facing frame portion 916. Similarly, downstream pressure sensing probe 1034 may operably contact downstream pressure dome 934 through a corresponding opening of frame portion 916.

The x-y positioning of cassette 900 within cassette recess 1000 can be constrained by the positioning port 920 and positioning protrusion 1020 mating interface, as well as fluid pathway extension member 928 and sensor slot 1028 mating interface (e.g., air-in-line detector feature). In this regard, cassette 900 and cassette recess 1000 can have two points of contact in the z-axis direction (e.g., an axis through and transverse to a general plane of the interface-facing surface of cassette body 910 of cassette 900 and cassette-facing surface of cassette recess 1000) for interlock alignment of the cassette with respect to the x-y positioning of the interface side of the cassette body 910.

According to certain aspects, positioning port 920 may be located proximal to inlet-side valve 922 and outlet-side valve 924, and correspondingly mating positioning protrusion 1020 may be located proximal to inlet-side valve actuator 1022 and outlet-side valve actuator 1024. In this regard, the cassette 900 may be positioned properly without over constraining the cassette 900.

In other words, the controlling index for proper x-axis and y-axis alignment of the interface-facing frame portion 916 is the positioning port 920 and positioning protrusion 1020 mating interface, in certain embodiments. In some embodiments, the positioning port 920 and positioning protrusion 1020 mating interface, and fluid pathway extension member 928 and sensor slot 1028 mating interface, together form the controlling index for proper x-axis and y-axis alignment of the interface-facing frame portion 916 (e.g., dual-feature x-y positioning scheme).

However, in certain embodiment, the latching engagement of slider 970 with cassette recess 1000 provides tight tolerances for z-axis positioning of the cassette body 910 and corresponding interface-facing frame portion 916 for operation with the cassette-facing surface 1016 of cassette recess 1000 (e.g., z-axis alignment or distances require for proper operation of the pressure sensors as well as valve actuators). It is to be understood that techniques of z-axis alignment or depth other than slider protrusion 974 positioning are contemplated.

Figure 13F:
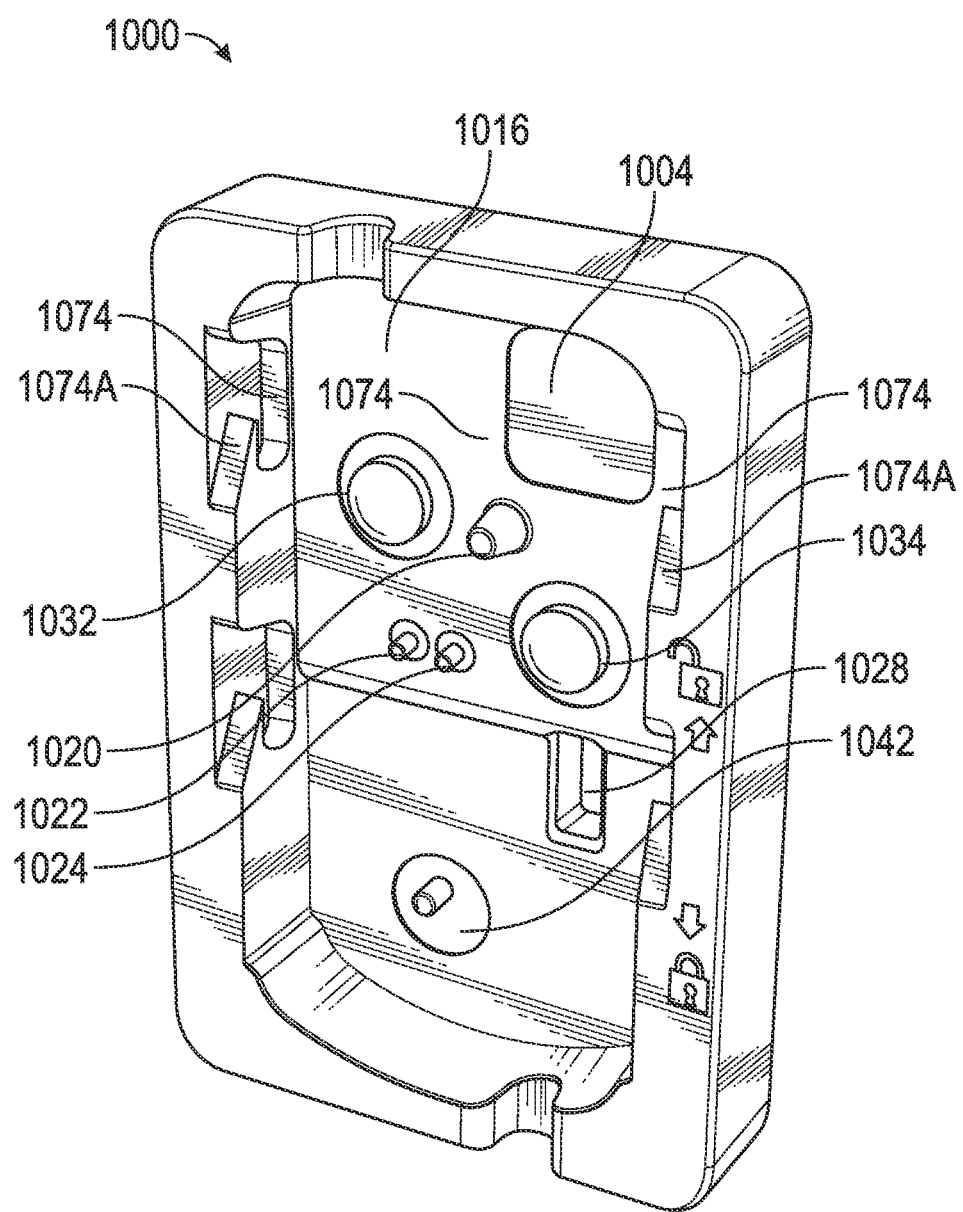
FIG. 13F illustrates a perspective view of an example of a fifth embodiment cassette recess, in accordance with aspects of the present disclosure.

It is to be understood that positioning protrusion 1020 may have various cross sectional geometries in addition to the circular cross-section protrusion/pin-type illustrated in FIG. 13F and other figures. For example, pin may have a triangular, square, or other polygonal cross-section. For instance, a polygonal shape may be used to provide tighter tolerances to the x-y positioning of the cassette body 910 when cassette 900 has an air-in-line features the does not protrude into and received by cassette recess 1000. Alternatively or in addition, the slider 970 may be configured have to tighter tolerances with respect to the x-axis and/or y-axis. For example, the x-axis tolerance may be substantially tight so as to avoid or substantially limit any minor or miniscule rotation of the cassette body 910 during prolonged continuous operation with infusion pump system 10, 11. Moreover, the positioning port 920 and positioning protrusion 1020 mating interface can be reversed in some implementation (e.g., the positioning protrusion may be disposed on cassette 900).

However, in some implementations of cassette 900 and cassette recess 1000, a dual-feature x-y positioning scheme as described herein can be advantageous so as to avoid too much stress on a single mating feature. For example, positioning protrusion 1020 having a circular cross-section cooperatively engaging with positioning port 920 can provide tight tolerances for either the x-axis or y-axis alignment of interface-facing frame portion 916, but not necessarily both x-axis or y-axis alignment as rotation between positioning protrusion 1020 and positioning port 920 can occur. However, in conjunction with a second x-y positioning such as fluid pathway extension member 928 and sensor slot 228 mating interface, tight tolerances can be achieved without undue stress on either of the x-y positioning features, as well as the cassette 900 and cassette recess 1000 in general.

Accordingly, advantages of the x-y positioning schemes disclosed herein include, but are not limited to, preventing sheering to sensor features (e.g., upstream pressure sensing probe 1032 and downstream pressure sensing probe 1034 may not engage with sensors until they are properly aligned by the x-y positioning features, aiding in full and proper valve operation (e.g., inlet-side valve actuator 1022 and outlet-side valve actuator 1024 may not fully close a corresponding valve if misaligned on the x-axis and/or y-axis occurs), and assisting with communicating a correct timing for latching slider 970 of cassette 900 with cassette recess 1000 (e.g., caregiver can sense engagement of x-y positioning features between cassette 900 and cassette recess 1000).

Figure 14A:
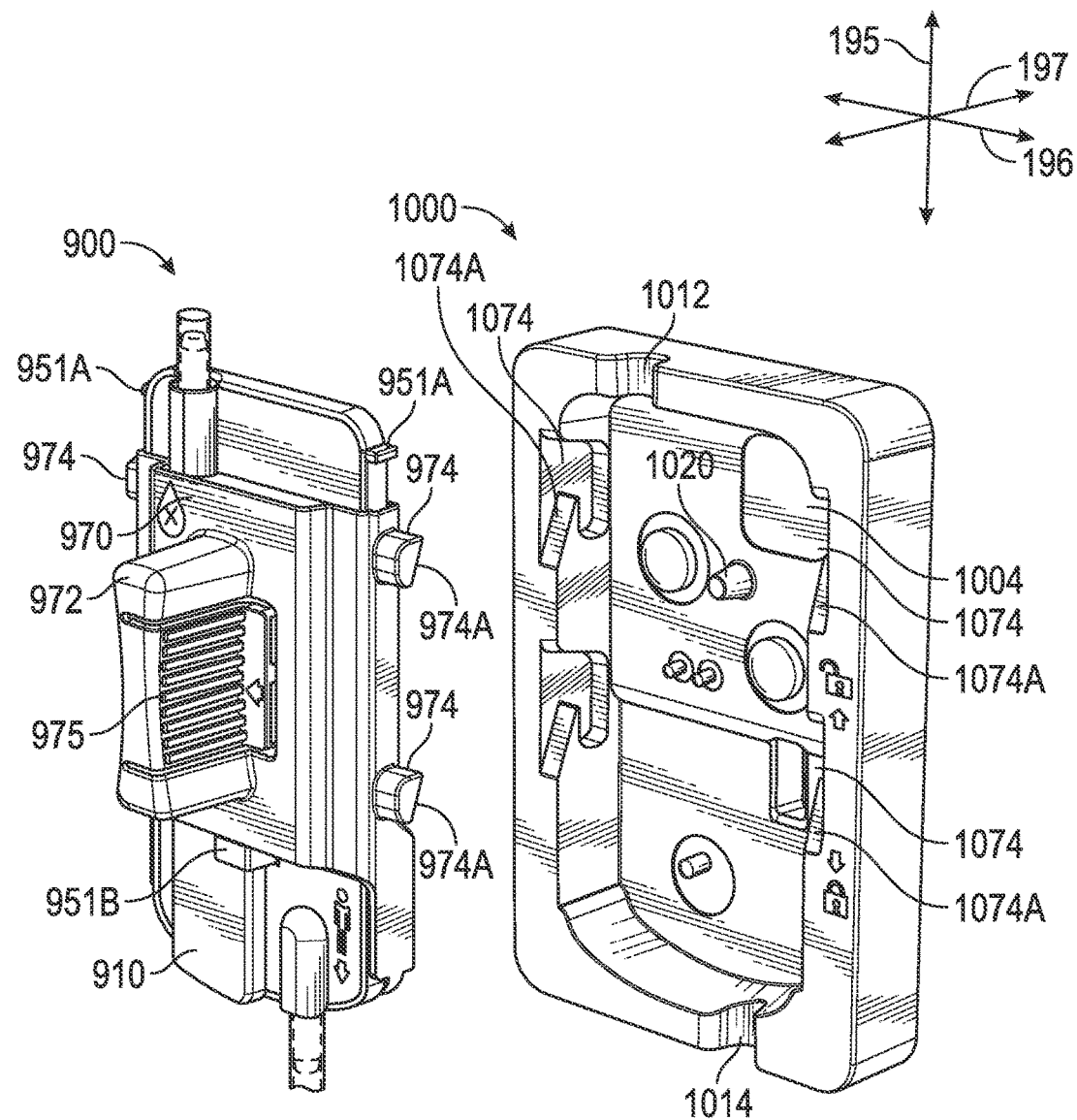
FIG. 14A illustrates perspective views of examples of a fifth embodiment disposable IV pump cassette and cassette recess, in accordance with aspects of the present disclosure.

FIGS. 14A-4D illustrate an example of a cassette engagement sequence with cassette 900 and cassette recess 1000. Cassette 900 may be aligned such that the plurality of protrusions 974 on slider 970 may be aligned along z-axis 197 for engagement with the plurality of slots 1074 of cassette recess 1000. In accordance with certain aspects, cassette 900 may have a longitudinal length along y-axis 195, a lateral width along x-axis 196, and a depth along z-axis 197. As illustrated in FIG. 4A and described herein, the depth of the cassette 900 may be a smaller dimension than either the length or the width of cassette 900. In this regard, cassette 900 is front loaded into cassette recess 1000.

Figure 14B:
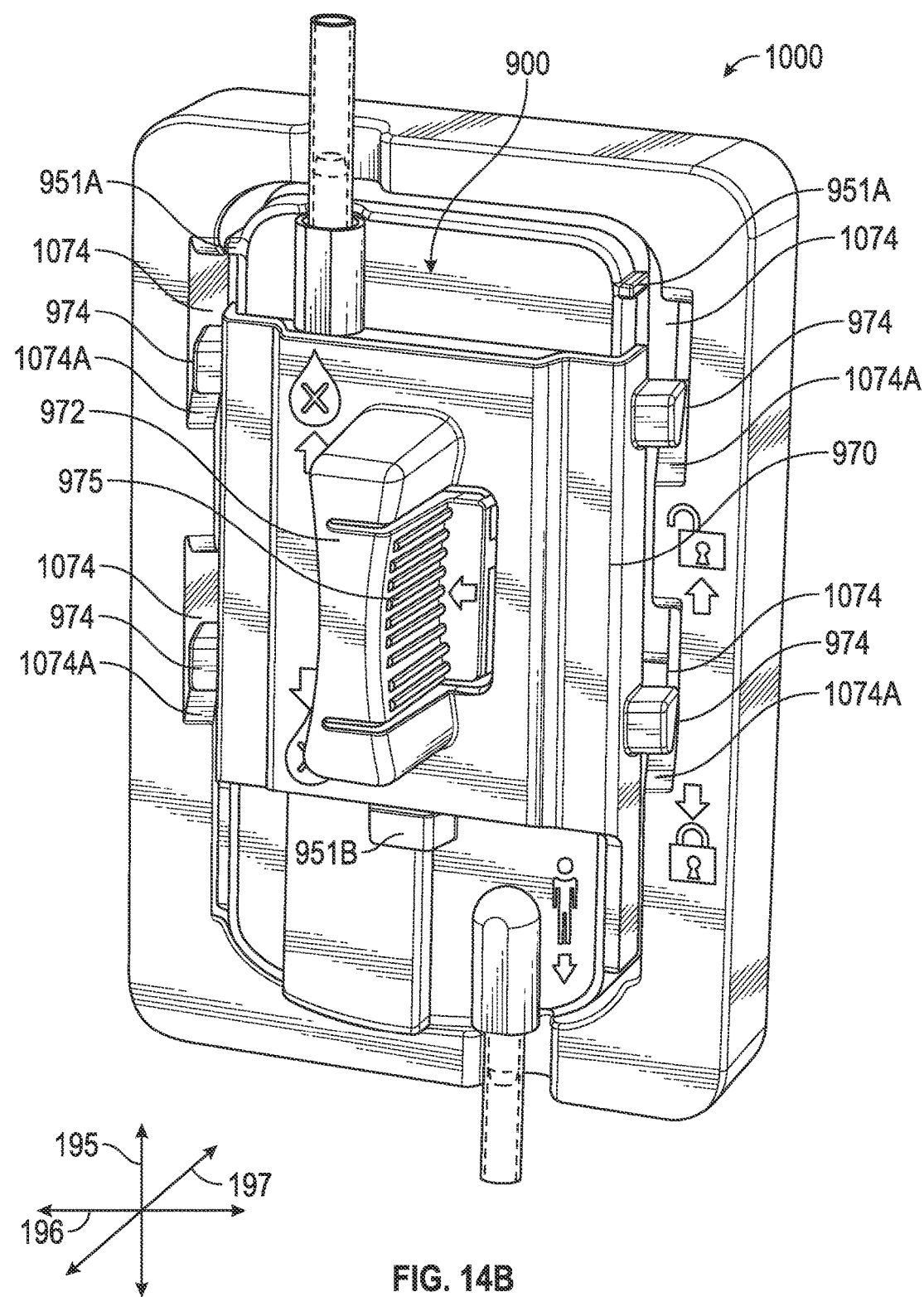
FIG. 14B illustrates perspective views of examples of a fifth embodiment disposable IV pump cassette and cassette recess, in accordance with aspects of the present disclosure.

As illustrated in FIGS. 14A and 14B, the plurality of protrusions 974 on slider 970 of cassette 900 may engage with the plurality of slots 1074 of cassette recess 1000 such that cassette body 910 may be generally aligned with cassette recess 100 and the flat face portions 974a of the plurality of protrusions 974 may contact the respective flat face ramp portions 1074a of the cassette engagement slots 1074 (e.g., slider 970 in the second position with respect to cassette body 910). In certain embodiments, the flat face portions 974a of the plurality of protrusions 974 may have an angled plane different from a general plane of the interface-facing surface of cassette body 910 of cassette 900 and cassette-facing surface 1016 of cassette recess 1000.

Figure 14C:
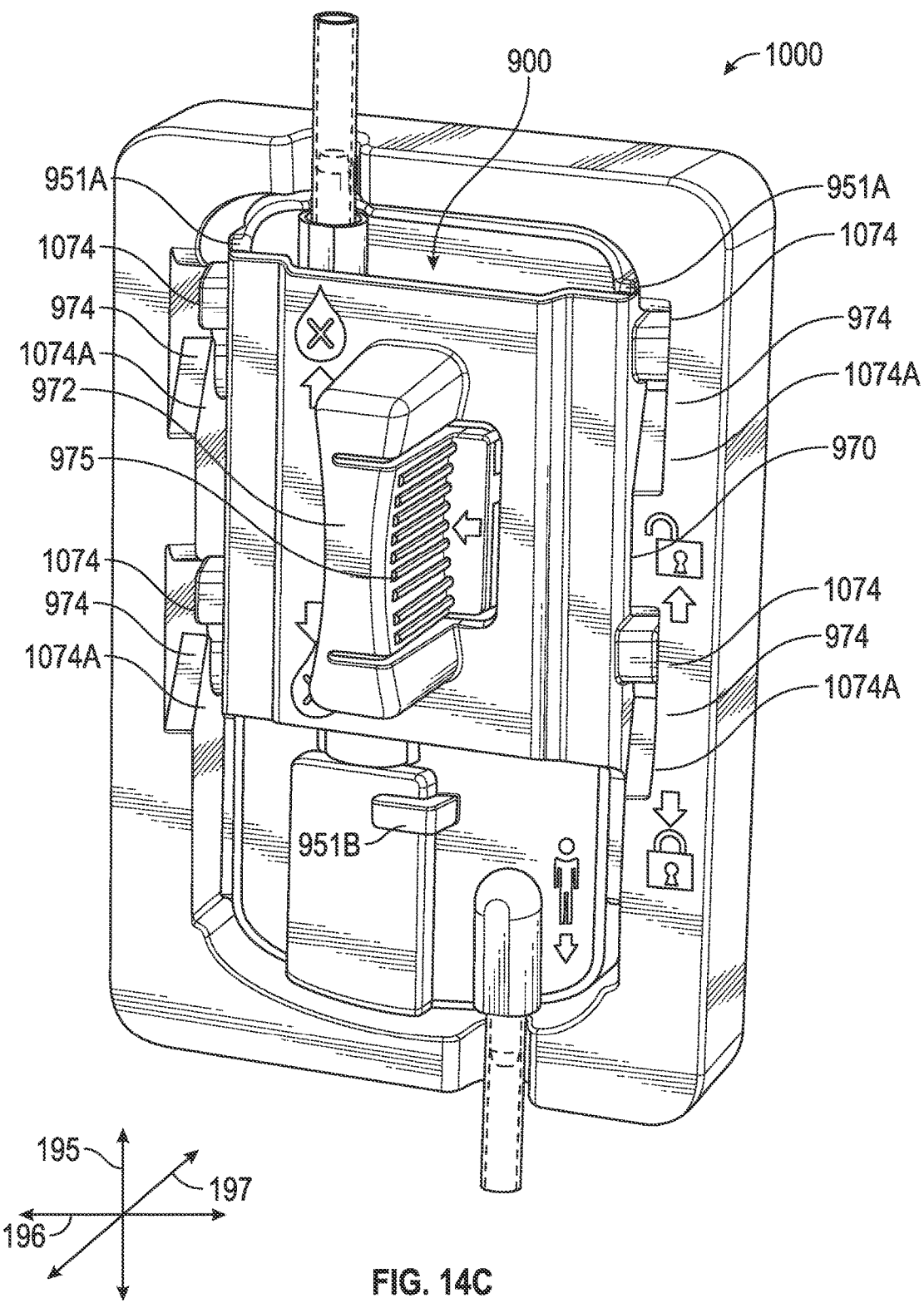
FIG. 14C illustrates perspective views of examples of a fifth embodiment disposable IV pump cassette and cassette recess, in accordance with aspects of the present disclosure.

Next, as illustrated in FIG. 14C, when a force is into the to the slider 970 substantially orthogonal to general plane of the interface-facing surface of cassette body 910 of cassette 900 and cassette-facing surface 1016 of cassette recess 1000, the slider 970 articulates in a direction from the second position to the first position. In this regard, the plurality of engagement protrusions 974 may slide along the respective flat face ramp portions 1074a of the cassette engagement slots 1074 deeper into the cassette recess 1000.

Figure 14D:
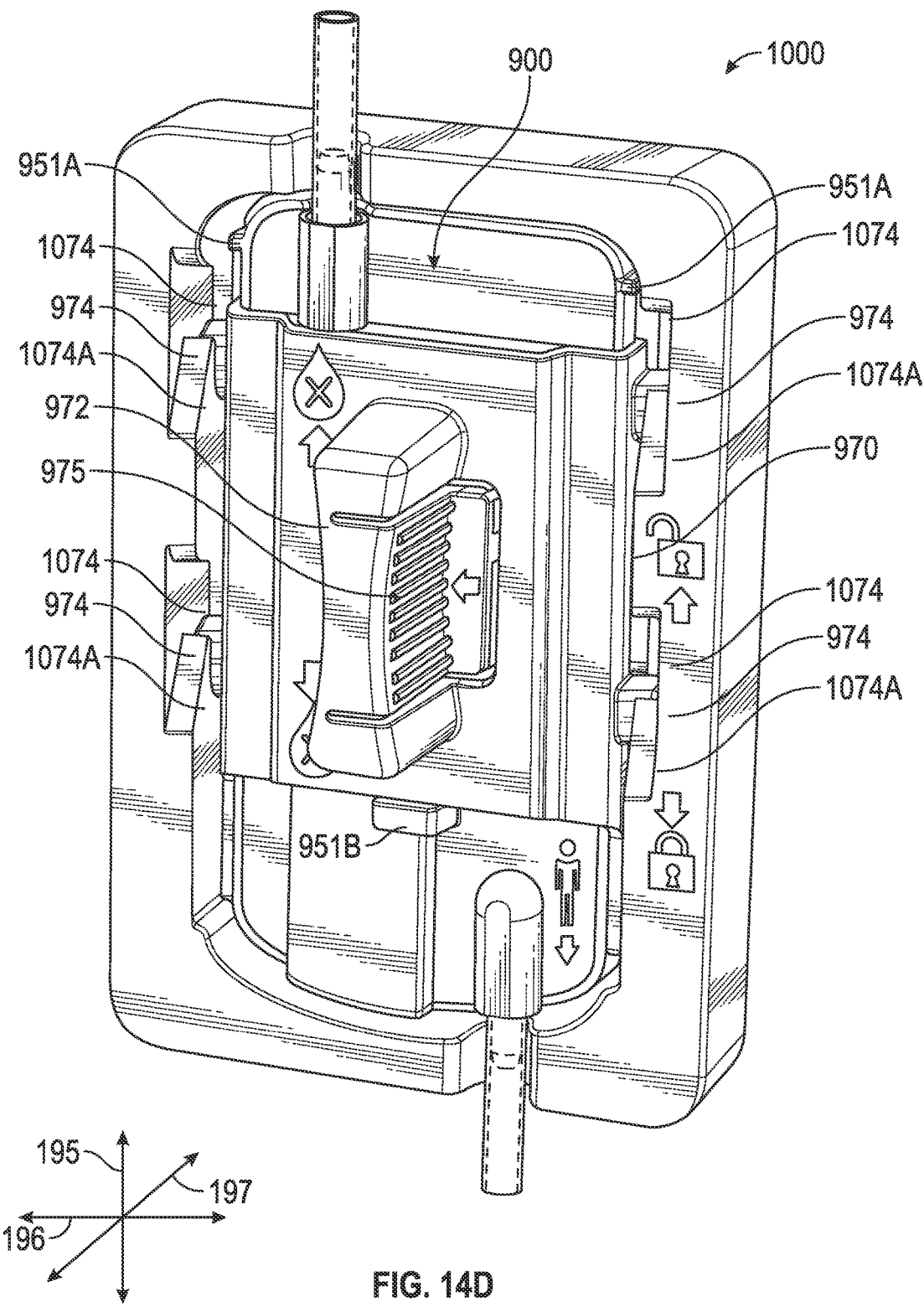
FIG. 14D illustrates perspective views of examples of a fifth embodiment disposable IV pump cassette and cassette recess, in accordance with aspects of the present disclosure.

Next, as illustrated in FIG. 14D, slider 970 may be longitudinally articulated along y-axis 195 such that cassette 900 is latched and locked by slider 970 within cassette recess 1000. For example, the plurality of engagement protrusions 974 may be positioned behind the flat face ramp portions 1074a of the cassette engagement slots 1074 while cassette 900 is engaged and operational with cassette recess 1000. It is to be noted that in some embodiments, loading of cassette 900 within cassette recess 1000 may be laterally oriented (e.g., 90° rotation of z-axis 197 so that x-axis 196 and y-axis 195 are switched).

In certain embodiments, flow stop valve 964 may be configured to restrict and/or regulate fluid flow proximal to outlet 914 of cassette body 910. In the first position, flow stop valve 964 is aligned under a portion (e.g., flat surface) of interface-facing slider section 976 of slider 970. When the slider 970 is positioned in the first position, the portion of interface-facing slider section 976 contacts and activates flow stop valve 964 such that fluid flow is occluded at that position of the fluid pathway proximal to outlet 914 cassette body 910. Therefore, fluid leakage can be avoided during the final preparation stages (e.g., after priming of cassette 900) and prior to the start of insertion stage into cassette recess 1000, in accordance with certain implementations. Moreover, in accordance with certain configurations, the first position of slider 970 may correspond to a position of cassette 900 for disengaging with cassette recess 1000.

Slider 970 can be articulated to a second position with respect to cassette body 910 (e.g., articulated downwardly in certain implementations). In this second position, cassette 900 will be latched within cassette recess 1000 by virtue of protrusions 974 being engaged with slots 1074 and locked by virtue of slider 970 with respect to cassette body 910. In the second position, flow stop valve 964 is aligned under a stop valve guard 978 (e.g., ramped, rounded, or recessed surface) of interface-facing slider section 976 of slider 970. When the slider 970 is positioned in the second position, the portion of interface-facing slider section 976 does not contact flow stop valve 964 (or does not contact flow stop valve 964 sufficiently to activate flow stop valve 964), and flow stop valve 964 operates to allow fluid to flow freely through flow stop valve 964 to outlet 914.

In accordance with certain embodiments, stop valve guard 978 may be positioned underneath a portion of and/or proximal to an edge along interface-facing slider section 976 of slider 970 such that when cassette 900 is securely latched or locked within cassette recess 1000 (e.g., in the second position), stop valve guard 978 is positioned above flow stop valve 964. In this regard, stop valve guard 978 can protect flow stop valve 964 from being inadvertently depressed and activated to restrict fluid flow while cassette 900 is in use. For example, a force applied to the slider side of cassette 900 while locked within cassette recess 1000 would not depress flow stop valve 964 as the lateral tolerances of the slidable coupling between cassette 900 and slider 970 are tighter than a distance between the inner surface of the stop valve guard 978 and an outer surface of the flow stop valve 964. In this regard, distances between stop valve guard 978 and flow stop valve 964 may be optimized such that anticipated forces applied to cassette 900 (e.g., from a user or caregiver inadvertently bumping cassette 900 or road vibrations in moving ambulance setting) may not cause an undesired activation of flow stop valve 964.

Similarly, when cassette 900 is to be disengaged from cassette recess 1000, slider 970 can be unlatched and/or unlocked from cassette recess 1000 by accessing grip 972, squeezing flexible portion 975 to unlock slider 970, and articulating slider 970 back to the first position with respect to cassette body 910. Some amount of force may be required by the user to articulate slider 970 to the first position as the plurality of protrusions 974 may be securely latched with corresponding slots 1074 while the slider 970 is in the second position. Once slider 970 is in the first position, cassette 900 may be removed from cassette recess 1000 by pulling grip 972 outwardly.

Furthermore, slider 970 may be articulated from the first position to the second position when cassette 900 is not engaged with cassette recess 1000. Thus, flow stop valve 964 will operate to allow fluid to flow freely through flow stop valve 964 to outlet 914. Therefore, cassette 900 may be primed with fluid while being disengaged from cassette recess 1000 when slider 970 is in the second position (but not latched with cassette recess 1000).

Figure 14E:
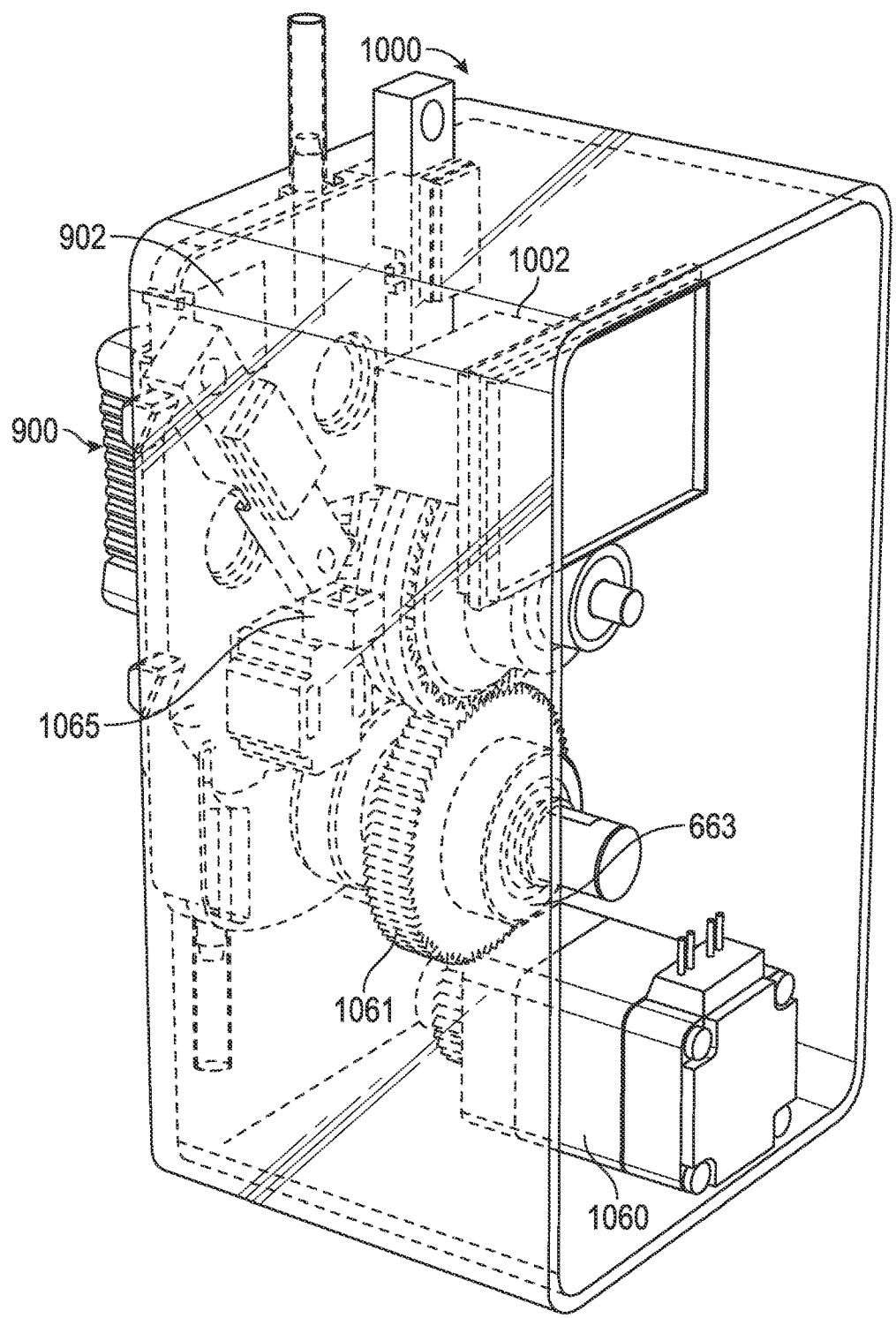
FIG. 14E illustrates rear perspective views of examples of a fifth embodiment disposable IV pump cassette and cassette recess, along with examples of interface structures, in accordance with aspects of the present disclosure in accordance with aspects of the present disclosure.

It is to be understood that in other implementations, the stop valve guard feature can be a recess distal from an edge of interface-facing slider section 976, or an aperture or slit extending through interface-facing slider section 976, for example. Moreover, in some embodiments, flow stop valve and stop valve guard features may be positioned on the slider-facing side of cassette body 910. It is to be understood that various constructions of flow stop valve 964 are contemplated in the present disclosure as described herein. As illustrated in FIGS. 13F and 14E, cassette recess 1000 may include interface structures operable in conjunction with infusion pump systems 10, 11. For example, pump actuator 1042 may be configured to provide a rotational force aligned with piston drive mechanism 942 (e.g., for use with scotch-yoke pumping configurations).

Cassette recess 1000 additionally includes inlet-side valve actuator 1022 and outlet-side valve actuator 1024, in accordance with some embodiments. Inlet-side valve actuator 1022 and outlet-side valve actuator 1024 may be disposed proximate to the back surface of the cassette recess 1000, and during operation, portions of inlet-side valve actuator 1022 and outlet-side valve actuator 1024 may extend beyond the back surface (e.g., during a forward stroke of inlet-side valve actuator 1022 or outlet-side valve actuator 1024 to close inlet-side valve 922 or outlet-side valve 924, respectively).

In accordance with some embodiments, motor 1060 operatively coupled to the infusion pump system 10, 11 (e.g., processing unit 12, 13). For example, processing unit 12, 13 may provide signals to control a speed of the rotation of motor 1060. Motor 1060 may be mechanically coupled to a plurality of gears 1061 such that a motor shaft is operative to rotate pump actuator 1042 as well as reciprocate inlet-side valve actuator 1022 and outlet-side valve actuator 1024 via a cam arrangement 1063. Cam arrangement 1063 may comprise a plurality of cams formed and/or aligned to provide proper valve and pump actuator operation as described herein. An optical flag detector 1065 may be included to identify rotations of the cam arrangement, for example. However, it is to be appreciated that other pump drive assemblies are contemplated with cassette 900 and cassette recess 1000, in accordance with the present disclosure.

In some embodiments, scanner (or reader) 1002 may be operably coupled to infusion pump system 10, 11 (e.g., processing unit 12, 13) such that cassette identifier 902 can be scanned through window (or aperture) 1004. Additionally, an air-in-line detector 1029 may be operable to detect air in the controllable fluid path of cassette 900 via fluid pathway extension member 928, for example. Cassette recess 1000 may include various mechanical couplings and operational interfaces, such as but not limited to an inlet-side pressure sensing probe 1032 and an outlet-side pressure sensing probe recess 1034 thereby enabling measurement of in-line pressure and fault isolation to a section of the fluid pathway. For example, inlet-side pressure sensing probe 1032 may operably contact upstream pressure dome 932 through a corresponding opening of interface-facing frame portion 916. Similarly, outlet-side pressure sensing probe may operably contact downstream pressure dome 934 through a corresponding opening of frame portion 916.

Figure 15A:
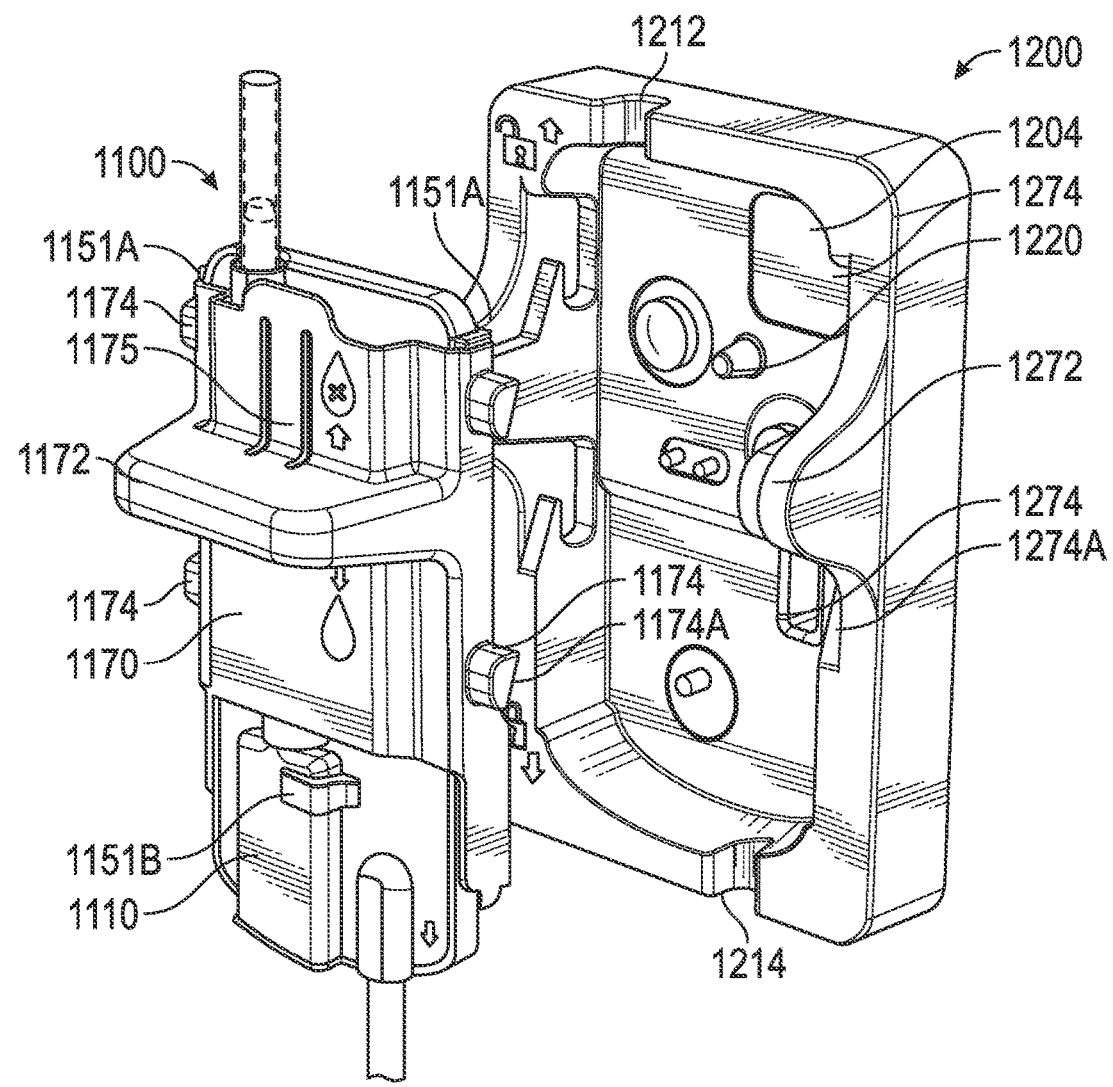
FIG. 15A illustrates perspective views of examples of a sixth embodiment disposable IV pump cassette and cassette recess, in accordance with aspects of the present disclosure.
Figure 15B:
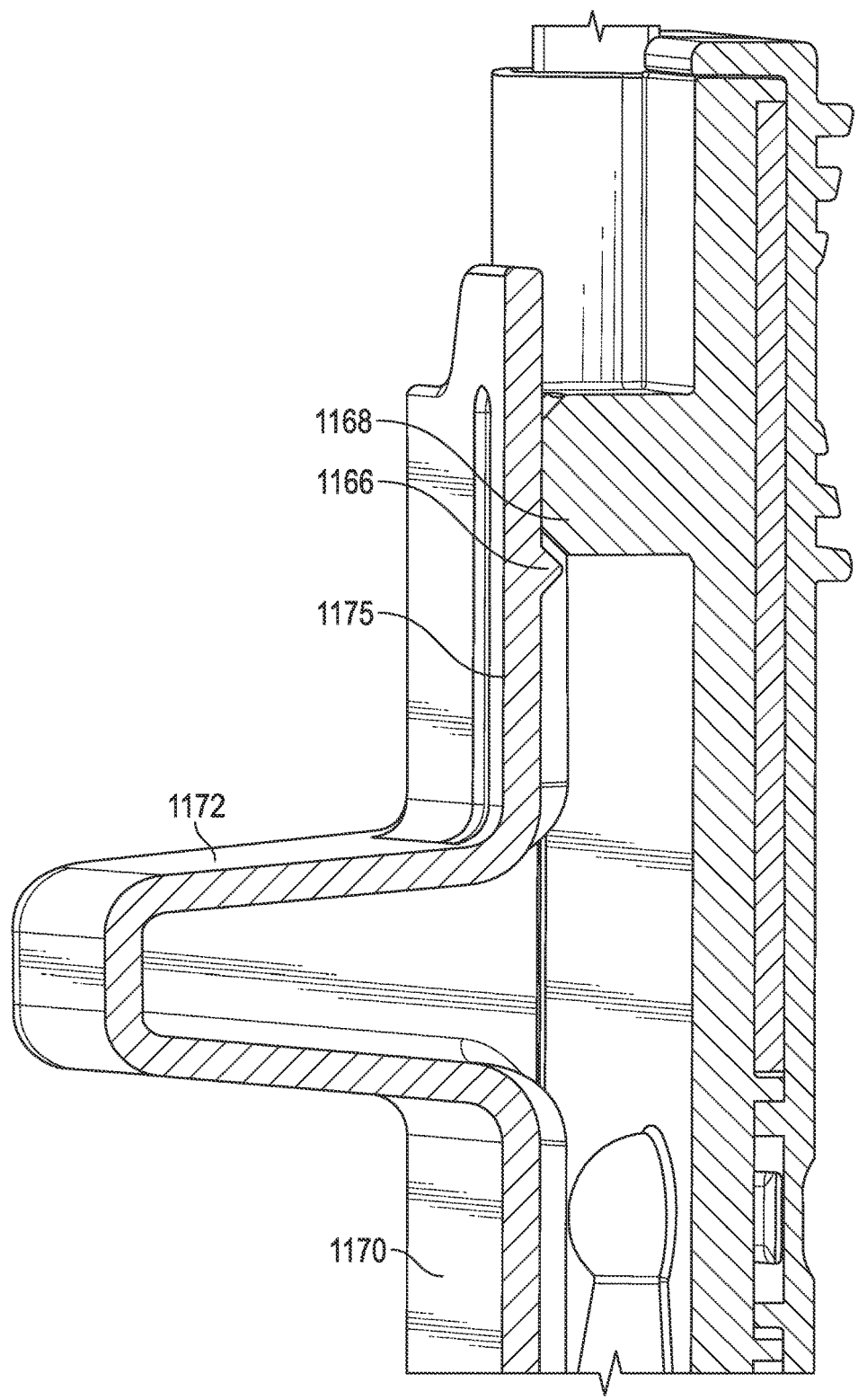
FIG. 15B illustrates an enlarged cross-sectional perspective view of an example of a sixth embodiment disposable IV pump cassette, in accordance with aspects of the present disclosure.
Figure 15C:
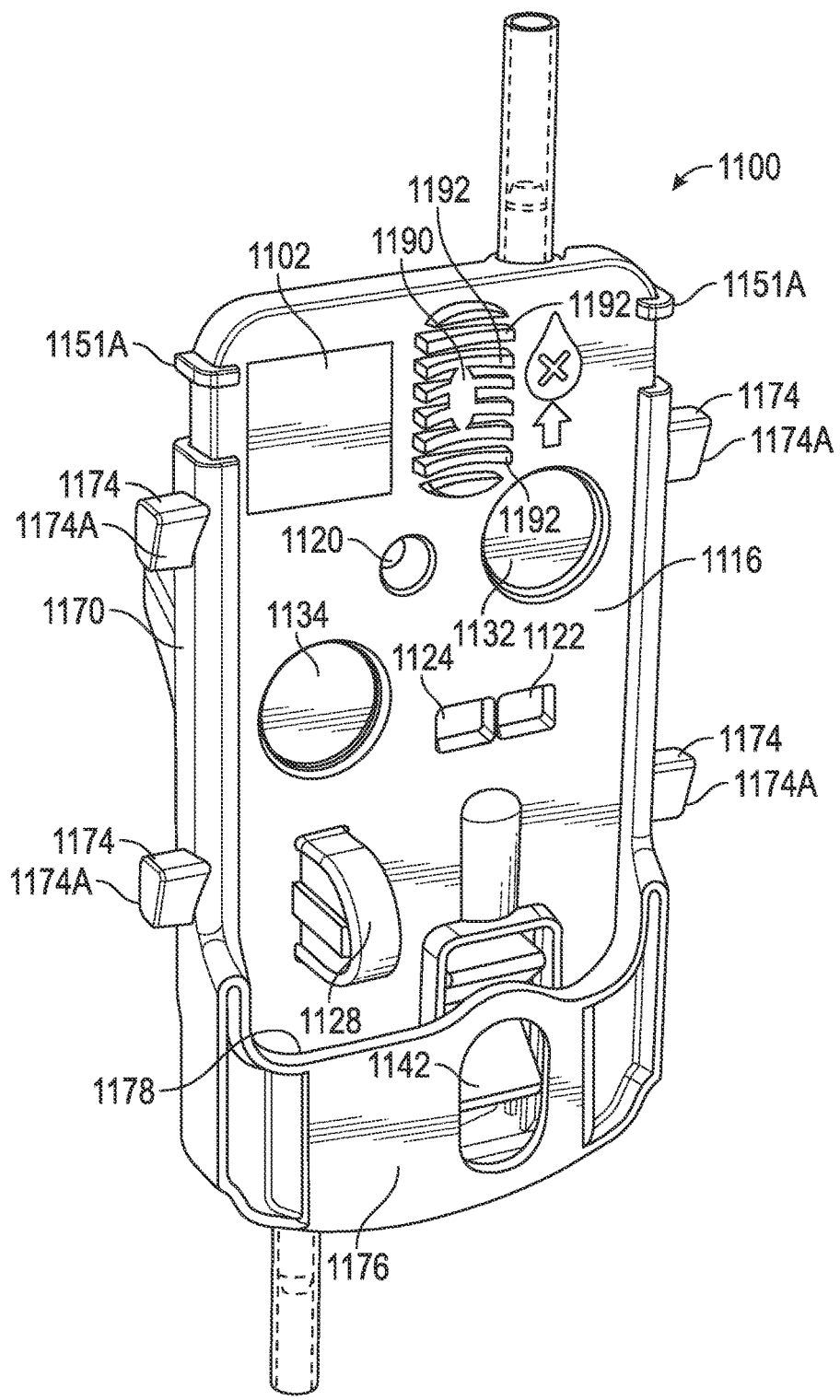
FIG. 15C illustrates a perspective view of an example of a sixth embodiment disposable IV pump cassette, in accordance with aspects of the present disclosure.

FIGS. 15A-15C illustrate examples of a disposable IV pump cassette 1100 and corresponding cassette recess 1200 of an interface module. In accordance with certain embodiments, cassette 1100 may comprise a cassette body 1110 and a slider 1170. Cassette 1100 and cassette recess 1200 may have similar components and features as like numbered components and features in other example embodiments described herein, particularly with respect to cassette 900 and cassette recess 1000.

With reference to the examples of FIGS. 15A and 15B (illustrating an enlarged, cross-sectional perspective view of cassette 1100), slider 1170 may be a lockable slider in a first and second position in accordance with certain embodiments. Thus, slider 1170 may be configured to articulate such that the slider 1170 is movably fixable at one or more positions with respect to cassette body 1110. For example, slider 1170 may include slider grip 1172 such that a user or caregiver may hold to articulate slider 1106. Slider 1170 may also include a flexible segment 1175 that is configured to retain the slider 1170 in a fixed position with respect to the cassette body. In this regard, the flexible segment 1175 may provide an amount of resistance or friction to moving or articulating slider 1170 along a longitudinal path.

The longitudinal path of slider 1170 may be constrained by one or more slider stoppers, for example top slider stopper 1151*a* and bottom slider stopper 1151*b*. Flexible segment 1175 may be capable or being biased (e.g., bent or bowed) to overcome the resistance provided for restricting longitudinal motion. For example, flexible segment 1175 may include one or more slots disposed on a portion of the slider 1170 facing the cassette body to alter the pliability of that portion.

In certain embodiments, flexible segment 1175 may include a slider segment tab 1166 that interfaces with a body tab 1168 disposed on a slider-facing side of cassette body 1110. For example, slider segment tab 1166 may have an angled face (e.g., a triangular cross-section) that contacts a respective angled face of an edge portion of body tab 1168 when the slider 1170 is in the second position such that the slider segment tab 1166 is aligned longitudinally below the body tab 1168. Thus, to articulate slider 1170 from the second position to the first position (e.g., articulating the slider 1170 upwardly with respect to the cassette body 1110), a user or caregiver must overcome the resistance provided by the flexible segment 1175 for fixing the slider 1170 in the second position. When sufficient force is applied to the slider 1170, slider flexible segment 1166 will bend or bow and slider segment tab 1166 will slide over a top of body tab 1168 until slider segment tab 1166 reaches an opposite side of body tab 1168, for example. The slider 1170 will then be in the first position with respect to cassette body 1110, in accordance with certain embodiments.

Slider segment tab 1166 may have a similarly angled face that contacts a respective angled face of an edge portion of body tab 1168 when the slider 1170 is in the first position such that the slider segment tab 1166 is aligned longitudinally above the body tab 1168. Thus, to articulate slider 1170 from the first position back to the second position (e.g., articulating the slider 1170 downwardly with respect to the cassette body 1110), the user or caregiver must again overcome the resistance provided by the flexible segment 1175 for fixing the slider 1170 in the first position. When sufficient force is applied to the slider 1170, slider flexible segment 1166 will bend or bow and slider segment tab 1166 will slide over a top of body tab 1168 until slider segment tab 1166 reaches an opposite side of body tab 1168, for example. The slider 1170 will then be in the second position with respect to cassette body 1110, in accordance with certain embodiments.

When the slider segment tab of the flexible segment 1175 reaches either end of the body tab 1168, the flexible segment may snap back to the unbiased state (e.g., unbent or unbowed position) and generate an audible sound (e.g., a click) and/or vibration in the slider grip 1172 when the flexible segment 1175 contact the top of the body tab 1168. In this regard, the user or caregiver can infer that the slider 1170 has reached the first or second position and is now fixed in position. It is to be understood that the amount of force required by a user to articulate slider 1170 to and from the one or more position may adapted to various implementations of cassette 1100 by altering characteristics and geometries of the flexible segment 1175, slider segment tab 1166, and/or body tab 1168.

With reference to the example of FIG. 15C, slider 1170 may be articulated between the first position and the second position when cassette 1100 is not engaged with cassette recess 1200 with the aid of grip feature 1190. In certain embodiments, grip feature 1190 may be arranged on an exterior surface of interface-facing frame portion 1116 of cassette body 1110, and may be defined in part by a plurality ribs 1192 extending from the exterior surface of the interface-facing portion 1116. Grip feature 1190 may include a recessed portion extending into the exterior surface of interface-facing frame portion 1116 (e.g., an indentation on the exterior surface that does not extend beyond a thickness of interface-facing frame portion 1116). Grip feature 1190 may be generally oval-shaped indicative of a thumb or finger support for a user or caregiver, for example.

For example, while holding cassette 1100, a user or caregiver may place a thumb of his or her first hand on grip feature 1190 and longitudinally articulate, with one or more fingers of his or her first hand, for example, slider 1170 of cassette 1100 with respect to the cassette body 1110 from a first position in which flow stop valve 1164 occludes fluid flow to a second position in which flow stop valve 1164 allows fluid flow. As noted herein, slider 1170 of cassette 1100 may be in a movably fixed position when the slider 1170 is in either the first position or the second position such that the user would not need to apply a longitudinal force to overcome the resistance or friction provided by flexible segment 1175 (e.g., by the interaction between segment tab 1166 and body tab 1168).

It is to be understood that aspects of the various embodiments disclosed herein may be intermixed and incorporated such that alternative embodiments may include one or more aspects from one or more embodiments combined in another embodiment. For example, and without limiting the scope of such combinations, alternative embodiments may include: flat face ramp portions 874a, 1074a, 1274a of cassette recess 800, 1000, and 1200 with any of the other cassette recesses 200, 400, 600; flow stop valve 164 and interface-facing slider section 176 include one or more cassette-facing detents 179 of cassette 100 (FIGS. 5E and 5D) with any of the other cassettes 300, 500, 700, 900, 1100; vertically-oriented and lockable slider grips 772, 972 of cassettes 700, 900 with any of the other cassettes 100, 300, 500, 1100; and pump structure 541 configured for orthogonal piston assembly operation of cassette 500 with any of the other cassettes 100, 300, 700, 900, 1100.

The subject technology is illustrated, for example, according to various aspects described above. Various examples of these aspects are described as numbered concepts or clauses (1, 2, 3, etc.) for convenience. These concepts or clauses are provided as examples and do not limit the subject technology. It is noted that any of the dependent concepts may be combined in any combination with each other or one or more other independent concepts, to form an independent concept. The following is a non-limiting summary of some concepts presented herein:

Concept 1. A pump cassette comprising:
a rigid body comprising a frame portion, a base portion, a compliant membrane disposed substantially therebetween, two opposing edge sections, and an interface-facing surface, wherein the rigid body comprises a positioning feature arranged substantially orthogonal to a general plane of the interface-facing surface; and slider coupled to the two opposing edge sections and longitudinally articulable with respect to the rigid body.

Concept 2. The pump cassette of concept 1 or any other concept, wherein the positioning feature is defined in part by the frame portion.

Concept 3. The pump cassette of concept 1 or any other concept, wherein the positioning feature comprises a positioning port defining a recess into the interface-facing surface.

Concept 4. The pump cassette of concept 1 or any other concept, wherein the positioning feature comprises a positioning protrusion extending from the interface-facing surface.

Concept 5. The pump cassette of concept 4 or any other concept, wherein the rigid body further comprises a controllable fluid pathway defined in part by the compliant membrane and extending from an inlet port to an outlet port, and
wherein the positioning protrusion comprises a fluid pathway extension member of the controllable fluid pathway.

Concept 6. The pump cassette of concept 4 or any other concept, wherein the rigid body further comprises a controllable fluid pathway defined in part by the compliant membrane and extending from an inlet port to an outlet port, and
wherein the positioning protrusion comprises a pump structure configured to urge fluid through the controllable fluid pathway.

Concept 7. The pump cassette of concept 6 or any other concept, wherein the pump structure comprises an external support wall portion extending from the interface-facing surface.

Concept 8. The pump cassette of concept 1 or any other concept, wherein the positioning feature comprises a first positioning protrusion and a second positioning protrusion, each extending from the interface-facing surface.

Concept 9. A pump cassette comprising:
a rigid body comprising a compliant membrane, two opposing edge sections, and an interface-facing surface, wherein the rigid body comprises a controllable fluid pathway including a pump chamber, the controllable fluid pathway defined in part by the compliant membrane and extending from an inlet port to an outlet port;
a pump assembly including a pump drive mechanism operably accessible from the interface-facing surface, wherein the pump drive mechanism is longitudinally articulable with respect to the rigid body; and
a slider coupled to the two opposing edge sections and longitudinally articulable with respect to the rigid body.

Concept 10. The pump cassette of concept 9 or any other concept, wherein the pump assembly further comprises a piston disposed within the rigid body and the pump drive mechanism is operably coupled to the piston.

Concept 11. The pump cassette of concept 10 or any other concept, wherein the piston is arranged in a position above an opening of the pump chamber such that a piston head can vary a volume of the pump chamber when the pump drive mechanism is longitudinally articulated.

Concept 12. The pump cassette of concept 11 or any other concept, wherein the position above the pump chamber is a position that is proximal to the inlet port and distal from the outlet port.

Concept 13. The pump cassette of concept 10 or any other concept, wherein the piston is arranged in a position below an opening of the pump chamber such that a piston head can vary a volume of the pump chamber when the pump drive mechanism is longitudinally articulated.

Concept 14. The pump cassette of concept 13 or any other concept, wherein the position below the pump chamber is a position that is proximal to the outlet port and distal from the inlet port.

Concept 15. The pump cassette of concept 10 or any other concept, wherein the piston is arranged in a rail for guiding the piston during a piston stroke.

Concept 16. The pump cassette of concept 9 or any other concept, wherein the rigid body comprises a positioning feature arranged on the interface-facing surface such that the positioning feature is proximal to the pump chamber and distal from either of the inlet port and the outlet port.

Concept 17. The pump cassette of concept 9 or any other concept, wherein the slider comprises a lens area configured to magnify the controllable fluid pathway.

Concept 18. An infusion pump system comprising:
a processing unit;
a cassette recess configured to receive a pump cassette, the cassette recess comprising (i) a plurality of cassette engagement slots configured for removably coupling the pump cassette, and (ii) a cassette-facing surface comprising a positioning feature slot extending orthogonal to a general plane of the cassette-facing surface.

Concept 19. The infusion pump system of concept 18 or any other concept, wherein the cassette-facing surface comprises a positioning protrusion extending from the cassette-facing surface.

Concept 20. The infusion pump system of concept 18 or any other concept, wherein the positioning feature slot comprises (i) a first positioning feature slot operably coupled to a pump actuator configured to apply a force orthogonal to the general plane of cassette-facing surface, and (ii) a second positioning feature slot operably coupled to a fluid sensor.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

One or more aspects or features of the subject matter described herein may be realized in digital electronic circuitry, integrated circuitry, specially designed ASICs (application specific integrated circuits), computer hardware, firmware, software, and/or combinations thereof. For example, infusion pump systems disclosed herein may include an electronic system with one or more processors embedded therein or coupled thereto. Such an electronic system may include various types of computer readable media and interfaces for various other types of computer readable media. Electronic system may include a bus, processing unit(s), a system memory, a read-only memory (ROM), a permanent storage device, an input device interface, an output device interface, and a network interface, for example.

Bus may collectively represent all system, peripheral, and chipset buses that communicatively connect the numerous internal devices of electronic system of an infusion pump system. For instance, bus may communicatively connect processing unit(s) with ROM, system memory, and permanent storage device. From these various memory units, processing unit(s) may retrieve instructions to execute and data to process in order to execute various processes. The processing unit(s) can be a single processor or a multi-core processor in different implementations.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, or operations in the processes or methods disclosed are illustrations of exemplary approaches. Based upon implementation preferences or scenarios, it is understood that the specific order or hierarchy of steps, operations or processes may be rearranged. Some of the steps, operations or processes may be performed simultaneously. In some implementation preferences or scenarios, certain operations may or may not be performed. Some or all of the steps, operations, or processes may be performed automatically, without the intervention of a user. The accompanying method claims present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but is to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A pump cassette comprising:
   a rigid body comprising a frame portion, a base portion, a compliant membrane disposed substantially therebetween, two opposing edge sections, and an interface-facing surface;
   a controllable fluid pathway defined at least in part by the base portion and the compliant membrane;
   a first positioning feature on the frame portion and arranged substantially orthogonal to a general plane of the interface-facing surface, the first positioning feature configured to mechanically interact with a first corresponding positioning feature on a surface of a cassette recess of an infusion pump for positioning of the pump cassette within the cassette recess;
   a second positioning feature on the frame portion, laterally separated from the first positioning feature, arranged substantially orthogonal to the general plane of the interface-facing surface, and configured to mechanically interact with a second corresponding positioning feature on the surface of the cassette recess of the infusion pump for positioning of the pump cassette within the cassette recess, wherein the second positioning feature comprises a protrusion on the frame portion within which a portion of the controllable fluid pathway is disposed; and
   a slider coupled to the two opposing edge sections and longitudinally articulable with respect to the rigid body.

2. The pump cassette of claim 1, wherein the first positioning feature comprises a positioning port defining a recess into the interface-facing surface, the recess configured to receive the first corresponding positioning feature on the surface of the cassette recess of the infusion pump.

3. The pump cassette of claim 1, wherein the first positioning feature comprises a first positioning protrusion extending from the interface-facing surface, the first positioning protrusion configured to be received by the first corresponding positioning feature on the surface of the cassette recess of the infusion pump.

4. The pump cassette of claim 3, the controllable fluid pathway extending from an inlet port to an outlet port, and wherein the second positioning feature comprises a fluid pathway extension member of the controllable fluid pathway.

5. The pump cassette of claim 3, the controllable fluid pathway extending from an inlet port to an outlet port, and wherein the pump cassette further comprises a pump structure configured to urge fluid through the controllable fluid pathway.

6. The pump cassette of claim 5, wherein the pump structure comprises an external support wall portion extending from the interface-facing surface.

7. The pump cassette of claim 1, wherein the second positioning feature comprises a fluid pathway extension member extending from the interface-facing surface and configured to be received in a sensor slot in the cassette recess to provide monitoring access to the portion of the controllable fluid pathway by an ultrasonic air-in-line sensor in the sensor slot.

8. A pump cassette comprising:
   a rigid body comprising a compliant membrane, two opposing edge sections, and an interface-facing surface, wherein the rigid body comprises a controllable fluid pathway including a pump chamber, the controllable fluid pathway defined in part by the compliant membrane and extending from an inlet port to an outlet port, wherein the rigid body includes a positioning feature on the frame portion and arranged substantially orthogonal to a general plane of the interface-facing surface, the positioning feature configured to mechanically interact with a first corresponding positioning feature on a surface of a cassette recess of an infusion pump for positioning of the pump cassette within the cassette recess;

a pump assembly including a pump drive mechanism operably accessible from the interface-facing surface, wherein the pump drive mechanism is longitudinally articulable with respect to the rigid body; and a slider coupled to the two opposing edge sections and longitudinally articulable with respect to the rigid body.

9. The pump cassette of claim 8, wherein the pump assembly further comprises a piston disposed within the rigid body and the pump drive mechanism is operably coupled to the piston.

10. The pump cassette of claim 9, wherein the piston is arranged in a position above an opening of the pump chamber such that a piston head can vary a volume of the pump chamber when the pump drive mechanism is longitudinally articulated.

11. The pump cassette of claim 10, wherein the position above the pump chamber is a position that is proximal to the inlet port and distal from the outlet port.

12. The pump cassette of claim 9, wherein the piston is arranged in a position below an opening of the pump chamber such that a piston head can vary a volume of the pump chamber when the pump drive mechanism is longitudinally articulated.

13. The pump cassette of claim 12, wherein the position below the pump chamber is a position that is proximal to the outlet port and distal from the inlet port.

14. The pump cassette of claim 9, wherein the piston is arranged in a rail for guiding the piston during a piston stroke.

15. The pump cassette of claim 8, wherein the slider comprises a lens area configured to magnify the controllable fluid pathway.

16. A pump cassette comprising:
a rigid body comprising a frame portion, a base portion, a compliant membrane disposed substantially therebetween, two opposing edge sections, and an interface-facing surface;
a controllable fluid pathway defined at least in part by the base portion and the compliant membrane;
a first positioning feature on the frame portion and arranged substantially orthogonal to a general plane of the interface-facing surface, the first positioning feature configured to mechanically interact with a first corresponding positioning feature on a surface of a cassette recess of an infusion pump for positioning of the pump cassette within the cassette recess; and
a pump assembly including a pump drive mechanism operably accessible from the interface-facing surface, wherein the pump drive mechanism is longitudinally articulable with respect to the rigid body.

17. The pump cassette of claim 16, further comprising a second positioning feature on the frame portion, laterally separated from the first positioning feature, arranged substantially orthogonal to the general plane of the interface-facing surface, and configured to mechanically interact with a second corresponding positioning feature on the surface of the cassette recess of the infusion pump for positioning of the pump cassette within the cassette recess, wherein the second positioning feature comprises a protrusion on the frame portion within which a portion of the controllable fluid pathway is disposed.

18. The pump cassette of claim 17, wherein the second positioning feature comprises an air-in-line extension on the frame portion, and wherein the pump drive mechanism is configured to receive a pump actuator from the cassette recess of the infusion pump to drive a piston in the pump cassette.

* * * * *

UNITED STATES PATENT AND TRADEMARK OFFICE
CERTIFICATE OF CORRECTION

PATENT NO.        : 10,245,373 B2
APPLICATION NO.   : 14/557447
DATED             : April 2, 2019
INVENTOR(S)       : Daniel Toro et al.

It is certified that error appears in the above-identified patent and that said Letters Patent is hereby corrected as shown below:

On the Title Page

Item (56) References Cited should read:
FOREIGN PATENT DOCUMENTS
WO    WO-2005097235 A2  10/2005
WO    WO-2014190188 A2  11/2014
WO    WO-2016190904 A1  12/2016

Signed and Sealed this
Fourteenth Day of May, 2019

Andrei Iancu
*Director of the United States Patent and Trademark Office*